US008835153B2

(12) United States Patent
Seibert et al.

(10) Patent No.: US 8,835,153 B2
(45) Date of Patent: Sep. 16, 2014

(54) PROCESS AND GENES FOR EXPRESSION AND OVEREXPRESSION OF ACTIVE [FEFE] HYDROGENASES

(75) Inventors: Michael Seibert, Lakewood, CO (US);
Paul W. King, Golden, CO (US); Maria Lucia Ghirardi, Lakewood, CO (US);
Matthew C. Posewitz, Golden, CO (US); Sharon L. Smolinski, Littleton, CO (US)

(73) Assignee: Alliance for Sustainable Energy, LLC, Golden, CO (US)

( * ) Notice: Subject to any disclaimer, the term of this patent is extended or adjusted under 35 U.S.C. 154(b) by 1667 days.

(21) Appl. No.: 11/573,035

(22) PCT Filed: Feb. 28, 2006

(86) PCT No.: PCT/US2006/007153
§ 371 (c)(1),
(2), (4) Date: Nov. 4, 2008

(87) PCT Pub. No.: WO2006/093998
PCT Pub. Date: Sep. 8, 2006

(65) Prior Publication Data
US 2009/0087880 A1    Apr. 2, 2009

Related U.S. Application Data

(60) Provisional application No. 60/656,957, filed on Feb. 28, 2005.

(51) Int. Cl.
*C12N 1/21*    (2006.01)
*C12N 15/70*    (2006.01)

(52) U.S. Cl.
USPC ..................... 435/252.3; 435/320.1; 435/471

(58) Field of Classification Search
None
See application file for complete search history.

(56) References Cited

U.S. PATENT DOCUMENTS 6,858,718 B1 *   2/2005   Happe ........................ 536/23.2
2004/0209256 A1  10/2004  Dillon

FOREIGN PATENT DOCUMENTS

WO   2008021223 A3   2/2008

OTHER PUBLICATIONS

Posewitz et al. (JBC, 2004, vol. 279: 25711-25720).*
Stoker et al. Journal of Bacteriology, 1989, vol. 171, No. 8, pp. 4448-4456.*
Chaudhuri et al. Journal of General Microbiology, 1987, vol. 133, pp. 3289-3298.*
Posewitz et al., "Discovery of Two Novel Radical S-Adenosylmethionine Proteins Required for the Assembly of an Active [Fe] Hydrogenase," J. Biol. Chem. vol. 279, No. 24, 25711-25720 (2004).
International Search Report dated Aug. 16, 2006, for International Application No. PCT/US2006/007153.
International Preliminary Report on Patentability dated Sep. 11, 2007, for International Application No. PCT/US2006/007153.
Supplementary European Search Report dated Jun. 17, 2008, for European Application No. EP 06 73 6467.
Forestier, et al, "Expression of two [Fe]-hydrogenases in *Chlamydomonas reinhardtii* under Anaerobic Conditions", Eur. J. Biochem., vol. 270, 2750-2758 (2003).
Nixon, et al, "Iron-Dependent Hydrogenases of *Entamoeba histolytica* and *Giardia lamblia*:. Activity of the Recombinant Entamoebic Enzyme and Evidence for Lateral Gene Transfer", Biol. Bull. vol. 204: 1-9 (Feb. 2003).
Happe, et al, "Differential Regulation of the Fe-Hydrogenase during Anaerobic Adaptation in the Green Alga *Chlamydomonas reinhardtii*", Eur. J. Biochem., vol. 269, 1022-1032 (2002).
Posewitz, et al, "Discovery of two Novel Radical SAM Proteins Required for the Assembly of an Active [Fe]-hydrogenase", JBC Papers in Press, Manuscript (Apr. 13, 2004).
Ghirardi, et al, "Biological Systems for Hydrogen Photoproduction", DOE Hydrogen Program, FY 2004 Progress Report.
Davies J.P. et al, "Sac3, an Snf1-like Serine/Threonine . . . to Sulfur Limitation", Plant Cell, vol. 11, 1179-1190 (1999).
V. Lumbreras et al, "Efficient Foreign Gene . . . by and Endogenous Intron", Plant J., 441-448 (1998).
H. J. Sofia et al, "Radical SAM . . . Visualization Methods", Nucleic Acids Res., 1097-1106 (2001).
P. M. Vignais et al, "Classification and Phylogeny of Hydrogenases", FEMS Microbiol. Rev., vol. 25, 455-501 (2001).
T. Happe et al, "Isolation, Characterization and N-terminal Amino Acid Sequence of Hydrogenase from the Green Alga *Chlamydomonas reinhardtii*", Eur. J. Biochem., vol. 214, 475-481 (1993).
N. K. Menon et al, "Mutational Analysis and Characterization of the *Escherichia coli* hya Operon, Which Encodes [NiFe} Hydrogenase 1", J. Bacteriol., vol. 173, 4851-4861 (1991).
A. Jacobi et al, "The hyp Operon Gene Products are Required for the Maturation of Catalytically Active Hydrogenase Isoenzymes in *Escherichia coli*", Arch. Microbiol, vol. 158, 444-451(1992).
R. M. Allen "Incorporation of Iron and Sulfur from NifB Cofactor into the Iron-Molybdenum Cofactor of Dinitrogenase", J. Biol. Chem., vol. 270, 26890-26896 (1995).

(Continued)

*Primary Examiner* — Celine Qian
(74) *Attorney, Agent, or Firm* — John C. Stolpa

(57) ABSTRACT

A process for expression of active [FeFe]-hydrogenase in a host organism that does not contain either the structural gene(s) for [FeFe]-hydrogenases and/or homologues for the maturation genes HydE, HydF and HyG, comprising: cloning the structural hydrogenase gene(s) and/or the maturation genes HydE, HydF and HydG from an organisms that contains these genes into expression plasmids; transferring the plasmids into an organism that lacks a native [FeFe]-hydrogenase or that has a disrupted [FeFe]-hydrogenase and culturing it aerobically; and inducing anaerobiosis to provide [FeFe] hydrogenase biosynthesis and H?2#191 production.

8 Claims, 11 Drawing Sheets

(56) References Cited

OTHER PUBLICATIONS

G. Pan et al, "Characterization of a [2Fe-2S] Protein Encoded in the Iron-Hydrogenase Operon of *Thermotoga maritima*", J. Biol. Inorg. Chem., vol. 8, 469-474 (2003).

L. Casalot et al, "Maturation of the [NiFe] Hydrogenases", Trends Microbiol., vol. 9, 228-237 (2001).

G. Voordouw et al, "Purification and Characterization of *Desulfovibrio vulgaris* (Hildenborough) Hydrogenase Expressed in *Escherichia coli*", Eur. J. Biochem, vol. 162, 31-36 (1987).

Y. Asada et al, "Heterologous Expression of Clostridial Hydrogenase in the Cyanobacterium *Synechococcus* PCC7942", Biochem. Biophys. Acta., vol. 1490, 269-278 (2000).

L. Girbal et al, "Homologous and Heterologous . . . with High Specific Activities", Appl. Env. Microbiol., vol. 71, 2777-2781 (2005).

K. L. Kindle "High-Frequency Nuclear Transformation of *Chlamydomonas reinhardtii*" Proc. Natl. Acad. Sci., USA, vol. 87, 1228-1232 (1990).

Ghirardi et al., "Microalgae: a Green Source of Renewable H2", Trends in Biotechnology, Elsevier, vol. 18, No. 12, 2000, pp. 506-511.

King, et al, "Functional Studies of [FeFe] Hydrogenase Maturation in an *Escherichia coli* Biosynthetic System", Journal of Bacteriology, vol. 188, No. 6, 2163-2172 (2006).

* cited by examiner

Figure 3

Homologues of the *C. reinhardtii* putative [Fe]-Hydrogenase maturation proteins.

| Organism | Orf | % I | E value | Homology Length | Rank | Genome Organization |
|---|---|---|---|---|---|---|
| T. maritima | HydG | 45 | -122 | 75-565 | 2 | Putative genes/operon: HydG, unknown, HydE, Cystathionine γ-synthetase. Putative homologue to algal [Fe]-Hydrogenase gene ungrouped. |
| | HydE | 35 | -57 | 104-483 | 4 | |
| | HydF | 29 | -35 | 12-404 | 10 | |
| | HydA1 | 48 | -104 | 66-497 | 1 | |
| C. thermocellum | HydG | 46 | -122 | 74-566 | 3 | Putative homologues to algal [Fe]-Hydrogenase and maturation-protein genes are ungrouped. |
| | HydE | 35 | -53 | 122-474 | 5 | |
| | HydF | 30 | -42 | 5-384 | 12 | |
| | HydA1 | 45 | -93 | 86-485 | 3 | |
| B. thetaiodaomicron | HydG | 46 | -112 | 122-564 | 7 | Putative genes/operon: [Fe]-Hydrogenase, HydE, HydG, HydF, Alanyl dipeptidyl peptidase, Poly-Hydroxybutarate depolymerase. |
| | HydE | 32 | -47 | 124-474 | 6 | |
| | HydF | 27 | -39 | 12-447 | 3 | |
| | HydA1 | 42 | -89 | 67-485 | 5 | |
| T. tengcongensis | HydG | 38 | -93 | 61-566 | 11 | Putative homologues to algal [Fe]-Hydrogenase and maturation-protein genes are ungrouped. |
| | HydE | 35 | -59 | 100-480 | 3 | |
| | HydF | 29 | -39 | 12-468 | 5 | |
| | HydA1 | 44 | -96 | 84-485 | 2 | |
| D. vulgaris | HydG | 47 | -124 | 73-567 | 1 | Putative operon: HydA ([Fe]-Hydrogenase large sub-unit), HydB ([Fe]-Hydrogenase sub-unit), HydF, HydE, Putative aspartate-ammonia lyase, HydG. |
| | HydE | 31 | -37 | 123-452 | 10 | |
| | HydF | 30 | -39 | 12-465 | 4 | |
| | HydA1 | 41 | -81 | 90-485 | 8 | |
| C. acetobutylicum | HydG | 41 | -105 | 74-564 | 9 | Putative homologues to algal [Fe]-Hydrogenase and maturation-protein genes are ungrouped. |
| | HydE | 35 | -62 | 126-479 | 1 | |
| | HydF | 28 | -39 | 12-398 | 11 | |
| | HydA1 | 37 | -72 | 66-485 | 9 | |
| C. perfringens | HydG | 41 | -108 | 71-565 | 8 | Putative homologues to algal [Fe]-Hydrogenase and maturation-protein genes are ungrouped. |
| | HydE | 34 | -60 | 99-480 | 2 | |
| | HydF | 28 | -38 | 12-464 | 8 | |
| | HydA1 | 37 | -71 | 66-485 | 10 | |
| D. desulfuricans | HydG | 44 | -116 | 73-567 | 5 | Putative operon: HydL ([Fe]-Hydrogenase large sub-unit), HydS ([Fe]-Hydrogenase small sub-unit), unknown, HydG, HydE, HydF. |
| | HydE | 30 | -34 | 126-479 | 12 | |
| | HydF | 29 | -38 | 56-467 | 9 | |
| | HydA1 | 45 | -88 | 86-485 | 6 | |
| C. botulinum | HydG | 41 | -101 | 129-566 | 12 | Putative genes/operon: HydE, HydG, HydF. Putative homologue to algal [Fe]-Hydrogenase gene ungrouped. |
| | HydE | 44 | -43 | 272-474 | 8 | |
| | HydF | 28 | -40 | 1-468 | 1 | |
| | HydA1 | 46 | -91 | 85-485 | 4 | |
| C. difficile | HydG | 42 | -102 | 75-567 | 10 | Putative genes/operon: HydG, HydE, HydF. Putative homologue to algal [Fe]-Hydrogenase gene ungrouped. |
| | HydE | 29 | -45 | 121-474 | 7 | |
| | HydF | 28 | -40 | 12-430 | 2 | |
| | HydA1 | 40 | -82 | 85-485 | 7 | |
| S. oneidensis | HydG | 41 | -112 | 50-567 | 6 | Putative genes/operon: HydA ([Fe]-Hydrogenase large sub-unit), HydB ([Fe]-Hydrogenase small sub-unit), Cytochrome B-type, unknown, HydG, HydE, HydF. |
| | HydE | 32 | -37 | 43-318 | 11 | |
| | HydF | 28 | -38 | 12-469 | 7 | |
| | HydA1 | 35 | -62 | 91-486 | 11 | |
| C. tetani | HydG | 43 | -116 | 26-477 | 4 | Putative genes/operon: HydG, HydE, HydF, HymD-type (*E. acidaminophilum* [Fe]-Hydrogenase operon) putative membrane spanning protein. Putative homologue to algal [Fe]-Hydrogenase gene ungrouped. |
| | HydE | 30 | -40 | 100-449 | 9 | |
| | HydF | 27 | -38 | 12-451 | 6 | |
| | HydA1 | 30 | -13 | 72-333 | 12 | |

Figure 6A

HydEF                                                                       E domain

```
C. reinhardtii      MAHSLSAHSRQAGDRKLGAGAASSRPSCPSRRIVRVAAHASASKATPDVPVDDLPPAHARAAVAAANRRARAMASAEAAAET C. reinhardtii      LGDFLGLGKGGLSPGATANLDREQVLGVLEAVWRRGDLNLERALYSHANAVTNKYCGGGVYYRGLVEFSNICQNDCSYCGIR
C. acetobutylicum   ---------MDNIIKLINKAEVTHDLTKDELVTLLKDDTHNEEIYKAADRVREKYVGEEVHLRGLIEFNICKRNCMYCCLR
C. perfringens      -----------MNTIIQKAKETHELSRDEILALLKDDSINEELFKAADEVRKKYLGDEVHLRGLIEFNICKRNCMYCCLR
C. thermocellum     ----MTNMTNMINLIDKLSTTHTLSYDEMYQLIEHRNEELANYLFEKARQVRILYYCHDVYMRGLIEFTNYCRNICYYCGIR
T. maritima         ---------MTGREILEKLERREFTREVLKEALSINDRGFNEALFKLADEIRRKYVGDEVHRAIIEFSNVGRKNGLYCCLR
B. thetaiotaomicron ----------MRQWIDKLREERTLRPEEFRQLLTECDGESLRYINKQAQEVSLRHFGNRIFRSLIEVSNCGRNLCYYCGIR
C. tetani           ---------MKIKDIIDKAYVESNLSQEEIVEILKNKDEYNIKYLFNKAEETTEKYCGHEVNLRGILEFSNYCRCNCSYCGLN
D. desulfuricans    -------------------------MTSRDILEMLAATGGGPVYAEARTVADRFFGRGVYVRGVVEFSNHCRKNCHYCCLR
S. oneidensis       -MITRPSPPAPVTQPTSVKPTLLNTVFSYAEILSLLQGQDDEWLFSRAKLATELEFNCQVYLRGIVEFSNHCRNHCYCCLR C. reinhardtii      NNQKEVWRYTMPVEEVVEVAKWALENGIRNIMLQGGELKTEQRLAYLEACVRAIREETTQLDLEMRARAASTTTAEAAASAQ
C. acetobutylicum   RDNKNIKRYRLEPDEIIHLAKSAKNYGYQTVVLQSGE-----------------------------------DDYYTVEKM
C. perfringens      RDNKNLNRTRLSHEEIIDFAKKAVGYGYKTLVLQGGE-----------------------------------DDYYTVERG
C. thermocellum     KSNCNAERYRLTKEQILECCDVGYELGFRTFVLQGGE-----------------------------------DGYYTDKIL
T. maritima         RDNKNLKRYRMTPEEIVERARLAVQFGAKTIVLQSGE-----------------------------------DPYYMPDVI
B. thetaiotaomicron KGNFNLERYRLSTENILNCCKQGYGLGFRTFVLQGGE-----------------------------------DPALTEERI
C. tetani           VNNNGIKRYRMSKEEIVLVAKEAYEAGYKTLVLQSGE-----------------------------------DLFYTREIL
D. desulfuricans    VANTGLERFRLEPEGILAAAALARELGAGIVVLQSGE-----------------------------------DLRYDRRVI
S. oneidensis       TENRQVTRYRLSNFEILNAVDSIARLGLGIVVLQSGD-----------------------------------DFNYSGNRI C. reinhardtii      ADAEAKRGEPELGVVVSLSVGELPMEQYERLFRAGARRYLIRIETSNPDLYAALHPEFMSWHARVECLRNLKKAGYMLGIGV
C. acetobutylicum   KYIVSEIKKLN--MAITLSIGEKTFEEYEYRKSGADRYLIRIETTDKELYEKLDP-KMSHENRINCLKNLRKLGYEVCGGC
C. perfringens      VPIVKDLKALG--VALTLSIGERPFEEYEALKKAGADRFLLRIETTDRELYEELDP-GMSHENRIQCLKNLRKLGYEVCGGC
C. thermocellum     ADIVSSIKAKYPDCAITLSICEKSYFSYKLLYEAGADRYLLRHETPANAQHYSKLHPPVMSLKNRKQCLYNLKEIGYQVGGGF
T. maritima         SDIVKEIKKMG--VAVTLSLGEWPREYYEKWKEAGADRYVLHRKLRP-DTSFENRLNCLLTLRKELGYETGAGS
B. thetaiotaomicron EDIVSTIRRSYPDCAITLSLGEKSREAYERFFCAGANRYLLRHETYDKEHYQQLHPAGMSCEERLQCLRDLKDIGYQTGGI
C. tetani           CDIIKSIKKIG--DIAITLSTGKRDKEDYRAFKKAGGDRFLIKHETADKNLFSKLHK-GNKLENRIQALKDLKEVGFQAGCGF
D. desulfuricans    GDLVRRIRDTL--DVAVTLSLCDFDRDTYAAYWRDCGADRYLLKMETFDEALHARLRP-GCTVADRLARVEMLQSLGYETGGI
S. oneidensis       STLITEIKRHH--NLAIITLSLGDRKHQELEKWREAGADRYLLKMETFDRALFAQCRP-KANFDRRIARLNYLKSLCQTGGI C. reinhardtii      MVGLPGQTLHDLAGDVMFFRDIKADMIGMGPFITQPGTPATDKWTALYPNANKNSHMKSMFDLTTAMNALVRITMGNVNISA
C. acetobutylicum   LVGLPNQTIESLADDILFFKEIDADMIGVGPFIPNEDTPLGE-------------EKGGEFFMSVKVTALIRLLLPDINIPA
C. perfringens      LVGLPGQKIESLADDILFFKELDVDLMNGIGPFIPNEDTPLKD-------------AEGGQFELALKVMAIVRLLLPDINIPA
C. thermocellum     MVGSPFQTTECVDDLMFIKELQPHMVGIGPFIPHKDVPFAG-------------KPAGTLELTIFLLGIRLMLEYVLLPA
T. maritima         MVGIPGQTIDDIVDDLLFLKEHDFDMVGIGPFIPHPDTPLAN-------------EKKGDFTLTLKMVALTRLLPDSNIPA
B. thetaiotaomicron MVGSPGQTIEHLIQDILFIEQLRPEMGIGPFLSHRDTPFAQ-------------SPSGTVERTLLLSIFRLMHPSALIPA
C. tetani           MIGIPLQDFNTLARDILLLKELDVDMAGIGPFIHPEDDLKG-------------EHKGDTLLTLKVVALSRILKNIHLPA
D. desulfuricans    IVGLPGMTDAILAEDIHRLSQLGLEMIAAGPFIPHPSTPLAA-------------PVDHAIEKSLLVTAVLRLLNPGANIPA
S. oneidensis       LVDLPGMTDAILARDIQHLSELQLDMLACGPFIAHHQTRPFTT-------------SPNGSALKSHRVSALLRMNPGANLPA C. reinhardtii      TTALQAIIPTGREIALERCGANVVMFILTPTQYRESYQLYEGKPCITDTAVCCRRCLDMRLHSVGKTSAAGVWCDPASFLHPI
C. acetobutylicum   TTAMESLYPNGRSIALTSGCANVVMPNVTEGEYRKLYALYFGKICVNDTPGHCRQCISLKINKINRKVSATK-CFRKKSYKES
C. perfringens      TTAMETLNKQGRVIALQCGANVVMPNVTEGEYRKLYALYFGKICTGDTPAHCRGCISGKIRGIGRIVSDGP-GFRANGFKPK
C. thermocellum     TTALGTIHPKGRELGILAGCANVVMPNLSPKEVRSKYLLYDNKICTGDEAAECRMCLTHRIESIGYKLVVSR-GDCKKPN*
T. maritima         TTAMCTIVPGGREITLRCCGANVLMPNWTPSPYRQLYQLYPGKICVFEKDTACIPCVMKMIELLGRKPGRDW-CGRKRVFETV
B. thetaiotaomicron TTALATLTPDGREQGILAGANVVMPNLSPQEERKKYYNNKASLGAESAEGLNILQCQOLEKIGYQISFSR-CDYKQ*
C. tetani           TTSLGVLNKDHKFTSFKCGANVLMQKLEPYKYRRLYEIYFIELREEKSIREERKDVENFILSSGKEIAKHR-GDTLKRSDL*
D. desulfuricans    TSALDALAADGTRLGLDAGCANVVMPSVTPDAVRGGYSLYFGKNAAGRDVRDAVHGLFERLRNAGYTPVADK-GFSRIAGACG
S. oneidensis       TSSLDALDKGAREQALKRGCNVLMPSFTPTKVSGDYSLYPGKNQQHPAAERLNQVCCQIQRHGLIPSFSR-GDSKRTQYVS C. reinhardtii      VGVPVPHDLSSPALAAAASADFHEVGAGPWNPIRLERLVEVPDRYPDPDNHGRKKAGAGKGGKAHDSHDDGDHDDHHHHGA
C. acetobutylicum   IG*--------------------------------------------------------------------------
C. perfringens      TR*--------------------------------------------------------------------------
C. thermocellum     -----------------------------------------------------------------------------
T. maritima         *-----------------------------------------------------------------------------
B. thetaiotaomicron -----------------------------------------------------------------------------
C. tetani           -----------------------------------------------------------------------------
D. desulfuricans    GNADV*------------------------------------------------------------------------
S. oneidensis       RH*---------------------------------------------------------------------------

C. reinhardtii      -----------------------------------------APAGAAAGKGTGAAAIGGGAGASRQRVAGAAAASARLCAGARRAGRV
D. desulfuricans    -------------------------------------------------------------------------MRVRSARKVLARTD
```

Figure 6B

HydEF
F domain

```
C. reinhardtii       VASPLRPAAACRGVAVKAAAAAAGEDAGAGTSGVGSNIVTSPGIASTTAHGVPRINIGVFGVMNAGISTLVNALAQQEACIV
C. acetobutylicum                                                  MNELNSTPKGERLHIALFGKTNVGKSSVINALTSQEIALV
C. perfringens                                           MQFYYLHLAIVEKFMSNFNFTPRGSRIHISLFGKTNSGKSSIINALTGQNISIV
C. thermocellum                                             MGLNFTPSANRLHIGFFGKRNAGKSSVVNAVTGQNLAIV
T. maritima                                                     MRIPDAGFRRYIVVAGRRNVGKSSFMNAIVGQNVSIV
B. thetaiotaomicron                                        MNLVHTPNANRLHIALFGKRNSGKSSLINALTGQDIALV
C. tetani                                                       MQDIPKGNRIHIAFLGRRNAGKSSIINAISNQQVSIV
D. desulfuricans     VALLVVSEAGMEEAEKRMLADLQAMEISALVVFNKQDIADVRPEDVRFCHEAGVREVQVSSVAQKGISELKSAIVEMVPEEL
S. oneidensis                                                    MRYHIALVGRRNSGKSSLLNMLAGQQISIV C. reinhardtii       DS---------TPGTTAD-VKTVLLELHALGPAKLLDTAGLDEVGGLGDKKRRKALNTLKECDVAVLVVDTDTAAAAIKSGR
C. acetobutylicum    SN---------VKGTTTDPVYKA-MELLPLGPVMLIDTAGLDDISDLGELRRGKTLEVLSKTDVAILVFDVESGITEYDKNI
C. perfringens       SD---------FKGTTTDPVYKA-MELLPLGPVFVDTAGFDDEGEIGKLRVEKTEEVVGKTDVALITLSLSEILEAIKSNI
C. thermocellum      SD---------VKGTTTNPVYKA-MELLPLGPVVIIDTPGIDKGTLGEMRVKRSRQVLNKTDIAVLVIDATCGKSEDDEKL
T. maritima          SE---------YAGTTTDPVYKS-MELYPVGPVTLVDTPGLDDVGELGRLRVEKARRVEYRADCGILVTDSEPTPYEDDVVN
B. thetaiotaomicron  SD---------TPGTTTDSVQKA-MEIHGIGPCLFIDTPGFDDEGELGNRRIERTWKAVERTDIALLLCAGGGSAEETGEPD
C. tetani            SN---------VAGTTTDPVYKA-MELFPIGPIMLIDTAGLDDEGYIGNLRIEKTKEIMNKTDIAVIAIDCKNENFEYEMYL
D. desulfuricans     KADPVLVSDLISEGDTVLCVV-----------------------------------------------------------
S. oneidensis        SD---------IKGTTTDAVAKA-YELQPLGPVTFYDTAGIDDEGTLGAMRVSATRRVLFRSDMALLVVDEQGLCPSDMALI C. reinhardtii       LAEALEWESKVMEQAHKYNVSPVLLLNVKSRGLPEAQAASMLEAVAGMLDPSKQIPRMSLDLASTPLHERSTITSAFVKEGA
C. acetobutylicum    YSLLLEKKIPLIGVLNKIDKKDYKLEDYTSQFKIPIVPISALNNKGINNLKDELIRLAPENDDKFKIVGDLLSPGDIAVLVT
C. perfringens       EFKDMLSKEILWLNKLKKAKKPAILVINKCDLVPNKLIESKIDLKDIDKTTLSNKDCFVDSNLMNSLKEIGELLGIPCVAIS
C. thermocellum      IELFEKKDIKYVVVYNKADLEGHEETVGDNEIYVSAKTGYNINKLKEKIASLAVTDDDITHKIVGDLISPSDFVVLVV-----
T. maritima          LFKEMEIPFVVVVNKIDVLGEKAEEELKGLYESRYEAKVLLVSALQKKGFDDIGKTISEILPGDEEIPYLGDLIDGGDLVILV
B. thetaiotaomicron  FTEELHWLEQLKAKNIPTILLINKADIRKNTASLAIRIKETFGSQPIPFVSAKEKTGVELIRQAILEKLPEDFDQQSITGSLV
C. tetani            KEKLSKRKIPTIIALNKIDKVANLDEAIVRARKQFDNIVSISALRRENIDKLKEKIIEQVPSNNETTLLEGIVNKKDLVLLI
D. desulfuricans     ---------------------------------------------------------------------------------
S. oneidensis        DEIRQLQMPILMVFNKADICTPKAEDIAFCQNQSLPFIVVSAATGLAGKQLKQLMVELAPAEYKQEPLLAGDLYQAGDVILC C. reinhardtii       VRSSRYGAPLPGCLPRWSLGRNARLLMVIPMDAETPGGRLLRPQAQVMEEAIRHWATVLSVRLDLDAARGKLG-EEACEMER
C. acetobutylicum    -----------------------------------------------------------PIDKAAPKGRLIIEQQTI-R
C. perfringens       AKNNLNINELKKELVNVSPSSITESPIIGDKIKAGDKILLVA-----------------PQDICAPKGRLIIEQVQVL-R
C. thermocellum      -----------------------------------------------------------PIDKAAPKGRLIIEQQTI-R
T. maritima          V----------------------------------------------------------PIDLGAPKGRLIMEQVHAI-R
B. thetaiotaomicron  TEGDLVLLVM-------------------------------------------------PQDICAPKGRLIIEQVQTM-R
C. tetani            T----------------------------------------------------------PQDLCAPKGRLIIEQVQVL-R
D. desulfuricans     -----------------------------------------------------------PIDLAAPKGRLIIEQVQVL-R
S. oneidensis        VV---------------------------------------------------------PIDMAAPKGRLIIEQVQLL-R C. reinhardtii       QRFDGVIAMMERN-----------DGEPTLVVTDSQAIDVVHPWTLDRSSGRPLVPITIFSTAMAYQQNGGRLDPFVEGLEA
C. acetobutylicum    DILESDAIAMVTKEFELRETLDSLRKKPKIVITDSQVFLKVAADTPKDIL------MTSFSTLLMARH--KGDLIELARGARA
C. perfringens       DILDYGCIPTMVTLDKLDEGLRIFNGKPDLVITDSQVFKQVNAKLDRSVP------VHNCSGKDFYSCAKA
C. thermocellum      DILESDAVAIVVKENELKNTLDSLCKKPKLVITDSQAFEHVAADTPDDIY------LTSFSTILFARY--KCNLEIAVKCAKT
T. maritima          EALDREAIALVVKERELRYVMENICMKPKLVITDSQVVMKVASDVPEDVE------ITTFSIVESRY--KGDLAYFVESVRK
B. thetaiotaomicron  ELLDKKCLIMSCTTDKLQETLQALSRPPKLITDSQVFKTVYFQKPEESR------LTSFSVLFACY--KGDIRYYVKSASA
C. tetani            DILDKGAMAMVLKDTELQEGLKNLYKKPDLVITDSQIFNKVKDIIPRDIK------LTSFSVLMARY--KGDIRLLIEGAKS
D. desulfuricans     DVLDADAMGMVVKEREELEAALDKLVSPPALVITDSQVVLKVAGDVDDDIP------MTTFSTLFARY--KGDLELLVRCARA
S. oneidensis        EALDRSAIAMVVKETELAQALSV--VTPKLVISDACAIKQVAAIVPDAVP------LTTFSTLFARF--KCDLAALATCADA C. reinhardtii       LETLQDGDRVLISFACNFNRITSACNDTGMVQIPNKLEAALGKKKLQIEHAFCREFPELESGGMDGLKTAIHCGGCMIDAQK
C. acetobutylicum    IEDLKDGDKILIAEACTHRQSD---DIGKVKIPRWLRQKTGKKLE-FDFSSCFSFPPNI----EDYALIVHCAGCMLNRRS
C. perfringens       TKNIKAGDKVLIAEACTEHQLKG---DTAREKLPTWLEEETCPGII--VHNCSGKDFPKNI----NFYALIVHCGGCMFNKAE
C. thermocellum      LDSLQDCDTVLISEQCTHRQCD---DIGTVKLPRWINNYTKKNLN-FEFTSCTEFPEDI----TRYKLIVHCGGCMLNERE
T. maritima          TEFILFGDTVVIMPCCTERPLTE---DTGRVKIPRWLVNHTGAQLN--EKVIAGKDEPDLEEI--EGAKLIIHCGGCVILNRAA
B. thetaiotaomicron  IGSLTESSRVLIAPACLEAPLSE---DIGRVKIPHLLRKKRIGEKLS--IDIVAGTDEPQDI----TPYSLVIHCGACMENRKY
C. tetani            INNLKPGDNILISEACPHESLKG---DTAKEKFIPNLLKKKIGGEVN--IDFSSGEDFTKNI----EKYKLIIVHCGGCMLNQKQ
D. desulfuricans     LDSLRDGDTVLMCEACSEHAVAD---DIGRVKIPRWITQYTGRELS--EEMYAGKDFPEDI----ERYALIAVHCGGCMTNRAE
S. oneidensis        LDTLQDGDKVLISEACSENVQED---DTGRVKIPRWINSYTGKQLE-EVVTSGHDFPNDL----EQYALIVHCGACMENRNE C. reinhardtii       MQQRMKDLHEAGVEVINNGVFFSWAAWPDALRRALEPWGVEPPVGTPATPAAAPATAASGV*
C. acetobutylicum    MLHRIESSVKKQLPLVNNGVLIAYVQGILP--RALKPFPYADRIFNQSSRN*
C. perfringens       IMNRLGICDDALVEITNEGTSIAEINNILD--RVMEPLK*
C. thermocellum      MKYRYKCAVEQNVEITNNGILIAYVHGILK--RSLQIFPDILAEIL*
T. maritima          MMRRVRMAKRLGLEMINGVTISYLHGVLD--RAIRPFREEVKV*
B. thetaiotaomicron  VLSRIERARLQNVEMTNNGVAIAFLNGILN--QIEY*
C. tetani            MINRLNKANEKNLEITNIGVALAYLNGLLK--RVSEMF*
D. desulfuricans     MMRRIRECTRRGVEVTNNGVAISKVQGVLE--RVVAPFGL*
S. oneidensis        MLRRIRECQRRGVEITNNGVAISKLQGVLP--RVLTPFNRNPQQ*
```

Figure 6C

HydG

```
C. reinhardtii       MSVPLQCNAGRLLAGQRPCGVRARLNRRVCVPVTAHGKASATREYAGDFLPGTTISHAWSVERETHERYRNPAEWINEAAIH
T. maritima          --------------------------------------------------------------------------------M
C. thermocellum      ------------------------------------------------------------------------MCRYKVC
C. tetani            ----------------------------------------------------------------------------MIC
D. desulfuricans     --------------------------------------------------------------------------------
S. oneidensis        -----------------------------------------------------------------------------MSTHE
B. thetaiotaomicron  --------------------------------------------------------------------------------
C. perfringens       --------------------------------------------------------------------------------
C. acetobutylicum    --------------------------------------------------------------------------------

C. reinhardtii       KALETSKADAQDAGRVREILAKAKEKAFVTEHAPVNAES--KSEFVQGLTLEECATTINVDSNNVELMNEIFDTALAIKERI
T. maritima          CMYVFVKERVESRSFIPEEKIFELLEKTKNPDPARVREIIQKSLDKNRLEPEETAITLNVE-DP-ELLEEIEEAARTLKERI
C. thermocellum      KLKVGDIQMVEKVDFIKEDLIFSLLEKGKITDRNEIREILAKARECKGISLGEVAKILYLE-DE-ELLEELYDVAKYIKNKI
C. tetani            KMKEIKKMKAEEFIIHSDIEKALDKGREKAKNKDYVRELLNKALECKGLTYEEGAVILNVE-DE-HILEDIYKAAKIIKERI
D. desulfuricans     ----MSFDSRSLPGFIDEEKIESVIAATAKPDAVRVREILAKAREAKGLDAEETATTLQLD-NE-ELDAELFATAKKVKQTI
S. oneidensis        HHSITLSDYNPNVNFIDDKAIWQTIEDASDPSREQVLAILDKARQCEGLSISETALILQNQ-DK-TLDEMLFSVABEIKNTI
B. thetaiotaomicron  -MYKVDSPQAEEFIHHEEILETLEYAWSHEKDNRAFIEQLIEKAALCKGLTHREAAITLECD-QP-DLIERIFELAKEIKQKF
C. perfringens       MLKDNEKYNALDFIKDDEINSLIAKGKELVSDKELVREIIEKSKSAEGLTPEETAVLLNLE-DK-ELIEEMFKAAARQVKEKL
C. acetobutylicum    -MYNVKSKVATEFISDERIIDSLEYAKQNKSNRELLDSIIEKAKECKGLTHRDAAVILECQ-IE-GENEKMEKIARFIKQKF C. reinhardtii       YGNRVVLFAPLYIANHQNNTCTYCAFRSANKGMERSILTDDDLREEVAALQRQGHKRILALTGEHPFKYTFDNFLHAVNVIAS
T. maritima          YGNRIVLFAPLYIGNDCINDCYYCGFRVSNKVVHERTLTHEQLKFEVKALVSQGHKRLIVVYGEHPNYSPEFIARTIDIVYN
C. thermocellum      YGKRVVLFAPLYTSNECDNNCLYCGFRHDNKELHEKTLSLEEIVEBEAKAIERQGHKRLLLICGEDPRKTNVKEFTDAMEAIY
C. tetani            YGKREVLFAPLYISSYCVNNCKYCGYKCSNNTFKRNKLTMDEIABEVKILESLGHKRLALEVGEDDVNCSIDYVLKSIKKIY
D. desulfuricans     YGNRLVLFAPLYITNECYNRCAYCGFNATNSDLKERTLSEDEIRAEVEVLERLGHKRLLVYGEHPRLDADWMARTIQVVYD
S. oneidensis        YCNREVMFAPLYVSNHCANSCSYCCFNADNHELKERTLKQDEIRQEVAILEEMGHKRIILAVYGEHPRNNVQAIVESIQTMYS
B. thetaiotaomicron  YGNRRVMFAPLLSNYCVNGCVYCPYHAKNKTIAERKLTQEEIRKEVIALQDMGHKRLALEAGEHPTLNSLEYILESIRTIY
C. perfringens       YGKRLVVFAPLYVSNYCVNNCTYCGYKHCNDELKEKKLNKEQLIEEVKVLESLGHKRIALEAGEDPVNAPLDYILDCIKSIY
C. acetobutylicum    YGNRIVMFAPLYLSNYCVNGCVYCPYHHKNKHIARKKLSQEDVKRETIALQDMGHKRLALEAGEDPVNNPIEYILDCIKTIY C. reinhardtii       VKTEPEGSIRRINVEIPPLSVSDMRRLKNTDSVGITVLFQETYHRDTFKVMFPSGEKGDFDFRVLTQDRAMRAGLDDVGIGA
T. maritima          IKY-CNGEIRRIVNVNAAPQTIEGYKIIKS-VGIGIFQCEQETYHRETYLKEPRCEKSNYNWRLYGLLRAMMACIDLVGVGA
C. thermocellum      KSTD----IRRINVEAAPMTVDDYRELKK-AGIGTCVIFQETMHRETYRIMEPVGKKANYDWRITAIDRAFEGGIDDVGVGA
C. tetani            SLKFNNGSIRRINVNIAATTIENYKKLKE-AEIGTYILFQETYHKETYEKMEPTCEKSDYNYHTTAMLERARMAGIDDVGIGV
D. desulfuricans     IVSEKSGFIRRIVNINCAPQTVDGFRKGHD-VGIGITYCCEQETYMKATYDKALGGEKKDYLWRIGYAMHRAMEAGIDLVGMGP
S. oneidensis        VKQGKGGEIRRINVNCAPMSVEDFKQLKT-AAIGTYCCFQETYHQDTYSQVELKCGKKTDFLYRLYAMHRAMEACIDLVGIGA
B. thetaiotaomicron  SIRHKNGAIRRINVNIAATTENYKRLKD-AGIGTYILFQETYMKKNYEALEFTCEKSNYAYHTEAMDRAMEGGIDDVGVGV
C. perfringens       SIKFDNGSIRRINVNIAATTVENYKRLKD-AEIGTYILFQETYMKPTYEKLEVSGEKHNYNYHTTAMHRAREAGIDDVGMGV
C. acetobutylicum    SIKHKNGAIRRVNVNIAATTVENYKKLKD-AGIGTYILFQETYNKKSYEELEPTCEKHDYAYHTEAMDRAMECGIDDVGIGV C. reinhardtii       LFGLYDYRYEVCAMLMESEHLDREYNAGPHTISVPRMPEADGSELSIAPPYPVNDADFMKLVAVIRIAVPYTGMILSTRESP
T. maritima          LEGLYDWKFEVMGLLYFIHEDERFGVGPHTISFPRIKEAINTPYSQKPEHVVSDEDFKKLVAILRLSVPYTGMILTAREFA
C. thermocellum      LFGLYDYRFEVLGLLMECMHFEEKYGVGPHTISVPRLREALGAPLKEIPYKVTDKD-FKKIVAIIRIAIDRAFEGGIILSTRERA
C. tetani            LYGLYDYKYFVTVAMLMECERLEKATGVGPHTISVPRLREVGMTLKLEPAENVSLENYPYLVDDED-FKKIVAILRLSVPYTGVILSTREEA
D. desulfuricans     ILGLYDYRFELLALMCHAADLEKHEGVGPHTISFPRLEEALNADMAFNEPHPLTDSQEFKRMVAVIRLAVPYTGMILSTRENA
S. oneidensis        LFGLYDHRFELLAMLTHVCQDLEKDCGVGPHTISFPRIEDAHGSAISEKPPYEVDDDCFKRIVAILRLAVPYTGCIMSTRESA
B. thetaiotaomicron  LEGLNTYRYDFVGLLMFAEHLEARFGVGPHTISVPRICSADDIDAGDFPNAISDDI-ESKIVAVIRIAVPYTGIISTRESQ
C. perfringens       LYGLYDYKYFTLAMLMEAMDLEFTTGVGPHTISVPRLREAENVSLENYPYLVDDED-FKKIVAYAGILLSTREEP
C. acetobutylicum    LFGLNMYKYDFVGLLMFAEBHLEAAMGVGPHTISVPRIREADDIDPENFSNAISDEI-FEKIVAIIRIAVPYTGMIVSTRESK C. reinhardtii       EMRSALLKCEMSQMSAGSRTDVGAY-HKDHTLSTEANLSKLAGQFTLQDERPTNEIVKWLMEE-GYVPSWCTACYRQGRTGE
T. maritima          KLRDEVIKICVSQIDAGSRIGICAYSHKEDDEDRK-------RQFTLEDPRPLDQVMRSLLKE-CFVPSECTACYRACRTGE
C. thermocellum      EERDELLSVGVSQISAGSKTNPCGYQEDDDHA----------DQFEISDNRSLPKVMETICQQ-GYIPSECTACYRRCRTGE
C. tetani            DFREKVIALGVSQISAGSCTGVCGYSKENNIKHKDEK-----PQFELGDNRSPIEVIKSICKS-GYIPSYCTACYREGRTGE
D. desulfuricans     AMRRELLELGVSQISAGSRTYPCAYSDPSYDRPDV-------QQFCVGDSRSLDEVAELVSL-GYIPSYCTACYRLGRTGE
S. oneidensis        AIRKELLELGVSQISAGSRTAPCGYQDSKCNQHDA-------EQFSLGDHREMDEIIYELVTDSDAIPSECTACYRKGRTGD
B. thetaiotaomicron  ESREKVLELGISQISGGSRTSVCGYAETELPEDNS-------AQFDVSDTRTLDEVVNWLLES-GYIPSTCTACYREGRTGD
C. perfringens       GLRDEIIALGVSQVSTGSCTGVCGYSESYIDPEEK-------PQFEVDDHRSPVEMIESLMEA-GFIPSYCTACYREGRTGD
C. acetobutylicum    KTRERVLELGISQVEMGSSTSVCGYVESEPEEDNS-------SQFEVNDNRTLDEIVNWLLEM-NYIPSTCTACYREGRTGD C. reinhardtii       DFMNICKAGDIHDFCHPNSLITLQEYIMDYADPQLRKKGEQVIAREMGPDASEPLSAQSRKRLERKMKQVLEGEHDVYL*
T. maritima          HFMEFAIPGEVKNECTINALFILQEYLCDYATEETRKVGEEVHERELQKMNPKIRERVREGLEKIKR-----GERDVRF*
C. thermocellum      HFMEYAKAGDIHEECCPNAILTFKENLMDYADEPLRKMGEEVILKALEEIEDEKMKTLTIAKLEEIE-----KGKRDIYF*
C. tetani            RFMSLAKTGEIQNVCHFNAILTFKEFLLDYGDKEAKDLGEELIRKSLEDIPNEKIKKMTEEKLERIE-----SGERDLRF*
D. desulfuricans     HFMELAKKCFIQEFCHPNALLITFNEYLHDYASESTREACRKLIEKEAACCPENRRELVASRLQRIDG-----GERDLYI*
S. oneidensis        HFMGLAKQQFIGKECQCPNALITFKEYLNDYASEKTREAGNALIERELAKMSPSRARNVRGCLQKTD-----AGERDIYL*
B. thetaiotaomicron  RFMSLVKSGQIANCCCPNALMTLKEYLEDYASEDTRIKGMKLIAKETDRIPNPKIREIAIRNLKDIA----EGKRDFRF*
C. perfringens       RFMDIVKSGELYKICEANALITLKEFILDDYGTDRERIGDKIIKKSIDEIDNESFKKSVKEKINKIS----KCTRDLRF*
C. acetobutylicum    RFMSLVKSGQIANCCCPNALMTLKEYLEDYASSNTQKNGEALIASEVEKIPNEKVKSIVKKHLTELK----EGQRDFRF*
```

PROCESS AND GENES FOR EXPRESSION AND OVEREXPRESSION OF ACTIVE [FEFE] HYDROGENASES

This application claims the benefit of the Feb. 28, 2005 filing date of provisional application No. 60/656,957.

CONTRACTUAL ORIGIN OF THE INVENTION

The United States Government has rights in this invention pursuant to Contract No. DE-AC36-99GO10337 between the United States Department of Energy and the Midwest Research Institute.

TECHNICAL FIELD

The invention relates to the use of genes to provide expression and over-expression of any active [FeFe]-hydrogenases, expressed in any suitable host, using an [FeFe]-hydrogenase assembly of genes from a suitable organism.

BACKGROUND ART

Hydrogen has enormous potential to serve as a non-polluting fuel, thereby alleviating the environmental and political concerns associated with fossil energy utilization.

Among the most efficient $H_2$-generating catalysts known are the [FeFe]-hydrogenase enzymes found in numerous microorganisms, including the photosynthetic green alga, *Chlamydomonas reinhardtii*. The use of *Chlamydomonas reinhardtii*, also known as green algae, to produce hydrogen from water has been recognized for more than 60 years. The reaction that produces hydrogen is catalyzed by the reversible hydrogenase, an enzyme that is induced in the cells after exposure to a short period of anaerobiosis. This activity is rapidly lost as soon as light is turned on, due to immediate inactivation of the reversible hydrogenase by photosynthetically generated $O_2$ Ghirardi et al. in Biological Systems For Hydrogen Photoproduction (FY 2004 Progress Report) disclose a method for generating algal hydrogenase mutants with higher $O_2$ tolerance to function with aerobic $H_2$ production systems, which further optimize $H_2$ photoproduction using an algal production system. It generates a recombinant alga expressing an [FeFe]hydrogenase that displays increased tolerance to $O_2$ due to closure of the pathways by which $O_2$ accesses the catalytic site of the enzyme.

T. Happe et al. in Differential Regulation Of The Fe-hydrogenase During Anaerobic Adaptation In The Green Alga *Chlamydomonas reinhardtii Eur. J. Biochem.* 269, 1022-1032 (2002) disclose using the suppression subtractive hybridization (SSH) approach, wherein the differential expression of genes under anaerobiosis was analyzed. A PCR fragment with similarity to the genes of bacterial Fe-hydrogenases was isolated and used to screen an anaerobic cDNA expression library of *C. reinhardtii*. The cDNA sequence of HydA contains a 1494-bp ORF encoding a protein with an apparent molecular mass of 53.1 kDa. The transcription of the hydrogenase gene is very rapidly induced during anaerobic adaptation of the cells. The deduced amino-acid sequence corresponds to two polypeptide sequences determined by sequence analysis of the isolated native protein. The Fe-hydrogenase contains a short transit peptide of 56 amino acids, which routes the hydrogenase to the chloroplast stroma. The isolated protein belongs to the class of Fe-hydrogenases. All four cysteine residues and 12 other amino acids, which are strictly conserved in the active site (H-cluster) of Fe-hydrogenases, have been identified. The N-terminus of the *C. reinhardtii* protein is markedly truncated compared to other non algal Fe-hydrogenases. Further conserved cysteines that coordinate additional Fe—S-cluster in other Fe-hydrogenases are missing. Ferredoxin PetF, the natural electron donor, links the hydrogenase from *C. reinhardtii* to the photosynthetic electron transport chain. The hydrogenase enables the survival of the green algae under anaerobic conditions by transferring the electrons from reducing equivalents to the enzyme.

Isolation and characterization of a second [FeFe]-hydrogenase gene from the green alga, *Chlamydomonas reinhardtii*, wherein a HydA2 gene which encodes a protein of 505 amino acids that is 74% similar and 68% identical to the known HydA1 hydrogenase from *C. reinhardtii*. HydA2 contains all the conserved residues and motifs found in the catalytic core of the family of [FeFe]-hydrogenases disclosed by Forestier et al in Expression Of Two [Fe]-Hydrogenases In *Chlamydomonas reinhardtii* Under Anaerobic Conditions, *Eur. J. Biochem.* 270, 2750-2758 (2003). It is demonstrated that both the HydA1 and the HydA2 transcripts are expressed upon anaerobic induction, achieved either by neutral gas purging or by sulfur deprivation of the cultures. Further, the expression levels of both transcripts are regulated by incubation conditions, such as the length of anaerobiosis, the readdition of $O_2$, the presence of acetate, and/or the absence of nutrients such as sulfate during growth. Antibodies specific for HydA2 recognized a protein of about 49 kDa in extracts from anaerobically induced *C. reinhardtii* cells, strongly suggesting that HydA2 encodes for an expressed protein. Homology-based 3D modeling of the HydA2 hydrogenase shows that its catalytic site models well to the known structure of *Clostridium pasteurianum* CpI, including the $H_2$-gas channel. The major differences between HydA1, HydA2 and CpI are the absence of the N-terminal Fe—S centers and the existence of extra sequences in the algal enzymes.

It is disclosed that *Entamoeba histolytica* and *Spironucleus barkhanus* have genes that encode short iron-dependent hydrogenases (Fe-hydrogenases), even though these protists lack hydrogenosomes in Iron-Dependent Hydrogenases of *Entamoeba histolytica* and *Giardia lamblia*: Activity of the Recombinant Entamoebic Enzyme and Evidence for Lateral Gene Transfer *Biol. Bull.* 204: 1-9. (February 2003). A recombinant *E. histolytica* short Fe-hydrogenase was prepared and its activity is measured in vitro. A *Giardia lamblia* gene encoding a short Fe-hydrogenase was identified from shotgun genomic sequences, and RT-PCR showed that cultured entamoebas and giardias transcribe short Fe-hydrogenase mRNAs. A second *E. histolytica* gene, which encoded a long Fe-hydrogenase, was identified from shotgun genomic sequences. Phylogenetic analyses suggested that the short Fe-hydrogenase genes of *entamoeba* and diplomonads share a common ancestor, while the long Fe-hydrogenase gene of *entamoeba* appears to have been laterally transferred from a bacterium. These results are discussed in the context of competing ideas for the origins of genes encoding fermentation enzymes of these protists.

U.S. Patent Application No. 2004/02009256 discloses methods and compositions for engineering microbes to generate hydrogen. Some methods of the invention involve recoding of hydrogenase genes followed by subjecting the recoded genes to annealing-based recombination methods. The invention further provides methods of mating organisms that are transformed with recoded and recombined hydrogenase genes with other organisms containing different genome sequences.

A need exists in the art of H$_2$-generating catalysts of [FeFe]-hydrogenase enzymes, which are found in numerous microorganisms (including *C. reinhardtii*) to identify the genes essential for formation of active algal [FeFe]-hydrogenase enzymes, due to the fact that expression of an algal [FeFe] hydrogenase structural gene without the co-expression of *C. reinhardtii* genes results in the accumulation of an inactive [FeFe]-hydrogenase.

Further still, a need exists in the art of H$_2$— generating catalysts of [FeFe]-hydrogenase enzymes to provide co-expression of the *C. reinhardtii* genes and an algal [FeFe] hydrogenase structural gene in *E. coli* to produce synthesis of an active [FeFe]-hydrogenase in this bacterium, which lacks a native [FeFe]-hydrogenase.

In the art of H$_2$-generating catalysts of [FeFe]-hydrogenase enzymes, there is yet another need to demonstrate and provide a process to over-express active [FeFe]-hydrogenase in a stable, recombinant *E. coli* system, and to assemble and insert an H-cluster into *C. reinhardtii* [Fe]-hydrogenase using the *C. acetobutylicum* HydE, HydF and HydG proteins to accomplish this activation of non-cognate [FeFe]-hydrogenases—and not limit to the [FeFe]-hydrogenase assembly genes from *C. acetobutylicum*, the structural genes from *C. acetobutylicum* or *C. reinhardtii*, or use of *E. coli* as an expression host, but to accomplish the expression of any [FeFe]-hydrogenase, expressed in any suitable host, using [FeFe]-hydrogenase assembly genes from any suitable organism.

DISCLOSURE OF THE INVENTION

One object of the present invention is to identify the genes essential for formation of active algal [FeFe]-hydrogenase enzymes, given that expression of an algal [FeFe]-hydrogenase structural gene without the co-expression of *C. reinhardtii* genes results in the accumulation of an inactive [FeFe]-hydrogenase.

Another object of the present invention is to provide a process in which the co-expression of *C. reinhardtii* genes and the algal [FeFe]-hydrogenase structural gene can be used for assembly of an active algal [FeFe]-hydrogenase in *C. reinhardtii*.

An object further still of the present invention is to provide co-expression of the *C. reinhardtii* genes and an algal [FeFe]-hydrogenase structural gene in *E. coli* to produce synthesis of an active [FeFe]-hydrogenase in this bacterium, which lacks a native [Fe]-hydrogenase.

Yet another object of the present invention is to demonstrate and provide a process to over-express active [FeFe]-hydrogenase in a stable, recombinant *E. coli* system and to assemble and insert the H-cluster into *C. reinhardtii* [FeFe]-hydrogenase using the *C. acetobutylicum* HydE, HydF and HydG proteins to accomplish this activation of non-cognate [FeFe]-hydrogenases—and not limit to the [FeFe]-hydrogenase assembly genes from *C. acetobutylicum*, the structural genes from *C. acetobutylicum* or *C. reinhardtii*, or use of *E. coli* as an expression host, but to accomplish the expression of any [FeFe]-hydrogenase, expressed in any suitable host, using [FeFe]-hydrogenase assembly genes from any suitable organism.

BRIEF DESCRIPTION OF THE DRAWINGS

FIG. 3 shows putative homologues of *C. reinhardtii* HydA1, HydEF (both the HydE and HydF domains, respectively) and HydG found in organisms with sequenced genomes. The gene identification, percent identical amino acids (% I), E values, homology length and homology rank to the *C. reinhardtii* proteins are shown. Organization of the respective genes within the genomes of the organism is also included.

FIG. 6 Shows alignments of *C. reinhardtii* (A and B) HydEF and (C) HydG amino acid sequences with the corresponding putative homologues found in other organisms. The amino acid sequences were derived from the *C. reinhardtii* cDNAs. Regions of identical amino acids are shown in black, and regions of similar amino acids are shaded in gray. Shown in (A and B) are HydE homologues followed by the *C. reinhardtii* linker region, and lastly by HydF homologues. Organisms shown in the alignment include: *Thermotoga maritima, Clostridium thermocellum, Clostridium tetani, Desulfovibrio desulfuricans, Shewanella oneidensis, Bacteroides thetaiotaomicron, Clostridium perfringens* and *Clostridium acetobutylicum*.

BEST MODE FOR CARRYING OUT THE INVENTION

Experimental Procedures Strains

Figure 1:
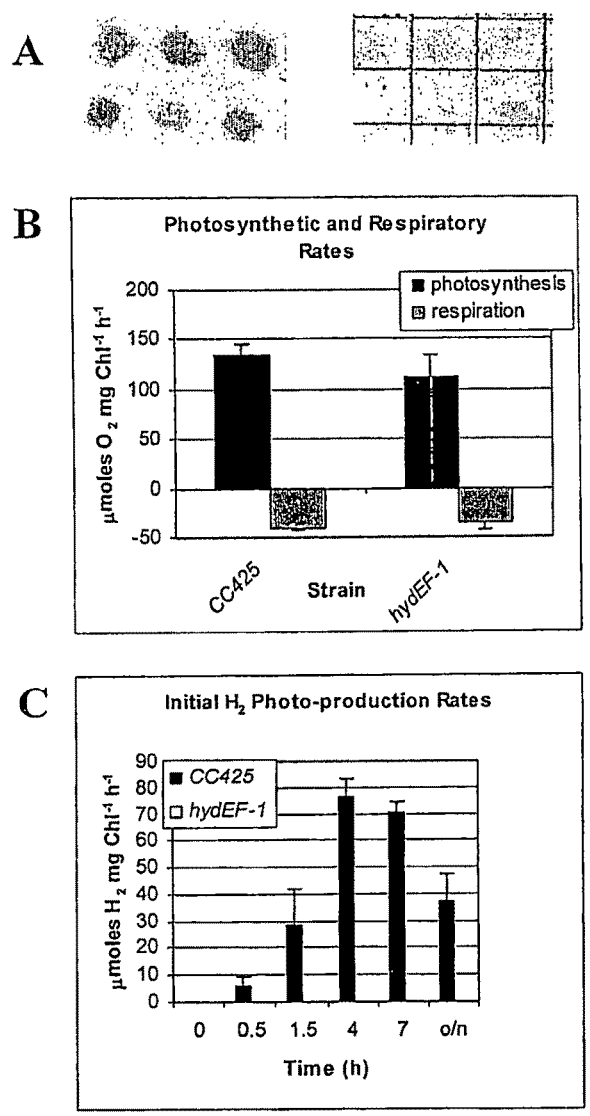
FIG. 1 shows initial characterization of the *C. reinhardtii* hydEF-1 mutant, wherein (A) colonies of *C. reinhardtii* insertional mutants growing on TAP agar plates (left) and photo-production of H$_2$, following anaerobic induction, detected visually on the chemochromic sensor (right) as a dark blue spot. Colony four (bottom, left) failed to produce sufficient H$_2$ for colorimetric detection; (B) shows rates of algal photosynthesis and respiration; and (C) shows initial rates of H$_2$ photo-production from cultures anaerobically-induced in the dark. Only the WT produced H$_2$.

An insertional mutagenesis library was generated by transforming *C. reinhardtii* strain CC425 (cw15, sr-u-60, arg7-8, mt+) with the pJD67 plasmid (Davies, J. P. et al. [1999] Plant Cell 11, 1179-1190) provided by Professor Anastasios Melis (University of California, Berkeley, Calif.).
Hydrogen and Oxygen Assays Chemochromic screening was performed using colonies growing on Tris-acetate-phosphate (TAP) agar plates. Hydrogenase activity was induced anaerobically in the dark, and $H_2$ photo-production was monitored the following day. Rates of photosynthesis, respiration and $H_2$ photoproduction in liquid cultures were determined (M. Forestier et al. [2003] *Eur. J. Biochem.* 270, 2750-2758).

Hydrogen was assayed from the headspace of anaerobically-sealed cultures using a Varian model 3700 gas chromatograph (GC). For the methyl viologen (MV) assay of hydrogenase activity, cells were removed and added to an equal volume of anaerobic 2×MV solution (100 mM MV (oxidized), 50 mM Tris, pH 8.0 and 0.2% Triton X-100) in a sealed anaerobic vial. Degassed sodium dithionite was added to a final concentration of 4 mM to initiate $H_2$ production from reduced MV.
Anaerobic Induction of Liquid Cell Suspensions

*C. reinhardtii* cultures were grown on TAP medium to ~20 µg/ml total chlorophyll, centrifuged at 2500 g for 5 minutes and resuspended in ¹/₁₀th volume of induction buffer (AIB), containing 50 mM potassium phosphate pH 7.0 and 3 mM $MgCl_2$ [27]. Samples were placed in vials that were wrapped with aluminum foil to exclude light, sealed with a rubber septum, flushed with argon for 15 minutes and incubated anaerobically in the dark at room temperature.
Southern and Northern Blot Analysis Southern blotting experiments were performed using standard methodology. Genomic DNA was extracted and purified using a DNeasy Plant Mini Kit (Qiagen). Northern blot analysis was performed using 10 µg of total RNA for each sample as previously described. Probes were labeled using $\alpha$-$^{32}$dCTP (ICN) and the rediprime II DNA random-prime labeling system (Amersham Pharmacia Biotech).
Western Blot Analysis After four hours of anaerobic induction, cells were lysed under anaerobic conditions. Aerobic control samples were lysed immediately after resuspension in AIB. Cells were disrupted with gentle rocking in lysis buffer (50 mM Tris, pH 8.5, and 0.25% Triton X-100) for thirty minutes, and the cellular extract was centrifuged for 10 minutes at 10,000 g. The hydrogenase protein was partially purified from induced and non-induced cells under strictly anaerobic conditions by loading the lysed supernatant, containing the hydrogenase activity, onto a Q-sepharose fast-flow column (Pharmacia). The column was washed once with 2 column volumes of wash buffer (50 mM Tris, pH 8.5, 100 mM KCl) and eluted with two column volumes of elution buffer (50 mM Tris, pH8.5, 250 mM KCl). Approximately 85% of the hydrogenase activity detected in the crude lysate from induced WT cultures was recovered in the partially purified fraction. Protein samples were concentrated using an Amicon protein-concentration cell and a YM10 membrane. Equal amounts of protein ($A_{280}$) were loaded and separated using standard SDS-PAGE methodologies. Western blotting was performed using a BioRad Mini-Protean III electrophoresis and blotting apparatus. The primary hydrogenase antibody was derived from a synthetic peptide (DKAKRQAALYNL) containing a sequence common to both the HydA1 and HydA2 proteins and was generated commercially in rabbits (Sigma GenoSys). The secondary antibody was obtained commercially as an alkaline phosphatase conjugate (BioRad), and standard chemochromic detection techniques were utilized for hydrogenase detection.
Gene Identification DNA regions flanking the insertion site of pJD67 were determined using genome walking. DNA downstream of the insertion site was amplified using the PCR methods outlined in the Universal GenomeWalker Kit and in the Advantage-GC Genomic PCR mix, both from Clontech. Coding sequences for both the HydEF and HydG proteins were obtained by sequencing the cDNA corresponding to both genes. The cDNA constructs were obtained from the Kazusa DNA Research Institute (http://www.kazusa.or.jp/). All DNA products were sequenced by the University of California, Davis.
Complementation A BAC clone containing the HydEF and HydG genes was obtained from the Clemson University Genetics center. The genomic HydEF gene was obtained by KpnI digestion of the BAC clone, and the insert, containing the full-length HydEF gene with promoter and termination sequences, was cloned into the KpnI site of pSP124S (from Saul Purton, University College, London). The resulting plasmid, pMP101, contains the HydEF gene and the Ble$^r$ gene used for antibiotic selection. The pMP101 plasmid was linearized by digestion with SwaI and transformed into the hydEF-1 mutant using the glass bead method of Kindle (K. L. Kindle [1990] *Proc. Natl. Acad. Sci. USA* 87, 1228-1232). Controls, using cells only or 1 µg of pSP124S (V. Lumbreras et al. *Plant j.*, 441-448), were also used.

Heterologous Expression and Purification

Expression of active *C. reinhardtii* HydA1 was achieved by cloning the HydEF and HydG cDNA constructs into *E. coli* expression plasmids driven by the T7 promoter. The two genes were cloned into the pACYC Duet expression plasmid (Novagen). Additional control plasmids containing only the HydEF or HydG genes were also cloned into the pACYC plasmid. The *C. reinhardtii* HydA1 gene was cloned into pETBlue-1, and a Strep-Tactin affinity tag (Strep-Tag II) was added to its C-terminus for affinity purification of HydA1. Plasmids were co-transformed into *E. coli* B1-21 (DE3) cells (Novagen). The presence of appropriate plasmids was verified by restriction analysis and sequencing. Expression and purification of tagged HydA1 was done as follows: An inoculum from an overnight culture of transformed BL21 (DE3) was grown in L-broth containing appropriate antibiotics. Cells were grown until the $OD_{600}$ reached 0.5-0.7, and isopropyl-beta-D-thiogalactopyranoside (IPTG) (Novagen) was added to 1.0 mM. After a 1-h aerobic induction, cultures were made anaerobic by purging with argon for five hours. Cells were harvested, then disrupted on ice by sonication. HydA1-StrepTag II was purified using Strep-Tactin Sepharose (IBA) and assayed for hydrogenase activity using MV.

Expression Cloning of *C. acetobutylicum* HydA, HydE, HydF and HydG—

The *C. acetobutylicum* Hyd genes were isolated from purified genomic DNA (strain ATCC 824) by PCR amplification. Gene specific primers were based on the known sequence of HydA (Genbank accession no. AAB03723) (19, 20), and the sequences of HydE (Genbank accession no. CAC1631), HydF (Genbank accession no. CAC1651), HydG (Genbank accession no. CAC1356) and HydB (Genbank accession no. CAC3230) identified by tBLASTn homology searches of the *C. acetobutylicum* genome at NCBI using the *C. reinhardtii* HydEF, HydG and HydA2 peptide sequences. Gene-specific primers were designed to match the ends of each Hyd gene (IDT Technologies), and also to contain a suitable restriction site for expression cloning. Approximately 20 μg of genomic DNA were digested overnight with BamHI, and 200 ng were used as a template for PCR amplification reactions performed with KOD polymerase (Novagen). PCR fragments were gel purified, digested overnight with restriction enzymes and sub-cloned into the dual multiple cloning sites (MCS) of either plasmid pCDFDuet-1 (Novagen) (HydF and HydG) to form pCaFG, or pETDuet-1 (Novagen) (HydA Or HydB and HydE) to form pCaAE and 8pCaBE. The StrepII-tag sequence WSHPQFEK was added to the C-terminal end of [FeFe]-hydrogenase structural genes, HydA and HydB, during PCR amplification. The sequence and reading frame of each gene were confirmed by DNA sequencing (Davis Sequencing, LLC).

Expression Cloning of Other [FeFe]-Hydrogenase Genes

The [FeFe]-hydrogenase structural genes from *C. reinhardtii*, and *Clostridium pasteurianum* were cloned from purified genomic DNA as follows. To clone *C. pasteurianum* HydA, the ATCC strain 6013 was cultured anaerobically on reinforced clostridial media, and the genomic DNA was purified using the Qiagen DNAeasy Tissue Kit (Qiagen). Purified DNA (500 ng) was digested overnight with BamHI, and 100 ng were used in a PCR reaction with HydA specific oligonucleotides that contained a 5'-NcoI and 3'-BamHI site for in-frame cloning. Gene fragments were gel purified, digested with NcoI and BamHI, and cloned into MCS1 of pCaE2 to generate pCpIE.

The *C. reinhardtii* HydA1 and HydA2 cDNA's clones were used as templates for PCR amplification with oligonucleotides designed with 5'- and 3'-end restriction sites as described above. A StrepII-tag sequence WSHPQFEK was added to the 5'-end oligonucleotide of HydA1, and to the 3'-end oligonucleotide of HydA2. Gene fragments were isolated by gel electrophoresis, digested, and sub-cloned into MCS site 2 of pCaE1 (pETDuet-1 with HydE at MCS site 1) to form pECr1 (HydA1), and pECr2 (HydA2). The reading frames and gene sequences were confirmed by DNA sequencing.

[FeFe]-Hydrogenase Expression in *E. coli*—

For expression testing of constructs, plasmids that harbored a complete set of T7 regulated Hyd genes were co-transformed into the *E. coli* strain BL21 (DE3) (Novagen) with co-selection for $Ap_r$ (pETDuet-1 clones), and $Sm_r$ (pCDFDuet clones). Transformed cells were grown overnight in LB media (Sigma) plus antibiotics, and the next day were sub-cultured (1:50 dilution) into 115 ml of fresh LB media supplemented with antibiotics, and 100 μM Fe-Citrate. Cultures were grown aerobically at 37° C. on a rotary shaker at 250 rpm to an $OD_{600}$ of 0.5-0.7. Isopropyl-beta-D-thiogalactopyranoside (IPTG) (Novagen) was added to a final concentration of 1.5 mM, and cultures shaken at room temperature at ~100 rpm to allow for pre-induction of Hyd expression prior to anaerobic induction. After 1 h, the cultures were transferred to a 120 ml serum vial, sealed with rubber septa, and sparged with argon at room temperature for a period of 3-5 h to achieve anaerobic conditions and induction of [FeFe]-hydrogenase biosynthesis. The expression of [FeFe]-hydrogenases for affinity purification was performed in minimal media. Transformed cells were cultured overnight in 5 ml of M63, supplemented with 0.5% glucose, 0.4% casein-hydrolysate, 100 ∝M Fe-citrate, 300 ∝cg/ml ampicillin, and 50 ∝g/ml streptomycin. Overnight-grown cultures were diluted 1:50 into 25 ml of fresh media, grown at 37° C. until the $OD_{600}$ reached 0.5 and used to inoculate 1 L of M63 (without Fe-citrate). The 1 L culture was grown at 37° C. to an $OD_{600}$ of 0.5. A 1 M solution of Fe-citrate was added to a final concentration of 100 μM, and the cultures incubated an additional 10 min at 37° C. IPTG (1.5 mM) was added and the cultures shaken at 100 rpm for 1 h at room temperature. Following the initial induction period, the cultures were transferred to a sealed 1 L flask and sparged with argon at room temperature overnight to induce biosynthesis of [FeFe]-hydrogenase.

Purification of Recombinant, StrepII-Tagged [FeFe]-Hydrogenases—

Purification steps were performed under anaerobic conditions. Cells expressing StrepII-tagged [FeFe]-hydrogenases, were collected by centrifugation at 6000×g for 10 minutes. The cell pellet was resuspended in break buffer (BB) (150 mM Tris-HCl pH 8.0, 100 mM NaCl, 1 mM DTT, 1 mM Na-dithionite, 100 μM PMSF, 5% glycerol), and broken in a French press. Avidin was added at 3 nM to block binding of biotin and biotinylated proteins. The disrupted cell suspensions were centrifuged at 19,000×g for 30 min to pellet cell debris. The clarified crude extracts were passed over a Strep-tactin-Sepharose (IBA) affinity column, pre-equilibrated with buffer BB. Columns were washed with 3-5 column volumes of ice-cold BB, and the StrepII-tagged hydrogenases were eluted in BB containing 2.5 mM desthiobiotin.

SDS-PAGE and Western Blots of Heterologously-Expressed Proteins

For SDS-PAGE, protein samples were diluted in 1× SDS-PAGE loading buffer (Novagen), boiled for 10 min and cooled on ice. Samples were loaded onto a 12% SDS gel and run at 45 mA for 2 hours. Following electrophoresis, proteins were blotted onto PVDF membranes and detected using a streptactin-alkaline phosphatase conjugate detection kit (IBA).

[FeFe]-Hydrogenase Activity Assays—

Activities of purified [FeFe]-hydrogenases or of whole cell extracts were routinely measured as the production of $H_2$ gas from reduced methyl viologen (MV). Activity assays of whole cells were performed in argon flushed, 13.5 ml sealed serum vials that contained 1 ml of an anaerobically prepared, 2× whole-cell reaction buffer (50 mM potassium phosphate, pH 7; 10 mM methyl viologen; 20 mM sodium dithionite; 6 mM NaOH; 0.2% Triton X-100) and 1 ml of cells. Assays of purified enzymes were performed on aliquots (25-50 □l) diluted to 1 ml in anaerobically prepared BB buffer in an argon flushed vial that also contained 1 ml of an anaerobically prepared, 2× enzyme-reaction buffer (50 mM potassium phosphate, pH 7; 10 mM methyl viologen; 20 mM sodium dithionite; 6 mM NaOH). All reactions were incubated at 37 □C. After incubation, 400 □l of headspace gas was removed with a gas-tight syringe and $H_2$ levels measured by gas chromatography (Hewlett Packard, 5820).

Results

Mutant Characterization

In *C. reinhardtii*, two [FeFe]-hydrogenase enzymes, HydA1 and HydA2, are known. In order to identify genes required for expression and activity of these enzymes, we used chemochromic $H_2$ sensors[4] to screen a random insertional mutagenesis library for clones incapable of photo-producing $H_2$ following the required anaerobic induction. Mutants were generated by transforming the Arg7 gene into *C. reinhardtii* strain CC425, which is an arginine auxotroph. The Arg7 gene is randomly incorporated into the *C. reinhardtii* genome and disrupts small sections of wild-type (WT) genomic DNA. The mutant hydEF-1 was identified by its inability to produce detectable quantities of $H_2$ as shown in FIG. 1A. The dark blue spots observed for the other five colonies from the same library are indicative of WT $H_2$-production capacity.

The mutant hydEF-1 grew on minimal medium agar plates with $CO_2$ as the sole carbon source, thereby demonstrating that the cells were photosynthetically competent. Furthermore, photosynthetic and respiratory rates of both the parental and hydEF-1 strains were measured in liquid media using a Clark-type electrode (FIG. 1B). Compared to the WT, the hydEF-1 mutant exhibited normal rates of respiration and photosynthetic $O_2$ evolution. This demonstrates that the lack of $H_2$ photo-production activity in hydEF-1 is not the consequence of a secondary metabolic, or photosynthetic electron transport defect, but rather is specific to the hydrogenase enzyme.

Hydrogenase activity in *C. reinhardtii* is induced by anaerobiosis achieved either in the dark by using an inert gas (or exogenous reductant) to purge $O_2$ from sealed cultures or in the light by depriving sealed cultures of sulfur, which results in attenuated rates of photosynthetic $O_2$ evolution. Hydrogen production, following dark anaerobic induction, was monitored from WT and hydEF-1 mutant cultures using several techniques: (1) initial rates of $H_2$ photo-production (FIG. 1C) were assayed using a Clark-type electrode, (2) hydrogenase activity mediated by reduced MV was detected by GC, and (3) fermentative $H_2$ production was assayed by GC analysis. In contrast to WT cultures, $H_2$ production was not detected from hydEF-1 mutant cultures by any of these assays. Moreover, hydEF-1 mutant cultures that were induced anaerobically in the light, under conditions of sulfur deprivation, failed to produce any detectable $H_2$. One-liter CC425 WT cultures consistently produced at least 70 ml of $H_2$, over the course of several days, under identical conditions. We therefore concluded that the hydEF-1 mutant is unable to synthesize an active [Fe]-hydrogenase under all of our induction and assay conditions.

Identification of the HydEF and HydG Genes

Figure 2:
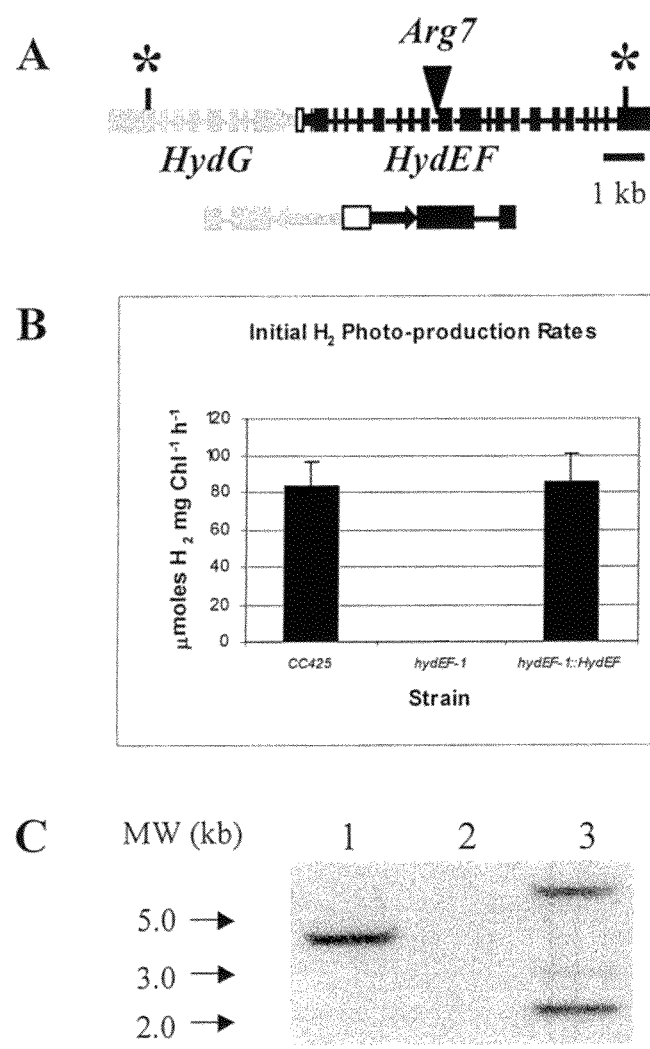
FIG. 2 shows gene disruption in the hydEF-1 mutant and complementation of the mutant phenotype; wherein (A) shows a schematic of the organization of the HydEF and HydG genes in the *C. reinhardtii* genome (top). Exons are shown as rectangles, filled gray or black for HydG and HydEF, respectively. The 5' UTRs are depicted as block arrows ending at the respective ATG start codons. Stop codons are also shown as asterisks followed by the 3' UTRs. The location of the arg7 gene insertion in HydEF is shown with the inverted triangle. The portion of the HydEF gene to the right of the triangle is deleted in the HydEF-1 mutant. The putative promoter region is shown as a white rectangle. An expanded schematic of the promoter region followed by the first two exons is shown below; (B) shows photo-production of H$_2$ measured in (1-r) the parental strain (CC425), the hydEF-1 mutant and the hydEF-1 mutant complemented with the HydEF gene (assayed four hours after dark anaerobic induction). Average deviations from the mean are indicated; and (C) shows Southern blotting of the same clones shown in (B). Genomic DNA was digested with Nco1, blotted, and probed using a DNA sequence that had been deleted in the hydEF-1 mutant.

To determine the genetic mutation responsible for the observed phenotype of the hydEF-1 mutant, we cloned and sequenced the genomic DNA flanking the mutagenizing Arg7 insert using a genome walking strategy. The gene disrupted by Arg7 insertion was determined by comparing the flanking WT sequence to the recently sequenced *C. reinhardtii* genome. The deleted gene in hydEF-1, denoted HydEF, and was shown to encode a protein with two unique domains. The N-terminal portion of the HydEF protein is homologous to a distinct group of proteins that to date are only found in prokaryotes containing [FeFe]-hydrogenases and belongs to a previously uncharacterized subset of the Radical SAM protein superfamily (H. J. Sofia et al [2001] *Nucleic Acids Res.* 1097-1106). The C-terminal portion of the HydEF protein contains a domain with predicted GTPase activity. This domain is homologous to a second distinct group of prokaryotic proteins, which are also unique to organisms that contain [FeFe]-hydrogenases. Directly adjacent to the disrupted HydEF gene in *C. reinhardtii* is a second gene, HydG, which is arranged in an order suggestive of divergent expression from the same promoter region. BLAST searches revealed that proteins homologous to HydG comprise a third set of unique proteins that also belong to the Radical SAM protein superfamily. As with HydE and HydF, the HydG homologues are only found in prokaryotes with [FeFe]-hydrogenases. The cDNAs corresponding to HydEF and HydG in *C. reinhardtii* were obtained and then sequenced to confirm the protein coding sequence of the two genes. A schematic indicating the genomic organization of the *C. reinhardtii* genes and the site of HydEF disruption is shown in FIG. 2A.

Strikingly, in the genomes of *Bacteroides thetaiotaomicron*, *Desulfovibrio vulgaris*, *Desulfovibrio desulfuricans* and *Shewanella oneidensis*, the HydE, HydF and HydG genes form putative operons with [FeFe]-hydrogenase structural genes (FIG. 3). However, the functions of HydE, HydF and HydG have not until now been assigned. As discussed below, our data indicate that these proteins are required for the assembly of active [FeFe]-hydrogenase, and therefore, we have named the *C. reinhardtii* genes, HydEF and HydG, according to the suggested hydrogenase nomenclature (P. M. Vignais et al. [2001] *FEMS Microbiol. Rev.* 25, 455-501). In *C. reinhardtii*, the HydEF gene is assigned the two letters E and F to correspond to the two distinct genes observed in prokaryotic organisms. FIG. 3 compares the *C. reinhardtii* HydEF and HydG protein homologies to prokaryotic organisms containing [FeFe]-hydrogenases. This figure also shows the organization of the HydE, HydF and HydG open reading frames in relationship to the putative [FeFe]-hydrogenase gene(s) within these organisms. Although the proposed [FeFe]-hydrogenase assembly genes observed in the previously mentioned organisms are found in putative operons along with the [Fe]-hydrogenase structural genes, these proposed assembly proteins within the majority of the organisms shown in FIG. 3 are found separated from the structural genes.

Complementation of the HydEF Gene

To link the observed loss of $H_2$ production in the *C. reinhardtii* hydEF-1 mutant to disruption of HydEF, we used gene complementation. Genomic DNA, containing the WT HydEF gene, was obtained from a single BAC clone found in a library of *C. reinhardtii* genomic DNA. The BAC plasmid, containing the HydEF gene, was digested with appropriate restriction enzymes to generate a fragment predicted to contain only the full length HydEF genomic gene and its putative promoter. This insert was cloned into plasmid SP124S, which contains the Ble gene that confers resistance to the antibiotic zeocin. The hydEF-1 mutant was transformed with this construct, grown on TAP-agar plates containing zeocin, and clones with restored $H_2$-production capacity were obtained as shown in FIG. 2B. Integration of the complementing gene and verification of the mutant background were confirmed by Southern blotting (FIG. 2C). The CC425 sample shows the WT band, which is absent in both the mutant and the complemented clone. The complemented clone shows two strong bands corresponding to multiple random integration of the transformed HydEF genomic fragment into the mutant genome, as well as a faint band that may represent integration of only a portion of the HydEF gene.

Analysis of Gene Expression and [FeFe]-Hydrogenase Accumulation

Northern blot analyses were then performed to determine (a) whether the observed loss of hydrogenase activity in the hydEF-1 mutant was due to disruption of HydA1 and/or HydA2 gene transcription and (b) if HydEF and HydG are co-expressed anaerobically with the hydrogenase genes. RNA aliquots were collected from aerobic WT and hydEF-1 mutant cultures, as well as from WT and hydEF-1 mutant cultures anaerobically induced in the dark for 0.5 and 4.0 hours. FIGS. 4A-D compare, respectively, the expression profiles of the HydA1, HydA2, HydG and HydEF genes from both CC425 parental WT and hydEF-1 mutant cultures. The data demonstrate that HydEF and HydG are anaerobically induced concomitantly with the HydA1 and HydA2 genes in WT cultures. Likewise, the HydA1, HydA2, and HydG transcripts are also induced anaerobically in the hydEF-1 mutant, and as expected, the HydEF transcript is absent. The presence of HydA1 and HydA2 transcripts in anaerobically induced hydEF-1 cultures clearly indicates that disruption of the HydEF gene does not affect hydrogenase transcription in any significant fashion and that the loss of $H_2$ production in hydEF-1 cultures is not the consequence of a defect in hydrogenase gene transcription.

Figure 4:
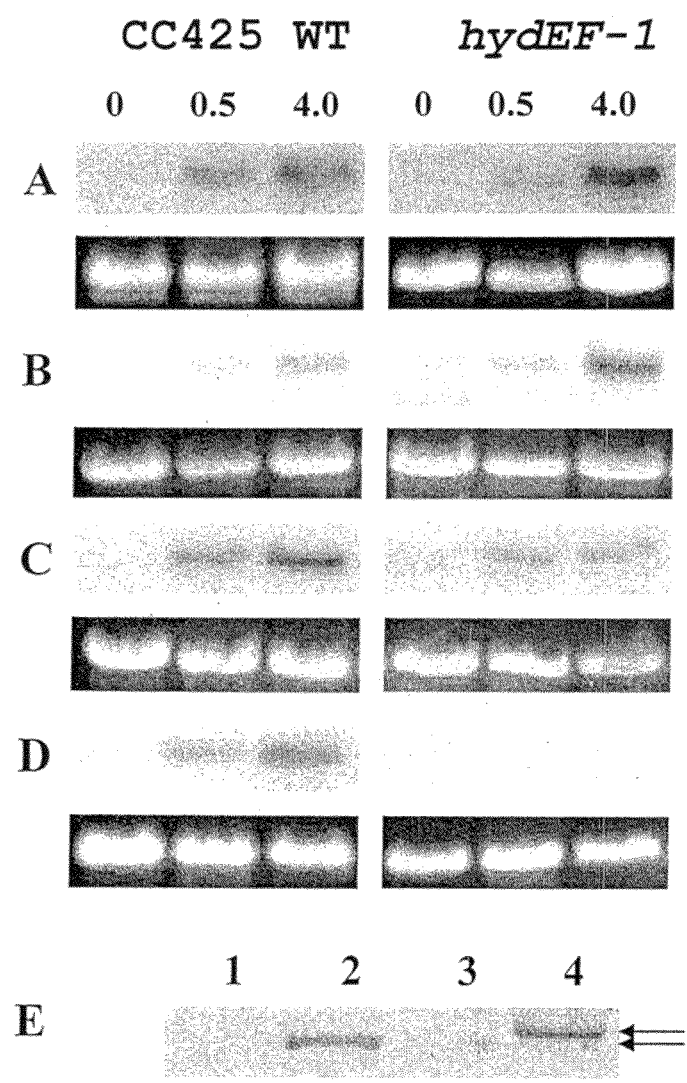
FIG. 4 shows Northern blots of the (A) HydA1, (B) HydA2 (C) HydG and (D) HydEF transcripts isolated from CC425 or hydEF-1 cultures. Anaerobic induction times of 0, 0.5 or 4 hours are indicated. RNA from WT and hydEF-1 cultures were electrophoresed, blotted and probed together in Northern blot experiments. The ribosomal 23S RNA band is shown as a loading control below each Northern blot. In (E), the Western blot is of partially purified protein extracts from aerobic and anaerobically induced samples. The blot was probed with an antibody designed to recognize both *C. reinhardtii* HydA1 and HydA2.

Western blots were then obtained to determine the consequence of HydEF gene disruption on hydrogenase protein levels (FIG. 4E). An antibody designed to recognize both *C. reinhardtii* HydA1 and HydA2 was used to probe for the presence of hydrogenase proteins. As expected, the partially purified WT sample (see Experimental Procedures) shows only a single anaerobically induced band with an electrophoretic mobility of approximately 47-48 kd, due to co-migration of the two hydrogenases. Although full length HydA1 and HydA2 hydrogenase enzymes from *C. reinhardtii* have predicted masses of 53.1 kd and 53.7 kd, respectively, HydA1 undergoes N-terminal proteolytic processing of a chloroplast transit peptide sequence, resulting in a mature 47.5 kd protein localized in the chloroplast (T. Happe et al. [1993] *Eur. J. Biochem.* 214, 475-481). The HydA2 protein is predicted to undergo similar processing, resulting in an estimated 47.3 kd mature protein (M. Forestier et al. [2003] *Eur. J. Biochem.* 270, 2750-2758). The Western data from anaerobically induced hydEF-1 cultures indicate that immunologically detectable enzyme is also found in hydEF-1 mutant cultures, despite the lack of detectable enzyme activity. The electrophoretic mobility of the hydrogenase band from hydEF-1 mutant cultures is shifted slightly lower relative to the WT band and is consistent with the electrophoretic mobility of unprocessed *C. reinhardtii* hydrogenase. In the case of [NiFe]-hydrogenases, proteolytic processing occurs after insertion of Ni, resulting in shifted Western bands relative to the unprocessed [NiFe]-enzyme (N. K. Menon et al [1991] *J. Bacterol.* 173, 4851-4861) (A. Jacobi et al. [1992] *Arch. Microbiol.* 158, 444-451) The presence of shifted bands in the anaerobically induced hydEF-1 protein extracts suggests that this might also occur in the case of *C. reinhardtii* [Fe]-hydrogenases lacking a fully assembled active site.

Heterologous Expression of *C. reinhardtii* HydA1 in *E. coli*.

Figure 5:
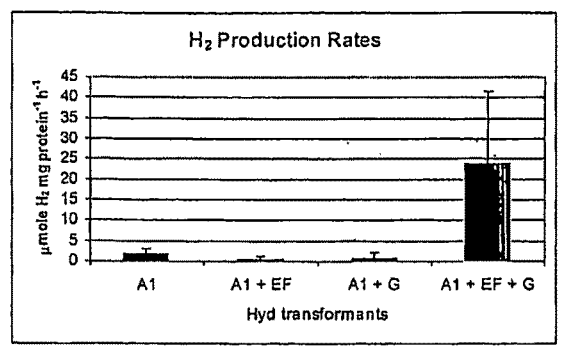
FIG. 5 shows hydrogen-production rares from purified HydA1 heterologously expressed *E. coli* either alone or co-expressed with the indicated Hyd proteins. Hydrogen production was measured using the methyl viologen-based assay. The data shown represent the average of four independent experiments, and average deviations from the mean are shown.

Additional evidence supporting the conclusion that the HydEF and HydG proteins are required for formation of an active [Fe]-hydrogenase is shown by the heterologous expression of active *C. reinhardtii* HydA1 protein in *E. coli*, a bacterium that lacks a native [FeFe]-hydrogenase. The HydA1 protein was expressed as a fusion protein containing a Strep-Tag II affinity sequence and purified from *E. coli* extracts. The expression of the HydA1 construct alone or co-expression of the HydA1 and HydEF, or HydA1 and HydG genes in *E. coli* all resulted in the expression of non-functional HydA1 protein after purification as shown in FIG. 5. However, the co-expression of *C. reinhardtii* HydA1 along with both HydEF and HydG in anaerobic *E. coli* cultures yielded an active HydA1 enzyme (FIG. 5). Since the expression system has yet to be optimized, the amount of active HydA1 obtained from independent experiments is low and varies significantly. Nevertheless, functional [FeFe]-hydrogenase was only obtained in the presence of all three expressed genes. It should be noted that some Radical SAM proteins act with extremely low turnover numbers, and may even be reactants and not catalysts (H. J. Sofia et al. [2001] *Nucleic Acids Res.* 29. 1097-1106).

Radical SAM Homology

The HydEF and HydG proteins belong to the Radical SAM (also known as the AdoMet radical) superfamily. These proteins participate in numerous biochemical reactions, including, but not limited to: sulfur insertion, radical formation, organic ring synthesis, and anaerobic oxidation. The HydG protein and the HydE domain of the *C. reinhardtii* HydEF protein both contain the signature $Cys-X_3-Cys-X_2-Cys$ motif that is typically found within the Radical SAM protein superfamily (FIG. 6). This motif coordinates a redox active [4Fe4S] cluster under reducing conditions. The reactions performed by Radical SAM proteins are typically initiated by the generation of a free radical after the reductive cleavage of S-adenosylmethionine (SAM) at the [4Fe4S] cluster, which yields methionine and a 5'-deoxyadenosyl radical. This high-energy organic radical then abstracts a hydrogen atom from substrates unique to each Radical SAM protein.

Roles for HydEF and HydG in H-Cluster Assembly

Radical SAM proteins are frequently involved in the anaerobic synthesis of complex biomolecules and coordinate unusual [FeS] clusters that are often labile. These characteristics are consistent with the types of chemistries required to synthesize the unique ligands of the H-cluster and to assemble the [FeFe]-hydrogenase catalytic cluster. A recent classification of the Radical SAM superfamily suggests that the most distantly related proteins, including biotin synthase (BioB) and the nitrogenase accessory protein NifB, appear to be involved in S transfer. Remarkably, Fe and S originating from the metabolic product of NifB, the NifB-cofactor, ultimately become incorporated into the [FeMo]-cofactor of dinitrogenase (R. M. Allen [1995] *J. Biol. Chem.* 270, 26890-

26896), another enzyme capable of $H_2$ production. Thus, there is precedent for the involvement of a Radical SAM protein in the donation of Fe to the catalytic metal cluster of an [Fe]-metalloenzyme, and we propose that the HydE and/or HydG proteins play a similar role in the mobilization of Fe for assembly of the [FeFe]-hydrogenase H-cluster.

The H-cluster also requires CN, CO and the putative di(thiomethyl)amine ligand. It is conceivable that the accessory proteins HydEF and/or HydG described are also responsible for biosynthesis and assembly of these products coordinated to Fe. Since CN and CO are among the most toxic compounds in biology, and likely do not exist freely within the cell, it would be necessary to synthesize these ligands at the site of H-cluster assembly. In the case of the [NiFe]-hydrogenases, strong evidence indicates that CN and CO are synthesized by the HypE and HypF proteins, using carbamoyl phosphate as a precursor to form a thiocarbamate. However, no homologues of the HypE and HypF proteins have been observed in *C. reinhardtii*, or in other organisms containing only [FeFe]-hydrogenases. This suggests an alternative pathway for CN and CO synthesis or an alternative means to form thiocarbamate. Radical SAM proteins utilize chemistries that include organic radical formation, persulfide formation, pyroxidal phosphate activation, thiocarbonyl formation, and amine migration, all or any one of which could be involved in the synthesis of the H-cluster organic ligands.

Homology alignments between *C. reinhardtii* HydEF and HydG relative to their prokaryotic homologues are shown in FIG. 6. In addition to the Radical SAM motifs, the HydG and HydF proteins have other conserved sequences with the potential to coordinate metal ions. These include a E(A/G)CXH and a (L/V)HC(G/A)(G/A)C motif near the C-terminus of the HydF domain, and a CT(A/G)CYR motif near the C-terminus of the HydG protein. All three of these motifs are strictly conserved in the [FeFe]-hydrogenase assembly proteins, but they are absent from other Radical SAM proteins, which suggests that these motifs are unique to the [FeFe]-hydrogenase accessory proteins. Several other conserved amino acids are found throughout the HydEF and HydG proteins; however, the elucidation of roles for these determinants and the potential metal-binding motifs in the assembly of [FeFe]-hydrogenase will likely have to await future investigation. It should also be noted that the HydF domain of the HydEF protein contains a putative GTPase domain, and the HypB protein, which also has GTPase activity, facilitates Ni incorporation into the active site of [NiFe]-hydrogenases. Interestingly, neither the HydEF or the HydG proteins are highly homologous to the TM1420 protein characterized from *T. maritima* (G. Pan et al. [2003] *J. Biol. Inorg. Chem.* 8, 469-474). The latter is only 8.5 kD long and does not contain a characteristic Radical SAM motif. This suggests that TM1420 may be unique to *T. maritima*, which has the most complex [FeFe]-hydrogenase characterized to date.

Heterologous Expression of *Chlamydomonas* [FeFe]-Hydrogenase

The heterologous expression of *C. reinhardtii* HydA1 in *E. coli*, demonstrates that only two *C. reinhardtii* gene products, HydEF and HydG (equivalent to three prokaryotic genes) are required for assembly of HydA 1; however, a minimum of seven accessory gene products are required for the formation of an active [NiFe]-hydrogenase enzyme (L. Casalot et al. [2001] *Trends Microbiol.* 9, 228-237). This is consistent with the prediction that the [FeFe]-hydrogenases may require fewer maturation proteins because these enzymes lack Ni (P. M. Vignais et al. [2001] *FEMS Microbiol. Rev.* 25, 455-501). The existence of entirely unique maturation proteins required for the assembly of [FeFe]-hydrogenase is consistent with the absence of a phylogenetic relationship between [NiFe] and [FeFe]-hydrogenases.

Previous attempts to express the CpI or DdH [FeFe]-hydrogenase enzymes in *E. coli* resulted in the synthesis of inactive proteins that were unable to evolve or uptake $H_2$ gas (G. Voordouw et al. [1987] *Eur. J. Biochem.* 162, 31-36) (Y. Asada et al. [2000] *Biochim. Biophys. Acta.* 1490, 269-278). In contrast, transformation of the cyanobacterium, *Synechococcus* PCC7942, with the CpI [FeFe]-hydrogenase structural gene yielded strains that expressed an active [FeFe]-hydrogenase. Given that there is no biochemical or genetic evidence for the presence of an [FeFe]-hydrogenase in *Synechoccocus* PCC7942, it appears that accessory proteins responsible for assembling the *Synechococcus* [NiFe]-hydrogenases are flexible enough to also activate the CpI [FeFe]-hydrogenase enzyme. It is not clear why this is possible in *Synechoccocus* and not in *E. coli*, but these results emphasize the complex nature of hydrogenase expression and activation in different microorganisms.

Expression and Biosynthesis of *C. acetobutylicum* [FeFe]-Hydrogenase HydA in *E. coli*—

Figure 7:
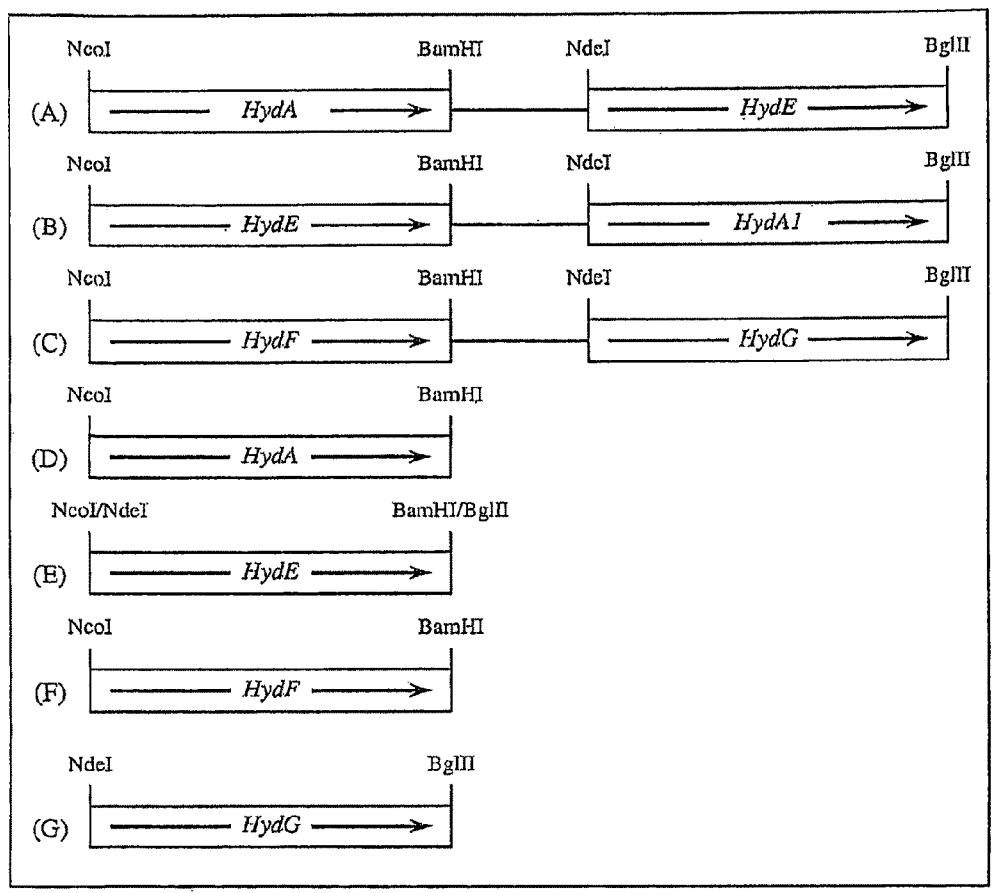
FIG. 7 shows plasmid constructs for T7-promoter expression of [FeFe]-hydrogenase maturation and structural genes. (A) Backbone pCaE2 was used to co-express HydE with either CaHydA (pCaAE) (depicted in the figure), CaHydB (pCaBE) or CaHydAΔN (pCaAΔNE) from *C. acetobutylicum*; or CpHyd, (pCpAE) or CpHydAΔN (pCpAΔNE) from *C. pasteurianum*. (B) Backbone pCaE1 was used to co-express HydE with either *C. reinhardtii* CrHydA1 (pECr1) (depicted in the figure) or CrHydA2 (pECr2). (C) pCaFG co-expresses *C. acetobutylicum* HydF and HydG. (D) pCaHydA expresses *C. acetobutylicum* HydA. (E) pCaE1 (HydE at the NcoIBamHI sites of MCS1) and pCaE2 (HydE at the NdeI-BglII sites of MCS2). (F) pCaF expresses *C. acetobutylicum* HydF. (G) pCaG expresses *C. acetobutylicum* HydG.
Figure 8:
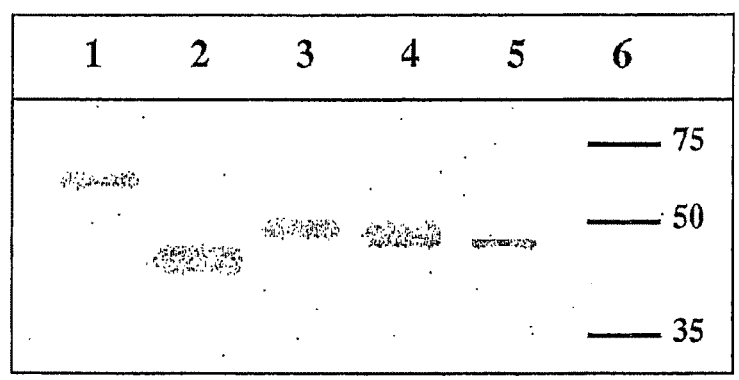
FIG. 8. shows a Western blot analysis of purified, StrepII-tagged [FeFe]-hydrogenases. Lane 1, *C. acetobutylicum* HydA (1.5 µg, 65 Kd); lane 2, *C. acetobutylicum* HydAΔN (2 µg, 43 Kd); lane 3, *C. acetobutylicum* HydB (5 µg, 50 Kd); lane 4, *C. reinhardtii* HydA1 (2.25 µg, 49 Kd); lane 5 *C. reinhardtii* HydA2 (1 µg, 49 Kd); lane 6, molecular weight markers, 75, 50 and 35 Kd.

Although the purified algal [FeFe]-hydrogenase expressed in *E. coli* as described above was active, the instability of the expression plasmids made the transformants difficult to propagate, which resulted in low HydA1 expression levels. The DNA compositions of algal genes are highly GC-biased at 64% overall, and 90% at the third codon position. To address codon bias effects on gene stability and expression, we searched the sequenced genomes of various anaerobic microbes for homologues of HydEF and HydG to use as alternatives to the algal genes. The genome of *C. acetobutylicum* was found to possess HydE, HydF and HydG homologues in agreement with previous reports on characterization of a soluble, monomeric [FeFe]-hydrogenase (CaHydA) in this organism. Unlike the high GC content of the *C. reinhardtii* HydEF (70%) and HydG (65%) genes, the *C. acetobutylicum* genes were more AT-rich (GC-content; HydE, 32%; HydF, 33%; HydG, 35%) and thus were expected to be more stable, and better expressed in *E. coli*. The *C. acetobutylicum* HydE, HydF and HydG genes were PCR amplified and the products cloned into a set of T7 expression plasmids together with the HydA gene encoding [FeFe]-hydrogenase I (FIG. 7). Plasmids that harbored a complete set of *C. acetobutylicum* maturation and structural genes were transformed into *E. coli* strain BL21 (DE3) for IPTG-inducible expression. Compared to the plasmid-encoded *C. reinhardtii* HydEF and HydG genes, which were observed to undergo some rearrangements upon propagation in *E. coli* (unpublished results), the plasmid-encoded *C. acetobutylicum* HydE, HydF, and HydG genes did not exhibit any sequence alterations. The higher stability of the *C. acetobutylicum* genes resulted in greater numbers of transformed cells, and higher growth rates under expression conditions (data not shown).

When *E. coli* is cultured under anaerobic growth in the absence of fermentable sugars, the endogenous [NiFe]-hydrogenases, Hyd1, Hyd2 and Hyd3 are uninduced due to the lack of formate. Formate is a fermentative metabolite required for the transcriptional activation of the hyp and hyc operons encoding maturation and Hyd3 structural genes respectively. As a result, anaerobic growth of *E. coli* in the absence of formate results in basal levels of [NiFe]-hydrogenase activities in whole-cell extracts as shown in TABLE I, which also, shows evolution of activities of [FeFe] hydrogenases anaerobically coexpressed with the *C. acetobutylicum* maturation proteins in *E. coli*.

TABLE I

| Organism | [FeFe] hydrogenase | Whole-cell extracts[a] (nmol $H_2$ ml$^{-1}$ min$^{-1}$) | Affinity purified ($\square$mol $H_2$ mg$^{-1}$ min$^{-1}$) |
|---|---|---|---|
| E. coli | | 0.35[b] | ND[c] |
| C. reinhardtii | HydA1 | 61 | 150 |
| C. reinhardtii | HydA2 | 108 | 116.1 |
| C. acetobutylicum | HydA | 96 | 75.2 |
| | HydAΔN | 6 | 31.6 |
| | HydB | 13 | 8.6 |
| C. pasteurianum | HydA | 150 | ND |
| | HydAΔN | 15 | ND |

[a]Whole cells solubilized with 0.1% Triton X-100.
[b]Whole cell activity in the absence of [FeFe]hydrogenase structural and maturation proteins.
[c]ND, not determined.

The basal [NiFe]-hydrogenase activities under these growth conditions allows for the study of maturation and biosynthesis of recombinantly expressed [FeFe]-hydrogenases. As shown in TABLE 1, the extracts of anaerobically grown E. coli cells expressing the C. acetobutylicum maturation system with the CaHydA structural protein exhibited reduced-MV-catalyzed, $H_2$-evolution activities fold greater than the activities in extracts of untransformed cells. These elevated hydrogenase activities are directly attributable to the high levels of plasmid-encoded C. acetobutylicum gene expression and the biosynthesis of CaHydA [FeFe]-hydrogenase.

The C. acetobutylicum maturation system produced mg-per-liter amounts of CaHydA, whereas our previous C. reinhardtii maturation system produced only μg-per-liter amounts of the C. reinhardtii HydA1. As shown in TABLE 1, the specific activity of reduced-MV catalyzed, $H_2$-evolution by affinity-purified StrepII-tagged CaHydA was 75 μmol $H_2$ mg$_{-1}$ min$_{-1}$, 7.5-fold higher than the value reported by Girbal et al. of CaI purified from C. acetobutylicum (L. Gerbal et al. Appl. Env Microbiol. 71, 2777-2781).

Biosynthesis of Heterologous [FeFe]-Hydrogenases by the C. acetobutylicum Maturation System—

Figure 9:
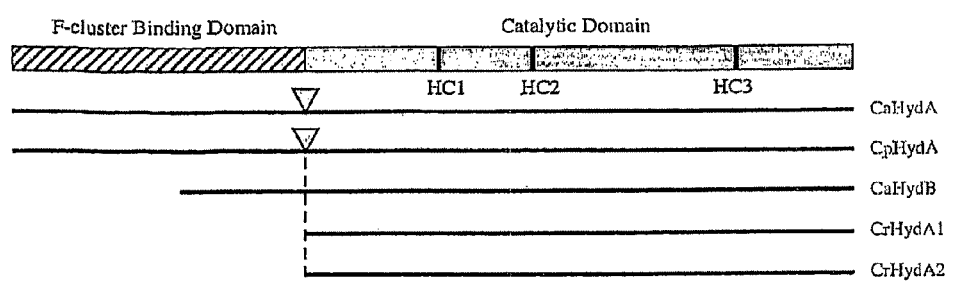
FIG. 9 is a schematic representation of aligned sequences of [FeFe]-hydrogenases used in this study (Ca=*C. acetobutylicum*, Cp=*C. pasteuriaiium*, Cr=*C. reinhardtii*). The top diagram represents the relative location of conserved F-cluster binding domains (cross-hatched lines), and the H-cluster binding motifs HC1 (TSCCP) and HC2 (MACPGGC) (dark bars) found in soluble [FeFe]-hydrogenases. The arrow heads indicate the N-termini of conserved F-cluster-binding domains deleted in *C. acetobutylicum* and *C. pasteurianum* HydAΔN constructs.

Our interest in studying the biochemical and structural properties of the [FeFe]-hydrogenases found in the green algae C. reinhardtii prompted a test of the capability of the C. acetobutylicum to biosynthesize the algal enzymes. A characteristic of the algal [FeFe]-hydrogenase peptide sequences is the lack of accessory iron-sulfur-cluster domains auxiliary to the highly conserved H-cluster/catalytic domain (FIG. 9). This reduced structural complexity classifies the algal hydrogenases as the simplest yet characterized. In C. reinhardtii, the CrHydA1 [FeFe]-hydrogenase undergoes N-terminal processing as a result of translocation from the cytoplasm to the chloroplast stroma. Similar to CrHydA1, the N-terminal sequence of CrHydA2 also possesses signal sequence characteristics with a predicted cleavage site near amino acid position 61. For expression in E. coli, a truncated HydA2 was cloned into expression plasmid pCaE, which created an N-terminus at position 62 that corresponds to the predicted processed product. As shown in Table 1, the mature forms of both CrHydA1 and CrHydA2 were biosynthesized as active enzymes in E. coli. Following affinity purification the typical yields of these proteins ranged from 0.8 to 1.0 mg-per-liter-of-culture. The $H_2$-production activities from reduced-MV of purified CrHydA1 and CrHydA2 were 150 and 116 μmol $H_2$ mg$^{-1}$ min$^{-1}$ respectively. This measured activity for CrHydA1 purified from our E. coli expression system was 5 to 6-fold lower than the previously published activities of this enzyme purified from a recombinant, or native source. It has been established that under anaerobic conditions, C. reinhardtii utilizes reduced [2Fe2S]-ferredoxin as electron-donor to [FeFe]-hydrogenase for in vivo $H_2$-production. Previous measurements of $H_2$-evolution kinetics with partially purified C. reinhardtii hydrogenases and reduced C. reinhardtii [2Fe2S]-ferredoxin showed a $K_m$ of 10 μM. The $K_m$ of reduced spinach [2Fe2S]-ferredoxin for purified HydA2 in this study was measured at 31 μM. This value is similar to the previous reported value of 35 μM for purified HydA1 and reduced spinach ferredoxin, suggesting that HydA2 is capable of catalyzing in vivo $H_2$-production in C. reinhardtii.

In summary, two novel genes, HydEF and HydG, found in C. reinhardtii, are strictly conserved in organisms containing [Fe]-hydrogenases. The HydEF and HydG genes are transcribed anaerobically in parallel with the HydA1 and HydA2 [Fe]-hydrogenase genes in C. reinhardtii. Disruption of HydEF abolishes all $H_2$ production, and although full-length hydrogenase protein is detected by Western blotting, no enzyme activity is observed. Hydrogen production is restored after complementation of the hydEF-1 mutant with WT genomic DNA containing the HydEF gene. Moreover, we report the first successful co-expression of the C. reinhardtii HydEF, HydG and HydA1 genes in E. coli, and the synthesis of an active [FeFe]-hydrogenase in this bacterium. The current study also identifies a new class of metallo-enzyme accessory proteins and assigns assembly function to two proteins belonging to a subset of the Radical SAM superfamily. Characterization of these [FeFe]-hydrogenase assembly proteins will greatly facilitate additional examination of the mechanism by which [Fe]-hydrogenases are synthesized in nature.

Our results clearly show that H-cluster biosynthesis is a highly conserved process. Together with recent structural data on [FeFe]-hydrogenases CpI (denoted CpHydA in this study) and DdH, our work supports early observations that various [FeFe]-hydrogenases possess essentially identical H-clusters. This is perhaps more apparent in the case of CaHydB, which has only low sequence identity with CaHydA (119%), but undergoes maturation by the same set of C. acetobutylicum proteins.

The efforts to develop biological alternatives to fossil fuels have helped stimulate an ongoing interest in the use of microorganisms as production sources for a number of energy carriers. The physiology of $H_2$-producing organisms, and the hydrogenases that mediate $H_2$ metabolism, have been intensely studied for use as large-scale $H_2$-production sources. A greater understanding of how the hydrogenases are biosynthesized, and how their unique structures contribute to biochemical and metabolic function will assist in the continued development of both biological and bio-inspired $H_2$-production systems.

While the invention has been described in detail with reference to preferred embodiments, it is to be understood that this description is by way of example only and not to be construed as limiting. Accordingly, numerous changes in the details of the embodiments of the invention and additional embodiments of the invention will be apparent to, and may be made by persons of ordinary skill in the art having reference to this description, and all such changes and additional embodiments are within the true scope of the spirit of the invention, as claimed hereafter.

The invention claimed is:

1. An *E. coli* cell that co-expresses exogenous genes encoding HydEF and HydG and also expresses a hydrogenase structural gene.

2. The *E. coli* cell of claim 1, wherein the HydEF and HydG genes are from a green algae.

3. The *E. coli* cell of claim 1, wherein the HydEF and HydG genes are from an organism of the genus *Chlamydomonas*.

4. The *E. coli* cell of claim 1, wherein the HydEF and HydG genes are from *Chlamydomonas reinhardtii*.

5. The *E. coli* cell of claim 1, wherein the hydrogenase structural gene is HydA1 or HydA2.

6. The *E. coli* cell of claim 5, wherein the HydA1 or HydA2 gene is from a green algae.

7. The *E. coli* cell of claim 5, wherein the HydA1 or HydA2 gene is from an organism of the genus *Chlamydomonas*.

8. The *E. coli* cell of claim 5, wherein the HydA1 or HydA2 gene is from *Chlamydomonas reinhardtii*.

* * * * *

SEQUENCE LISTING

<160> NUMBER OF SEQ ID NOS: 34

<210> SEQ ID NO 1
<211> LENGTH: 5
<212> TYPE: PRT
<213> ORGANISM: Clostridium acetobutylicum

<400> SEQUENCE: 1

Thr Ser Cys Cys Pro
1               5

<210> SEQ ID NO 2
<211> LENGTH: 7
<212> TYPE: PRT
<213> ORGANISM: Clostridium acetobutylicum

<400> SEQUENCE: 2

Met Ala Cys Pro Gly Gly Cys
1               5

<210> SEQ ID NO 3
<211> LENGTH: 12
<212> TYPE: PRT
<213> ORGANISM: synthetic peptide

<400> SEQUENCE: 3

Asp Lys Ala Lys Arg Gln Ala Ala Leu Tyr Asn Leu
1               5                   10

<210> SEQ ID NO 4
<211> LENGTH: 8
<212> TYPE: PRT
<213> ORGANISM: synthetic peptide

<400> SEQUENCE: 4

Trp Ser His Pro Gln Phe Glu Lys
1               5

<210> SEQ ID NO 5
<211> LENGTH: 621
<212> TYPE: PRT
<213> ORGANISM: Chlamydomonas reinhardtii

<400> SEQUENCE: 5

Met Ala His Ser Leu Ser Ala His Ser Arg Gln Ala Gly Asp Arg Lys
1               5                   10                  15

Leu Gly Ala Gly Ala Ala Ser Ser Arg Pro Ser Cys Pro Ser Arg Arg
                20                  25                  30

Ile Val Arg Val Ala Ala His Ala Ser Ala Ser Lys Ala Thr Pro Asp
            35                  40                  45

Val Pro Val Asp Asp Leu Pro Pro Ala His Ala Arg Ala Ala Val Ala
        50                  55                  60

Ala Ala Asn Arg Arg Ala Arg Ala Met Ala Ser Ala Glu Ala Ala Ala
65                  70                  75                  80

Glu Thr Leu Gly Asp Phe Leu Gly Leu Gly Lys Gly Leu Ser Pro
                85                  90                  95

Gly Ala Thr Ala Asn Leu Asp Arg Glu Gln Val Leu Val Leu Glu
                100                 105                 110

Ala Val Trp Arg Arg Gly Asp Leu Asn Leu Asp Arg Ala Leu Tyr Ser
            115                 120                 125

His Ala Asn Ala Val Thr Asn Lys Tyr Cys Gly Gly Gly Val Tyr Tyr

-continued

```
            130                 135                 140
Arg Gly Leu Val Glu Phe Ser Asn Ile Cys Gln Asn Asp Cys Ser Tyr
145                 150                 155                 160

Cys Gly Ile Arg Asn Asn Gln Lys Glu Val Trp Arg Tyr Thr Met Pro
                165                 170                 175

Val Glu Glu Val Val Glu Val Ala Lys Trp Ala Leu Glu Asn Gly Ile
                180                 185                 190

Arg Asn Ile Met Leu Gln Gly Gly Glu Leu Lys Thr Glu Gln Arg Leu
            195                 200                 205

Ala Tyr Leu Glu Ala Cys Val Arg Ala Ile Arg Glu Glu Thr Thr Gln
210                 215                 220

Leu Asp Leu Glu Met Arg Ala Arg Ala Ala Ser Thr Thr Thr Ala Glu
225                 230                 235                 240

Ala Ala Ala Ser Ala Gln Ala Asp Ala Glu Ala Lys Arg Gly Glu Pro
                245                 250                 255

Glu Leu Gly Val Val Val Ser Leu Ser Val Gly Glu Leu Pro Met Glu
                260                 265                 270

Gln Tyr Glu Arg Leu Phe Arg Ala Gly Ala Arg Arg Tyr Leu Ile Arg
            275                 280                 285

Ile Glu Thr Ser Asn Pro Asp Leu Tyr Ala Ala Leu His Pro Glu Pro
290                 295                 300

Met Ser Trp His Ala Arg Val Glu Cys Leu Arg Asn Leu Lys Lys Ala
305                 310                 315                 320

Gly Tyr Met Leu Gly Thr Gly Val Met Val Gly Leu Pro Gly Gln Thr
                325                 330                 335

Leu His Asp Leu Ala Gly Asp Val Met Phe Phe Arg Asp Ile Lys Ala
                340                 345                 350

Asp Met Ile Gly Met Gly Pro Phe Ile Thr Gln Pro Gly Thr Pro Ala
            355                 360                 365

Thr Asp Lys Trp Thr Ala Leu Tyr Pro Asn Ala Asn Lys Asn Ser His
370                 375                 380

Met Lys Ser Met Phe Asp Leu Thr Thr Ala Met Asn Ala Leu Val Arg
385                 390                 395                 400

Ile Thr Met Gly Asn Val Asn Ile Ser Ala Thr Ala Leu Gln Ala
                405                 410                 415

Ile Ile Pro Thr Gly Arg Glu Ile Ala Leu Glu Arg Gly Ala Asn Val
                420                 425                 430

Val Met Pro Ile Leu Thr Pro Thr Gln Tyr Arg Glu Ser Tyr Gln Leu
            435                 440                 445

Tyr Glu Gly Lys Pro Cys Ile Thr Asp Thr Ala Val Gln Cys Arg Arg
450                 455                 460

Cys Leu Asp Met Arg Leu His Ser Val Gly Lys Thr Ser Ala Ala Gly
465                 470                 475                 480

Val Trp Gly Asp Pro Ala Ser Phe Leu His Pro Ile Val Gly Val Pro
                485                 490                 495

Val Pro His Asp Leu Ser Ser Pro Ala Leu Ala Ala Ala Ser Ala
                500                 505                 510

Asp Phe His Glu Val Gly Ala Gly Pro Trp Asn Pro Ile Arg Leu Glu
            515                 520                 525

Arg Leu Val Glu Val Pro Asp Arg Tyr Pro Asp Pro Asp Asn His Gly
530                 535                 540

Arg Lys Lys Ala Gly Ala Gly Lys Gly Gly Lys Ala His Asp Ser His
545                 550                 555                 560
```

```
Asp Asp Gly Asp His Asp Asp His His His His Gly Ala Ala Pro
            565                 570                 575

Ala Gly Ala Ala Ala Gly Lys Gly Thr Gly Ala Ala Ile Gly Gly
            580                 585                 590

Gly Ala Gly Ala Ser Arg Gln Arg Val Ala Gly Ala Ala Ala Ser
            595                 600                 605

Ala Arg Leu Cys Ala Gly Ala Arg Arg Ala Gly Arg Val
            610                 615                 620

<210> SEQ ID NO 6
<211> LENGTH: 350
<212> TYPE: PRT
<213> ORGANISM: Clostridium acetobutylicum

<400> SEQUENCE: 6

Met Asp Asn Ile Ile Lys Leu Ile Asn Lys Ala Glu Val Thr His Asp
1               5                   10                  15

Leu Thr Lys Asp Glu Leu Val Thr Leu Leu Lys Asp Asp Thr His Asn
            20                  25                  30

Glu Glu Ile Tyr Lys Ala Ala Asp Arg Val Arg Glu Lys Tyr Val Gly
        35                  40                  45

Glu Glu Val His Leu Arg Gly Leu Ile Glu Phe Ser Asn Ile Cys Lys
    50                  55                  60

Arg Asn Cys Met Tyr Cys Gly Leu Arg Arg Asp Asn Lys Asn Ile Lys
65                  70                  75                  80

Arg Tyr Arg Leu Glu Pro Asp Glu Ile Ile His Leu Ala Lys Ser Ala
                85                  90                  95

Lys Asn Tyr Gly Tyr Gln Thr Val Val Leu Gln Ser Gly Glu Asp Asp
            100                 105                 110

Tyr Tyr Thr Val Glu Lys Met Lys Tyr Ile Val Ser Glu Ile Lys Lys
        115                 120                 125

Leu Asn Met Ala Ile Thr Leu Ser Ile Gly Glu Lys Thr Phe Glu Glu
    130                 135                 140

Tyr Glu Glu Tyr Arg Lys Ser Gly Ala Asp Arg Tyr Leu Ile Arg Ile
145                 150                 155                 160

Glu Thr Thr Asp Lys Glu Leu Tyr Glu Lys Leu Asp Pro Lys Met Ser
                165                 170                 175

His Glu Asn Arg Ile Asn Cys Leu Lys Asn Leu Arg Lys Leu Gly Tyr
            180                 185                 190

Glu Val Gly Ser Gly Cys Leu Val Gly Leu Pro Asn Gln Thr Ile Glu
        195                 200                 205

Ser Leu Ala Asp Asp Ile Leu Phe Phe Lys Glu Ile Asp Ala Asp Met
    210                 215                 220

Ile Gly Val Gly Pro Phe Ile Pro Asn Glu Asp Thr Pro Leu Gly Glu
225                 230                 235                 240

Glu Lys Gly Gly Glu Phe Phe Met Ser Val Lys Val Thr Ala Leu Ile
                245                 250                 255

Arg Leu Leu Leu Pro Asp Ile Asn Ile Pro Ala Thr Thr Ala Met Glu
            260                 265                 270

Ser Leu Tyr Pro Asn Gly Arg Ser Ile Ala Leu Thr Ser Gly Ala Asn
        275                 280                 285

Val Val Met Pro Asn Val Thr Glu Gly Glu Tyr Arg Lys Leu Tyr Ala
    290                 295                 300

Leu Tyr Pro Gly Lys Ile Cys Val Asn Asp Thr Pro Gly His Cys Arg
```

```
              305                 310                 315                 320
Gln Cys Ile Ser Leu Lys Ile Asn Lys Ile Asn Arg Lys Val Ser Ala
                325                 330                 335

Thr Lys Gly Phe Arg Lys Lys Ser Tyr Lys Glu Ser Ile Gly
                340                 345                 350

<210> SEQ ID NO 7
<211> LENGTH: 347
<212> TYPE: PRT
<213> ORGANISM: Clostridium perfringens

<400> SEQUENCE: 7

Met Asn Thr Ile Ile Gln Lys Ala Lys Glu Thr His Glu Leu Ser Arg
1               5                   10                  15

Asp Glu Ile Ile Ala Leu Leu Lys Asp Asp Ser Ile Asn Glu Glu Leu
                20                  25                  30

Phe Lys Ala Ala Asp Glu Val Arg Lys Tyr Leu Gly Asp Glu Val
                35                  40                  45

His Leu Arg Gly Leu Ile Glu Phe Thr Asn Ile Cys Lys Arg Asn Cys
        50                  55                  60

Met Tyr Cys Gly Leu Arg Arg Asp Asn Lys Asn Leu Asn Arg Tyr Arg
65              70                  75                  80

Leu Ser His Glu Glu Ile Ile Asp Phe Ala Lys Lys Ala Val Gly Tyr
                85                  90                  95

Gly Tyr Lys Thr Leu Val Leu Gln Gly Gly Glu Asp Asp Tyr Tyr Thr
            100                 105                 110

Val Glu Arg Leu Val Pro Ile Val Lys Asp Leu Lys Ala Leu Gly Val
            115                 120                 125

Ala Leu Thr Leu Ser Ile Gly Glu Arg Pro Phe Glu Glu Tyr Glu Ala
        130                 135                 140

Leu Lys Lys Ala Gly Ala Asp Arg Phe Leu Leu Arg Ile Glu Thr Thr
145                 150                 155                 160

Asp Arg Glu Leu Tyr Glu Glu Leu Asp Pro Gly Met Ser His Glu Asn
                165                 170                 175

Arg Ile Gln Cys Leu Lys Asn Leu Arg Lys Leu Gly Tyr Glu Val Gly
            180                 185                 190

Ser Gly Cys Leu Val Gly Leu Pro Gly Gln Lys Ile Glu Ser Leu Ala
        195                 200                 205

Asp Asp Ile Leu Phe Phe Lys Glu Leu Asp Val Asp Met Asn Gly Ile
    210                 215                 220

Gly Pro Phe Ile Pro Asn Glu Asp Thr Pro Leu Lys Asp Ala Glu Gly
225                 230                 235                 240

Gly Gln Phe Glu Leu Ala Leu Lys Val Met Ala Ile Val Arg Leu Leu
                245                 250                 255

Leu Pro Asp Ile Asn Ile Pro Ala Thr Thr Ala Met Glu Thr Leu Asn
            260                 265                 270

Lys Gln Gly Arg Val Ile Ala Leu Gln Cys Gly Ala Asn Val Val Met
        275                 280                 285

Pro Asn Val Thr Glu Gly Glu Tyr Arg Lys Leu Tyr Ala Leu Tyr Pro
    290                 295                 300

Gly Lys Ile Cys Thr Gly Asp Thr Pro Ala His Cys Arg Gly Cys Ile
305                 310                 315                 320

Ser Gly Lys Ile Arg Gly Ile Gly Arg Ile Val Ser Asp Gly Pro Gly
                325                 330                 335
```

```
Phe Arg Ala Asn Gly Phe Lys Pro Lys Thr Arg
                340                 345
```

<210> SEQ ID NO 8
<211> LENGTH: 353
<212> TYPE: PRT
<213> ORGANISM: Clostridium thermocellum

<400> SEQUENCE: 8

```
Met Thr Asn Met Thr Asn Met Ile Asn Leu Ile Asp Lys Leu Ser Thr
1               5                   10                  15

Thr His Thr Leu Ser Tyr Asp Glu Met Tyr Gln Leu Ile Glu His Arg
            20                  25                  30

Asn Glu Glu Leu Ala Asn Tyr Leu Phe Glu Lys Ala Arg Gln Val Arg
        35                  40                  45

Ile Leu Tyr Tyr Gly His Asp Val Tyr Met Arg Gly Leu Ile Glu Phe
    50                  55                  60

Thr Asn Tyr Cys Arg Asn Asp Cys Tyr Cys Gly Ile Arg Lys Ser
65                  70                  75                  80

Asn Cys Asn Ala Glu Arg Tyr Arg Leu Thr Lys Glu Gln Ile Leu Glu
                85                  90                  95

Cys Cys Asp Val Gly Tyr Glu Leu Gly Phe Arg Thr Phe Val Leu Gln
            100                 105                 110

Gly Gly Glu Asp Gly Tyr Tyr Thr Asp Lys Ile Leu Ala Asp Ile Val
        115                 120                 125

Ser Ser Ile Lys Ala Lys Tyr Pro Asp Cys Ala Ile Thr Leu Ser Leu
    130                 135                 140

Gly Glu Lys Ser Tyr Glu Ser Tyr Lys Leu Leu Tyr Glu Ala Gly Ala
145                 150                 155                 160

Asp Arg Tyr Leu Leu Arg His Glu Thr Ala Asn Ala Gln His Tyr Ser
                165                 170                 175

Lys Leu His Pro Pro Val Met Ser Leu Lys Asn Arg Lys Gln Cys Leu
            180                 185                 190

Tyr Asn Leu Lys Glu Ile Gly Tyr Gln Val Gly Cys Gly Phe Met Val
        195                 200                 205

Gly Ser Pro Phe Gln Thr Thr Glu Cys Leu Val Asp Asp Leu Met Phe
    210                 215                 220

Ile Lys Glu Leu Gln Pro His Met Val Gly Ile Gly Pro Phe Ile Pro
225                 230                 235                 240

His Lys Asp Thr Pro Phe Ala Gly Lys Pro Ala Gly Thr Leu Glu Leu
                245                 250                 255

Thr Leu Phe Leu Leu Gly Ile Ile Arg Leu Met Leu Pro Tyr Val Leu
            260                 265                 270

Leu Pro Ala Thr Thr Ala Leu Gly Thr Ile His Pro Lys Gly Arg Glu
        275                 280                 285

Leu Gly Ile Leu Ala Gly Ala Asn Val Val Met Pro Asn Leu Ser Pro
    290                 295                 300

Lys Glu Val Arg Ser Lys Tyr Leu Leu Tyr Asp Asn Lys Ile Cys Thr
305                 310                 315                 320

Gly Asp Glu Ala Ala Glu Cys Arg Met Cys Leu Thr His Arg Ile Glu
                325                 330                 335

Ser Ile Gly Tyr Lys Leu Val Val Ser Arg Gly Asp Cys Lys Lys Pro
            340                 345                 350

Asn
```

<210> SEQ ID NO 9
<211> LENGTH: 348
<212> TYPE: PRT
<213> ORGANISM: Thermotoga maritima

<400> SEQUENCE: 9

Met Thr Gly Arg Glu Ile Leu Glu Lys Leu Glu Arg Glu Phe Thr
1               5                   10                  15

Arg Glu Val Leu Lys Glu Ala Leu Ser Ile Asn Asp Arg Gly Phe Asn
            20                  25                  30

Glu Ala Leu Phe Lys Leu Ala Asp Glu Ile Arg Arg Lys Tyr Val Gly
                35                  40                  45

Asp Glu Val His Ile Arg Ala Ile Ile Glu Phe Ser Asn Val Cys Arg
    50                  55                  60

Lys Asn Cys Leu Tyr Cys Gly Leu Arg Arg Asp Asn Lys Asn Leu Lys
65                  70                  75                  80

Arg Tyr Arg Met Thr Pro Glu Glu Ile Val Glu Arg Ala Arg Leu Ala
                85                  90                  95

Val Gln Phe Gly Ala Lys Thr Ile Val Leu Gln Ser Gly Glu Asp Pro
            100                 105                 110

Tyr Tyr Met Pro Asp Val Ile Ser Asp Ile Val Lys Glu Ile Lys Lys
        115                 120                 125

Met Gly Val Ala Val Thr Leu Ser Leu Gly Glu Trp Pro Arg Glu Tyr
    130                 135                 140

Tyr Glu Lys Trp Lys Glu Ala Gly Ala Asp Arg Tyr Leu Leu Arg His
145                 150                 155                 160

Glu Thr Ala Asn Pro Val Leu His Arg Lys Leu Arg Pro Asp Thr Ser
                165                 170                 175

Phe Glu Asn Arg Leu Asn Cys Leu Leu Thr Leu Lys Glu Leu Gly Tyr
            180                 185                 190

Glu Thr Gly Ala Gly Ser Met Val Gly Leu Pro Gly Gln Thr Ile Asp
        195                 200                 205

Asp Leu Val Asp Asp Leu Leu Phe Leu Lys Glu His Asp Phe Asp Met
    210                 215                 220

Val Gly Ile Gly Pro Phe Ile Pro His Pro Asp Thr Pro Leu Ala Asn
225                 230                 235                 240

Glu Lys Lys Gly Asp Phe Thr Leu Thr Leu Lys Met Val Ala Leu Thr
                245                 250                 255

Arg Ile Leu Leu Pro Asp Ser Asn Ile Pro Ala Thr Thr Ala Met Gly
            260                 265                 270

Thr Ile Val Pro Gly Gly Arg Glu Ile Thr Leu Arg Cys Gly Ala Asn
        275                 280                 285

Val Ile Met Pro Asn Trp Thr Pro Ser Pro Tyr Arg Gln Leu Tyr Gln
    290                 295                 300

Leu Tyr Pro Gly Lys Ile Cys Val Phe Glu Lys Asp Thr Ala Cys Ile
305                 310                 315                 320

Pro Cys Val Met Lys Met Ile Glu Leu Leu Gly Arg Lys Pro Gly Arg
                325                 330                 335

Asp Trp Gly Gly Arg Lys Arg Val Phe Glu Thr Val
            340                 345

<210> SEQ ID NO 10
<211> LENGTH: 345
<212> TYPE: PRT
<213> ORGANISM: Bacteroides thetaiotaomicron

<400> SEQUENCE: 10

Met Arg Gln Trp Ile Asp Lys Leu Arg Glu Arg Thr Leu Arg Pro
1               5                   10                  15

Glu Glu Phe Arg Gln Leu Leu Thr Glu Cys Asp Gly Glu Ser Leu Arg
            20                  25                  30

Tyr Ile Asn Lys Gln Ala Gln Glu Val Ser Leu Arg His Phe Gly Asn
                35                  40                  45

Arg Ile Phe Ile Arg Gly Leu Ile Glu Val Ser Asn Cys Cys Arg Asn
        50                  55                  60

Asn Cys Tyr Tyr Cys Gly Ile Arg Lys Gly Asn Pro Asn Leu Glu Arg
65                  70                  75                  80

Tyr Arg Leu Ser Thr Glu Asn Ile Leu Asn Cys Cys Lys Gln Gly Tyr
                85                  90                  95

Gly Leu Gly Phe Arg Thr Phe Val Leu Gln Gly Gly Glu Asp Pro Ala
            100                 105                 110

Leu Thr Glu Glu Arg Ile Glu Asp Ile Val Ser Thr Ile Arg Arg Ser
                115                 120                 125

Tyr Pro Asp Cys Ala Ile Thr Leu Ser Leu Gly Glu Lys Ser Arg Glu
130                 135                 140

Ala Tyr Glu Arg Phe Phe Gln Ala Gly Ala Asn Arg Tyr Leu Leu Arg
145                 150                 155                 160

His Glu Thr Tyr Asp Lys Glu His Tyr Gln Leu His Pro Ala Gly
                165                 170                 175

Met Ser Cys Glu His Arg Leu Gln Cys Leu Arg Asp Leu Lys Asp Ile
            180                 185                 190

Gly Tyr Gln Thr Gly Thr Gly Ile Met Val Gly Ser Pro Gly Gln Thr
                195                 200                 205

Ile Glu His Leu Ile Gln Asp Ile Leu Phe Ile Glu Gln Leu Arg Pro
210                 215                 220

Glu Met Ile Gly Ile Gly Pro Phe Leu Ser His Arg Asp Thr Pro Phe
225                 230                 235                 240

Ala Gln Ser Pro Ser Gly Thr Val Glu Arg Thr Leu Leu Leu Ser
            245                 250                 255

Ile Phe Arg Leu Met His Pro Ser Ala Leu Ile Pro Ala Thr Thr Ala
                260                 265                 270

Leu Ala Thr Leu Thr Pro Asp Arg Glu Gln Gly Ile Leu Ala Gly
                275                 280                 285

Ala Asn Val Val Met Pro Asn Leu Ser Pro Gln Glu Arg Lys Lys
        290                 295                 300

Tyr Asn Leu Tyr Asn Asn Lys Ala Ser Leu Gly Ala Glu Ser Ala Glu
305                 310                 315                 320

Gly Leu Asn Ile Leu Gln Gln Leu Glu Lys Ile Gly Tyr Gln Ile
                325                 330                 335

Ser Phe Ser Arg Gly Asp Tyr Lys Gln
            340                 345

<210> SEQ ID NO 11
<211> LENGTH: 349
<212> TYPE: PRT
<213> ORGANISM: Clostridium tetani

<400> SEQUENCE: 11

Met Lys Ile Lys Asp Ile Ile Asp Lys Ala Tyr Val Glu Ser Asn Leu
1               5                   10                  15

```
Ser Gln Glu Glu Ile Val Glu Ile Leu Lys Asn Lys Asp Glu Tyr Asn
            20                  25                  30

Ile Lys Tyr Leu Phe Asn Lys Ala Glu Glu Thr Thr Glu Lys Tyr Cys
        35                  40                  45

Gly His Glu Val Asn Ile Arg Gly Ile Ile Glu Phe Ser Asn Tyr Cys
    50                  55                  60

Arg Cys Asn Cys Ser Tyr Cys Gly Leu Asn Val Asn Asn Asn Gly Ile
65                  70                  75                  80

Lys Arg Tyr Arg Met Ser Lys Glu Glu Ile Val Leu Val Ala Lys Glu
                85                  90                  95

Ala Tyr Glu Ala Gly Tyr Lys Thr Leu Val Leu Gln Ser Gly Glu Asp
            100                 105                 110

Leu Phe Tyr Thr Arg Glu Ile Leu Cys Asp Ile Ile Lys Ser Ile Lys
        115                 120                 125

Lys Ile Gly Asp Ile Ala Ile Thr Leu Ser Ile Gly Lys Arg Asp Lys
    130                 135                 140

Glu Asp Tyr Arg Ala Phe Lys Lys Ala Gly Asp Arg Phe Leu Ile
145                 150                 155                 160

Lys His Glu Thr Ala Asp Lys Asn Leu Phe Ser Lys Leu His Lys Gly
                165                 170                 175

Asn Lys Leu Glu Asn Arg Ile Gln Ala Leu Lys Asp Leu Lys Glu Val
            180                 185                 190

Gly Phe Gln Ala Gly Ser Gly Phe Met Ile Gly Leu Pro Leu Gln Asp
        195                 200                 205

Phe Asn Thr Leu Ala Arg Asp Ile Leu Leu Lys Glu Leu Asp Val
    210                 215                 220

Asp Met Ala Gly Ile Gly Pro Phe Ile Pro His Pro Glu Thr Asp Leu
225                 230                 235                 240

Lys Gly Glu His Lys Gly Asp Thr Leu Leu Thr Leu Lys Val Val Ala
                245                 250                 255

Leu Ser Arg Ile Ile Leu Lys Asn Ile His Leu Pro Ala Thr Thr Ser
            260                 265                 270

Leu Gly Val Leu Asn Lys Asp His Lys Phe Thr Ser Phe Lys Cys Gly
        275                 280                 285

Ala Asn Val Ile Met Gln Lys Leu Glu Pro Tyr Lys Tyr Arg Arg Leu
    290                 295                 300

Tyr Glu Ile Tyr Pro Ile Glu Leu Arg Glu Glu Lys Ser Ile Arg Glu
305                 310                 315                 320

Glu Arg Lys Asp Val Glu Asn Phe Ile Leu Ser Ser Gly Lys Glu Ile
                325                 330                 335

Ala Lys His Arg Gly Asp Thr Leu Lys Arg Ser Asp Leu
            340                 345

<210> SEQ ID NO 12
<211> LENGTH: 351
<212> TYPE: PRT
<213> ORGANISM: Desulfovibrio desulfuricans

<400> SEQUENCE: 12

Met Thr Ser Arg Asp Ile Leu Glu Met Leu Ala Ala Thr Gly Gly Gly
1               5                   10                  15

Pro Val Tyr Ala Glu Ala Arg Thr Val Ala Asp Arg Phe Phe Gly Arg
            20                  25                  30

Gly Val Tyr Val Arg Gly Val Val Glu Phe Ser Asn His Cys Arg Lys
```

```
                35                  40                  45
Asn Cys His Tyr Cys Gly Leu Arg Val Ala Asn Thr Gly Leu Glu Arg
 50                  55                  60

Phe Arg Leu Glu Pro Glu Gly Ile Leu Ala Ala Ala Leu Ala Arg
 65                  70                  75                  80

Glu Leu Gly Ala Gly Thr Val Val Leu Gln Ser Gly Glu Asp Leu Arg
                 85                  90                  95

Tyr Asp Arg Arg Val Ile Gly Asp Leu Val Arg Ile Arg Asp Thr
                100                 105                 110

Leu Asp Val Ala Val Thr Leu Ser Leu Gly Asp Phe Asp Arg Asp Thr
                115                 120                 125

Tyr Ala Tyr Trp Arg Asp Cys Gly Ala Asp Arg Tyr Leu Leu Lys Met
130                 135                 140

Glu Thr Phe Asp Glu Ala Leu His Ala Arg Leu Arg Pro Gly Cys Thr
145                 150                 155                 160

Val Ala Asp Arg Leu Ala Arg Val Glu Met Leu Gln Ser Leu Gly Tyr
                165                 170                 175

Glu Thr Gly Ser Gly Ile Ile Val Gly Leu Pro Gly Met Thr Asp Ala
                180                 185                 190

Ile Leu Ala Glu Asp Ile His Arg Leu Ser Gln Leu Gly Leu Glu Met
                195                 200                 205

Ile Ala Ala Gly Pro Phe Ile Pro His Pro Ser Thr Pro Leu Ala Ala
210                 215                 220

Pro Val Asp His Ala Ile Glu Lys Ser Leu Leu Val Thr Ala Val Leu
225                 230                 235                 240

Arg Leu Leu Asn Pro Gly Ala Asn Ile Pro Ala Thr Ser Ala Leu Asp
                245                 250                 255

Ala Leu Ala Ala Asp Gly Arg Thr Arg Gly Leu Asp Ala Gly Ala Asn
                260                 265                 270

Val Val Met Pro Ser Val Thr Pro Asp Ala Val Arg Gly Gly Tyr Ser
                275                 280                 285

Ile Tyr Pro Gly Lys Asn Ala Ala Gly Arg Asp Val Arg Asp Ala Val
290                 295                 300

His Gly Leu Phe Glu Arg Leu Arg Asn Ala Gly Tyr Thr Pro Val Ala
305                 310                 315                 320

Asp Lys Gly Phe Ser Arg Ile Ala Gly Ala Cys Gly Gly Asn Ala Asp
                325                 330                 335

Val Met Arg Val Arg Ser Ala Arg Lys Val Leu Ala Arg Thr Asp
                340                 345                 350

<210> SEQ ID NO 13
<211> LENGTH: 359
<212> TYPE: PRT
<213> ORGANISM: shewanella oneidensis

<400> SEQUENCE: 13

Met Ile Thr Arg Pro Ser Pro Ala Pro Val Thr Gln Pro Thr Ser
 1               5                  10                  15

Val Lys Pro Thr Leu Leu Asn Thr Val Phe Ser Tyr Ala Glu Ile Leu
                 20                  25                  30

Ser Leu Leu Gln Gly Gln Asp Asp Glu Trp Leu Phe Ser Arg Ala Lys
                 35                  40                  45

Leu Ala Thr Glu Leu Glu Phe Asn Gln Gln Val Tyr Leu Arg Gly Ile
 50                  55                  60
```

```
Val Glu Phe Ser Asn His Cys Arg Asn His Cys His Tyr Cys Gly Leu
 65                  70                  75                  80

Arg Thr Glu Asn Arg Gln Val Thr Arg Tyr Arg Leu Ser Asn Glu Glu
                 85                  90                  95

Ile Leu Asn Ala Val Asp Ser Ile Ala Glu Leu Gly Leu Gly Thr Val
            100                 105                 110

Val Leu Gln Ser Gly Asp Asp Phe Asn Tyr Ser Gly Asn Arg Ile Ser
        115                 120                 125

Thr Leu Ile Thr Glu Ile Lys Arg His His Asn Leu Ala Ile Thr Leu
        130                 135                 140

Ser Leu Gly Asp Arg Lys His Gln Glu Leu Glu Lys Trp Arg Glu Ala
145                 150                 155                 160

Gly Ala Asp Arg Tyr Leu Leu Lys Met Glu Thr Phe Asp Arg Ala Leu
                165                 170                 175

Phe Ala Gln Cys Arg Pro Lys Ala Asn Phe Asp Glu Arg Ile Ala Arg
            180                 185                 190

Leu Asn Tyr Leu Lys Ser Leu Gly Tyr Gln Thr Gly Ser Gly Ile Ile
        195                 200                 205

Val Asp Leu Pro Gly Met Thr Asp Ala Ile Leu Ala Arg Asp Ile Gln
    210                 215                 220

His Leu Ser Glu Leu Gln Leu Asp Met Leu Ala Cys Gly Pro Phe Ile
225                 230                 235                 240

Ala His His Gln Thr Pro Phe Thr Thr Ser Pro Asn Gly Ser Ala Leu
                245                 250                 255

Lys Ser His Arg Val Ser Ala Ile Leu Arg Leu Met Asn Pro Gly Ala
            260                 265                 270

Asn Ile Pro Ala Thr Ser Ser Leu Asp Ala Leu Asp Lys Gly Ala Arg
        275                 280                 285

Glu Gln Ala Leu Lys Arg Gly Cys Asn Val Ile Met Pro Ser Phe Thr
    290                 295                 300

Pro Thr Lys Val Ser Gly Asp Tyr Ser Ile Tyr Pro Gly Lys Asn Gln
305                 310                 315                 320

Gln Gln His Pro Ala Ala Glu Arg Leu Asn Gln Val Cys Gln Gln Ile
                325                 330                 335

Gln Arg His Gly Leu Ile Pro Ser Phe Ser Arg Gly Asp Ser Lys Arg
            340                 345                 350

Thr Gln Tyr Val Ser Arg His
        355

<210> SEQ ID NO 14
<211> LENGTH: 530
<212> TYPE: PRT
<213> ORGANISM: Chlamydomonas reinhardtii

<400> SEQUENCE: 14

Val Ala Ser Pro Leu Arg Pro Ala Ala Cys Arg Gly Val Ala Val
 1               5                  10                  15

Lys Ala Ala Ala Ala Ala Gly Glu Asp Ala Gly Ala Gly Thr Ser
                 20                  25                  30

Gly Val Gly Ser Asn Ile Val Ser Pro Gly Ile Ala Ser Thr Thr
             35                  40                  45

Ala His Gly Val Pro Arg Ile Asn Ile Gly Val Phe Gly Val Met Asn
         50                  55                  60

Ala Gly Lys Ser Thr Leu Val Asn Ala Leu Ala Gln Gln Glu Ala Cys
 65                  70                  75                  80
```

```
Ile Val Asp Ser Thr Pro Gly Thr Thr Ala Asp Val Lys Thr Val Leu
                85              90              95

Leu Glu Leu His Ala Leu Gly Pro Ala Lys Leu Leu Asp Thr Ala Gly
                100             105             110

Leu Asp Glu Val Gly Gly Leu Gly Asp Lys Lys Arg Arg Lys Ala Leu
                115             120             125

Asn Thr Leu Lys Glu Cys Asp Val Ala Val Leu Val Asp Thr Asp
    130             135             140

Thr Ala Ala Ala Ala Ile Lys Ser Gly Arg Leu Ala Glu Ala Leu Glu
145             150             155             160

Trp Glu Ser Lys Val Met Glu Gln Ala His Lys Tyr Asn Val Ser Pro
                165             170             175

Val Leu Leu Leu Asn Val Lys Ser Arg Gly Leu Pro Glu Ala Gln Ala
                180             185             190

Ala Ser Met Leu Glu Ala Val Ala Gly Met Leu Asp Pro Ser Lys Gln
                195             200             205

Ile Pro Arg Met Ser Leu Asp Leu Ala Ser Thr Pro Leu His Glu Arg
    210             215             220

Ser Thr Ile Thr Ser Ala Phe Val Lys Glu Gly Ala Val Arg Ser Ser
225             230             235             240

Arg Tyr Gly Ala Pro Leu Pro Gly Cys Leu Pro Arg Trp Ser Leu Gly
                245             250             255

Arg Asn Ala Arg Leu Leu Met Val Ile Pro Met Asp Ala Glu Thr Pro
                260             265             270

Gly Gly Arg Leu Leu Arg Pro Gln Ala Gln Val Met Glu Glu Ala Ile
                275             280             285

Arg His Trp Ala Thr Val Leu Ser Val Arg Leu Asp Leu Asp Ala Ala
    290             295             300

Arg Gly Lys Leu Gly Pro Glu Ala Cys Glu Met Glu Arg Gln Arg Phe
305             310             315             320

Asp Gly Val Ile Ala Met Met Glu Arg Asn Asp Gly Pro Thr Leu Val
                325             330             335

Val Thr Asp Ser Gln Ala Ile Asp Val Val His Pro Trp Thr Leu Asp
                340             345             350

Arg Ser Ser Gly Arg Pro Leu Val Pro Ile Thr Thr Phe Ser Ile Ala
                355             360             365

Met Ala Tyr Gln Gln Asn Gly Gly Arg Leu Asp Pro Phe Val Glu Gly
                370             375             380

Leu Glu Ala Leu Glu Thr Leu Gln Asp Gly Asp Arg Val Leu Ile Ser
385             390             395             400

Glu Ala Cys Asn His Asn Arg Ile Thr Ser Ala Cys Asn Asp Ile Gly
                405             410             415

Met Val Gln Ile Pro Asn Lys Leu Glu Ala Ala Leu Gly Gly Lys Lys
                420             425             430

Leu Gln Ile Glu His Ala Phe Gly Arg Glu Phe Pro Glu Leu Glu Ser
                435             440             445

Gly Gly Met Asp Gly Leu Lys Leu Ala Ile His Cys Gly Gly Cys Met
                450             455             460

Ile Asp Ala Gln Lys Met Gln Gln Arg Met Lys Asp Leu His Glu Ala
465             470             475             480

Gly Val Pro Val Thr Asn Tyr Gly Val Phe Phe Ser Trp Ala Ala Trp
                485             490             495
```

-continued

```
Pro Asp Ala Leu Arg Arg Ala Leu Glu Pro Trp Gly Val Glu Pro Pro
            500                 505                 510

Val Gly Thr Pro Ala Thr Pro Ala Ala Pro Ala Thr Ala Ala Ser
        515                 520                 525

Gly Val
    530

<210> SEQ ID NO 15
<211> LENGTH: 411
<212> TYPE: PRT
<213> ORGANISM: Clostridium acetobutylicum

<400> SEQUENCE: 15

Met Asn Glu Leu Asn Ser Thr Pro Lys Gly Glu Arg Leu His Ile Ala
1               5                   10                  15

Leu Phe Gly Lys Thr Asn Val Gly Lys Ser Ser Val Ile Asn Ala Leu
            20                  25                  30

Thr Ser Gln Glu Ile Ala Leu Val Ser Asn Val Lys Gly Thr Thr Thr
        35                  40                  45

Asp Pro Val Tyr Lys Ala Met Glu Leu Leu Pro Leu Gly Pro Val Met
    50                  55                  60

Leu Ile Asp Thr Ala Gly Leu Asp Asp Ile Ser Asp Leu Gly Glu Leu
65                  70                  75                  80

Arg Arg Gly Lys Thr Leu Glu Val Leu Ser Lys Thr Asp Val Ala Ile
                85                  90                  95

Leu Val Phe Asp Val Glu Ser Gly Ile Thr Glu Tyr Asp Lys Asn Ile
            100                 105                 110

Tyr Ser Leu Leu Leu Glu Lys Lys Ile Pro Leu Ile Gly Val Leu Asn
        115                 120                 125

Lys Ile Asp Lys Lys Asp Tyr Lys Leu Glu Asp Tyr Thr Ser Gln Phe
    130                 135                 140

Lys Ile Pro Ile Val Pro Ile Ser Ala Leu Asn Asn Lys Gly Ile Asn
145                 150                 155                 160

Asn Leu Lys Asp Glu Leu Ile Arg Leu Ala Pro Glu Asn Asp Asp Lys
                165                 170                 175

Phe Lys Ile Val Gly Asp Leu Leu Ser Pro Gly Asp Ile Ala Val Leu
            180                 185                 190

Val Thr Pro Ile Asp Lys Ala Ala Pro Lys Gly Arg Leu Ile Leu Pro
        195                 200                 205

Gln Gln Gln Thr Ile Arg Asp Ile Leu Glu Ser Asp Ala Ile Ala Met
    210                 215                 220

Val Thr Lys Glu Phe Glu Leu Arg Glu Thr Leu Asp Ser Leu Arg Lys
225                 230                 235                 240

Lys Pro Lys Ile Val Ile Thr Asp Ser Gln Val Phe Leu Lys Val Ala
                245                 250                 255

Ala Asp Thr Pro Lys Asp Ile Leu Met Thr Ser Phe Ser Ile Leu Met
            260                 265                 270

Ala Arg His Lys Gly Asp Leu Ile Glu Leu Ala Arg Gly Ala Arg Ala
        275                 280                 285

Ile Glu Asp Leu Lys Asp Gly Asp Lys Ile Leu Ile Ala Glu Ala Cys
    290                 295                 300

Thr His His Arg Gln Ser Asp Asp Ile Gly Lys Val Lys Ile Pro Arg
305                 310                 315                 320

Trp Leu Arg Gln Lys Thr Gly Lys Lys Leu Glu Phe Asp Phe Ser Ser
                325                 330                 335
```

Gly Phe Ser Phe Pro Pro Asn Ile Glu Asp Tyr Ala Leu Ile Val His
                340                 345                 350

Cys Ala Gly Cys Met Leu Asn Arg Arg Ser Met Leu His Arg Ile Glu
                355                 360                 365

Ser Ser Val Lys Lys Gln Ile Pro Ile Val Asn Tyr Gly Val Leu Ile
            370                 375                 380

Ala Tyr Val Gln Gly Ile Leu Pro Arg Ala Leu Lys Pro Phe Pro Tyr
385                 390                 395                 400

Ala Asp Arg Ile Phe Asn Gln Ser Ser Arg Asn
                405                 410

<210> SEQ ID NO 16
<211> LENGTH: 454
<212> TYPE: PRT
<213> ORGANISM: Clostridium perfringens

<400> SEQUENCE: 16

Met Gln Phe Tyr Tyr Leu His Leu Ala Ile Val Glu Lys Phe Met Ser
1               5                   10                  15

Asn Phe Asn Glu Thr Pro Arg Gly Ser Arg Ile His Ile Ser Leu Phe
                20                  25                  30

Gly Lys Thr Asn Ser Gly Lys Ser Ser Ile Ile Asn Ala Leu Thr Gly
            35                  40                  45

Gln Asn Ile Ser Leu Val Ser Asp Phe Lys Gly Thr Thr Asp Pro
        50                  55                  60

Val Tyr Lys Ala Met Glu Leu Leu Pro Leu Gly Pro Val Val Phe Val
65                  70                  75                  80

Asp Thr Ala Gly Phe Asp Asp Glu Gly Glu Ile Gly Lys Leu Arg Val
                85                  90                  95

Glu Lys Thr Glu Glu Val Val Gly Lys Thr Asp Val Ala Leu Ile Thr
                100                 105                 110

Leu Ser Leu Ser Glu Ile Leu Glu Ala Ile Lys Ser Asn Ile Glu Phe
            115                 120                 125

Lys Asp Met Leu Ser Lys Glu Ile Leu Trp Leu Asn Lys Leu Lys Lys
        130                 135                 140

Ala Lys Lys Pro Ala Ile Leu Val Ile Asn Lys Cys Asp Leu Val Pro
145                 150                 155                 160

Asn Lys Leu Ile Glu Ser Lys Ile Asp Leu Lys Asp Ile Asp Lys Thr
                165                 170                 175

Thr Leu Ser Asn Lys Asp Cys Phe Val Asp Ser Asn Leu Asn Asn Ser
            180                 185                 190

Leu Lys Glu Ile Gly Glu Leu Leu Gly Ile Pro Cys Val Ala Ile Ser
        195                 200                 205

Ala Lys Asn Asn Leu Asn Ile Asn Glu Leu Lys Lys Glu Leu Val Asn
210                 215                 220

Val Ser Pro Ser Ser Ile Thr Glu Ser Pro Ile Ile Gly Asp Lys Ile
225                 230                 235                 240

Lys Ala Gly Asp Lys Ile Leu Leu Val Ala Pro Gln Asp Ile Gln Ala
                245                 250                 255

Pro Lys Gly Arg Leu Ile Leu Pro Gln Val Gln Val Leu Arg Asp Ile
            260                 265                 270

Leu Asp Tyr Gly Gly Ile Pro Thr Met Val Thr Leu Asp Lys Leu Asp
        275                 280                 285

Glu Gly Leu Arg Ile Phe Asn Gly Lys Pro Asp Leu Val Ile Thr Asp

```
              290                 295                 300
Ser Gln Val Phe Lys Gln Val Asn Ala Lys Leu Asp Arg Ser Val Pro
305                 310                 315                 320

Leu Thr Ser Phe Ser Ile Leu Met Ala Arg Tyr Lys Gly Asp Leu Asp
                325                 330                 335

Lys Phe Tyr Ser Gly Ala Lys Ala Ile Lys Asn Leu Lys Ala Gly Asp
                340                 345                 350

Lys Val Leu Ile Ala Glu Ala Cys Thr His His Gln Leu Lys Gly Asp
            355                 360                 365

Ile Ala Arg Glu Lys Leu Pro Thr Trp Leu Glu Glu Thr Cys Pro Gly
        370                 375                 380

Ile Ile Val His Asn Cys Ser Gly Lys Asp Phe Pro Lys Asn Leu Asn
385                 390                 395                 400

Glu Tyr Ala Leu Val Ile His Cys Gly Gly Cys Met Phe Asn Lys Ala
                405                 410                 415

Glu Ile Met Asn Arg Ile Gly Ile Cys Asp Asp Ala Leu Val Pro Ile
                420                 425                 430

Thr Asn Phe Gly Thr Ser Ile Ala Glu Ile Asn Asn Ile Leu Asp Arg
            435                 440                 445

Val Met Glu Pro Leu Lys
        450

<210> SEQ ID NO 17
<211> LENGTH: 400
<212> TYPE: PRT
<213> ORGANISM: Clostridium thermocellum

<400> SEQUENCE: 17

Met Gly Leu Asn Glu Thr Pro Ser Ala Asn Arg Leu His Ile Gly Phe
1               5                   10                  15

Phe Gly Lys Arg Asn Ala Gly Lys Ser Ser Val Val Asn Ala Val Thr
                20                  25                  30

Gly Gln Asn Leu Ala Ile Val Ser Asp Val Lys Gly Thr Thr Thr Asn
            35                  40                  45

Pro Val Tyr Lys Ala Met Glu Leu Leu Pro Leu Gly Pro Val Val Ile
        50                  55                  60

Ile Asp Thr Pro Gly Ile Asp Asp Lys Gly Thr Leu Gly Glu Met Arg
65                  70                  75                  80

Val Lys Arg Ser Arg Gln Val Leu Asn Lys Thr Asp Ile Ala Val Leu
                85                  90                  95

Val Ile Asp Ala Thr Cys Gly Lys Ser Glu Asp Asp Glu Lys Leu Ile
                100                 105                 110

Glu Leu Phe Glu Lys Lys Asp Ile Lys Tyr Val Val Val Tyr Asn Lys
            115                 120                 125

Ala Asp Leu Glu Gly His Glu Glu Thr Val Gly Asp Asn Glu Ile Tyr
        130                 135                 140

Val Ser Ala Lys Thr Gly Tyr Asn Ile Asn Lys Leu Lys Glu Lys Ile
145                 150                 155                 160

Ala Ser Leu Ala Val Thr Asp Asp Ile Thr His Lys Ile Val Gly Asp
                165                 170                 175

Leu Ile Ser Pro Ser Asp Phe Val Val Leu Val Pro Ile Asp Lys
            180                 185                 190

Ala Ala Pro Lys Gly Arg Leu Ile Leu Pro Gln Gln Gln Thr Ile Arg
        195                 200                 205
```

```
Asp Ile Leu Glu Ser Asp Ala Val Ala Ile Val Lys Glu Asn Glu
    210                 215                 220

Leu Lys Asn Thr Leu Asp Ser Leu Gly Lys Lys Pro Lys Leu Val Ile
225                 230                 235                 240

Thr Asp Ser Gln Ala Phe Glu Lys Val Ala Ala Asp Thr Pro Asp Asp
                245                 250                 255

Ile Tyr Leu Thr Ser Phe Ser Ile Leu Phe Ala Arg Tyr Lys Gly Asn
            260                 265                 270

Leu Glu Ile Ala Val Lys Gly Ala Lys Thr Leu Asp Ser Leu Gln Asp
        275                 280                 285

Gly Asp Thr Val Leu Ile Ser Glu Gly Cys Thr His His Arg Gln Cys
290                 295                 300

Asp Asp Ile Gly Thr Val Lys Leu Pro Arg Trp Ile Asn Asn Tyr Thr
305                 310                 315                 320

Lys Lys Asn Leu Asn Phe Glu Phe Thr Ser Gly Thr Glu Phe Pro Glu
                325                 330                 335

Asp Leu Thr Arg Tyr Lys Leu Ile Val His Cys Gly Gly Cys Met Leu
            340                 345                 350

Asn Glu Arg Glu Met Lys Tyr Arg Tyr Lys Cys Ala Val Glu Gln Asn
        355                 360                 365

Val Pro Ile Thr Asn Tyr Gly Ile Leu Ile Ala Tyr Val His Gly Ile
    370                 375                 380

Leu Lys Arg Ser Leu Gln Ile Phe Pro Asp Ile Leu Ala Glu Ile Leu
385                 390                 395                 400

<210> SEQ ID NO 18
<211> LENGTH: 404
<212> TYPE: PRT
<213> ORGANISM: Thermotoga maritima

<400> SEQUENCE: 18

Met Arg Leu Pro Asp Ala Gly Phe Arg Arg Tyr Ile Val Val Ala Gly
1               5                   10                  15

Arg Arg Asn Val Gly Lys Ser Ser Phe Met Asn Ala Leu Val Gly Gln
                20                  25                  30

Asn Val Ser Ile Val Ser Glu Tyr Ala Gly Thr Thr Thr Asp Pro Val
            35                  40                  45

Tyr Lys Ser Met Glu Leu Tyr Pro Val Gly Pro Val Thr Leu Val Asp
        50                  55                  60

Thr Pro Gly Leu Asp Asp Val Gly Glu Leu Gly Arg Leu Arg Val Glu
65                  70                  75                  80

Lys Ala Arg Arg Val Phe Tyr Arg Ala Asp Cys Gly Ile Leu Val Thr
                85                  90                  95

Asp Ser Glu Pro Thr Pro Tyr Glu Asp Val Val Asn Leu Phe Lys
            100                 105                 110

Glu Met Glu Ile Pro Phe Val Val Val Asn Lys Ile Asp Val Leu
        115                 120                 125

Gly Glu Lys Ala Glu Glu Leu Lys Gly Leu Tyr Glu Ser Arg Tyr Glu
    130                 135                 140

Ala Lys Val Leu Leu Val Ser Ala Leu Gln Lys Lys Gly Phe Asp Asp
145                 150                 155                 160

Ile Gly Lys Thr Ile Ser Glu Ile Leu Pro Gly Asp Glu Glu Ile Pro
                165                 170                 175

Tyr Leu Gly Asp Leu Ile Asp Gly Gly Asp Leu Val Ile Leu Val Val
            180                 185                 190
```

```
Pro Ile Asp Leu Gly Ala Pro Lys Gly Arg Leu Ile Met Pro Gln Val
        195                 200                 205

His Ala Ile Arg Glu Ala Leu Asp Arg Glu Ala Ile Ala Leu Val Val
        210                 215                 220

Lys Glu Arg Glu Leu Arg Tyr Val Met Glu Asn Ile Gly Met Lys Pro
225                 230                 235                 240

Lys Leu Val Ile Thr Asp Ser Gln Val Met Lys Val Ala Ser Asp
                245                 250                 255

Val Pro Glu Asp Val Glu Leu Thr Thr Phe Ser Ile Val Glu Ser Arg
            260                 265                 270

Tyr Arg Gly Asp Leu Ala Tyr Phe Val Glu Ser Val Arg Lys Ile Glu
            275                 280                 285

Glu Leu Glu Asp Gly Asp Thr Val Val Ile Met Glu Gly Cys Thr His
        290                 295                 300

Arg Pro Leu Thr Glu Asp Ile Gly Arg Val Lys Ile Pro Arg Trp Leu
305                 310                 315                 320

Val Asn His Thr Gly Ala Gln Leu Asn Phe Lys Val Ile Ala Gly Lys
                325                 330                 335

Asp Phe Pro Asp Leu Glu Glu Ile Glu Gly Ala Lys Leu Ile Ile His
            340                 345                 350

Cys Gly Gly Cys Val Leu Asn Arg Ala Ala Met Met Arg Arg Val Arg
        355                 360                 365

Met Ala Lys Arg Leu Gly Ile Pro Met Thr Asn Tyr Gly Val Thr Ile
    370                 375                 380

Ser Tyr Leu His Gly Val Leu Asp Arg Ala Ile Arg Pro Phe Arg Glu
385                 390                 395                 400

Glu Val Lys Val

<210> SEQ ID NO 19
<211> LENGTH: 405
<212> TYPE: PRT
<213> ORGANISM: Bacteroides thetaiotaomicron

<400> SEQUENCE: 19

Met Asn Leu Val His Thr Pro Asn Ala Asn Arg Leu His Ile Ala Leu
1               5                   10                  15

Phe Gly Lys Arg Asn Ser Gly Lys Ser Ser Leu Ile Asn Ala Leu Thr
            20                  25                  30

Gly Gln Asp Thr Ala Leu Val Ser Asp Thr Pro Gly Thr Thr Thr Asp
        35                  40                  45

Ser Val Gln Lys Ala Met Glu Ile His Gly Ile Gly Pro Cys Leu Phe
    50                  55                  60

Ile Asp Thr Pro Gly Phe Asp Asp Glu Gly Leu Gly Asn Arg Arg
65                  70                  75              80

Ile Glu Arg Thr Trp Lys Ala Val Glu Lys Thr Asp Ile Ala Leu Leu
                85                  90                  95

Leu Cys Ala Gly Gly Ser Ala Glu Glu Thr Gly Glu Pro Asp Phe
            100                 105                 110

Thr Glu Glu Leu His Trp Leu Glu Gln Leu Lys Ala Lys Asn Ile Pro
        115                 120                 125

Thr Ile Leu Leu Ile Asn Lys Ala Asp Ile Arg Lys Asn Thr Ala Ser
    130                 135                 140

Leu Ala Ile Arg Ile Lys Glu Thr Phe Gly Ser Gln Pro Ile Pro Val
145                 150                 155                 160
```

```
Ser Ala Lys Glu Lys Thr Gly Val Glu Leu Ile Arg Gln Ala Ile Leu
            165                 170                 175

Glu Lys Leu Pro Glu Asp Phe Asp Gln Gln Ser Ile Thr Gly Ser Leu
        180                 185                 190

Val Thr Glu Gly Asp Leu Val Leu Val Met Pro Gln Asp Ile Gln
    195                 200                 205

Ala Pro Lys Gly Arg Leu Ile Leu Pro Gln Val Gln Thr Met Arg Glu
    210                 215                 220

Leu Leu Asp Lys Lys Cys Leu Ile Met Ser Cys Thr Thr Asp Lys Leu
225                 230                 235                 240

Gln Glu Thr Leu Gln Ala Leu Ser Arg Pro Pro Lys Leu Ile Ile Thr
                245                 250                 255

Asp Ser Gln Val Phe Lys Thr Val Tyr Glu Gln Lys Pro Glu Glu Ser
            260                 265                 270

Arg Leu Thr Ser Phe Ser Val Leu Phe Ala Gly Tyr Lys Gly Asp Ile
        275                 280                 285

Arg Tyr Tyr Val Lys Ser Ala Ser Ala Ile Gly Ser Leu Thr Glu Ser
    290                 295                 300

Ser Arg Val Leu Ile Ala Glu Ala Cys Thr His Ala Pro Leu Ser Glu
305                 310                 315                 320

Asp Ile Gly Arg Val Lys Leu Pro His Leu Leu Arg Lys Arg Ile Gly
                325                 330                 335

Glu Lys Leu Ser Ile Asp Ile Val Ala Gly Thr Asp Phe Pro Gln Asp
            340                 345                 350

Leu Thr Pro Tyr Ser Leu Val Ile His Cys Gly Ala Cys Met Phe Asn
        355                 360                 365

Arg Lys Tyr Val Leu Ser Arg Ile Glu Arg Ala Arg Leu Gln Asn Val
    370                 375                 380

Pro Met Thr Asn Tyr Gly Val Ala Ile Ala Phe Leu Asn Gly Ile Leu
385                 390                 395                 400

Asn Gln Ile Glu Tyr
            405

<210> SEQ ID NO 20
<211> LENGTH: 396
<212> TYPE: PRT
<213> ORGANISM: Clostridium tetani

<400> SEQUENCE: 20

Met Gln Asp Thr Pro Lys Gly Asn Arg Ile His Ile Ala Phe Leu Gly
1               5                   10                  15

Arg Arg Asn Ala Gly Lys Ser Ser Ile Ile Asn Ala Ile Ser Asn Gln
            20                  25                  30

Gln Val Ser Ile Val Ser Asn Val Ala Gly Thr Thr Thr Asp Pro Val
        35                  40                  45

Tyr Lys Ala Met Glu Leu Phe Pro Ile Gly Pro Ile Met Leu Ile Asp
    50                  55                  60

Thr Ala Gly Leu Asp Asp Glu Gly Tyr Ile Gly Asn Leu Arg Ile Glu
65                  70                  75                  80

Lys Thr Lys Glu Ile Met Asn Lys Thr Asp Ile Ala Val Ile Ala Ile
                85                  90                  95

Asp Cys Lys Asn Glu Asn Phe Glu Tyr Glu Met Tyr Leu Lys Glu Lys
            100                 105                 110

Leu Ser Lys Arg Lys Ile Pro Thr Ile Ile Ala Leu Asn Lys Ile Asp
```

```
            115                 120                 125
Lys Val Ala Asn Leu Asp Glu Ala Ile Val Arg Ala Arg Lys Gln Phe
        130                 135                 140

Asp Asn Ile Val Ser Ile Ser Ala Leu Arg Arg Glu Asn Ile Asp Lys
145                 150                 155                 160

Leu Lys Glu Lys Ile Ile Glu Gln Val Pro Ser Asn Asn Glu Thr Thr
                165                 170                 175

Leu Leu Glu Gly Ile Val Asn Lys Lys Asp Leu Val Leu Ile Thr
            180                 185                 190

Pro Gln Asp Leu Gln Ala Pro Lys Gly Arg Leu Ile Leu Pro Gln Val
        195                 200                 205

Gln Val Leu Arg Asp Ile Leu Asp Lys Gly Ala Met Ala Met Val Leu
    210                 215                 220

Lys Asp Thr Glu Leu Gln Glu Gly Leu Lys Asn Leu Tyr Lys Lys Pro
225                 230                 235                 240

Asp Leu Val Ile Thr Asp Ser Gln Ile Phe Asn Lys Val Lys Asp Ile
                245                 250                 255

Ile Pro Arg Asp Ile Lys Leu Thr Ser Phe Ser Val Leu Met Ala Arg
            260                 265                 270

Tyr Lys Gly Asp Ile Arg Leu Ile Glu Gly Ala Lys Ser Ile Asn
        275                 280                 285

Asn Leu Lys Pro Gly Asp Asn Ile Leu Ile Ser Glu Ala Cys Thr His
        290                 295                 300

His Ser Leu Lys Gly Asp Ile Ala Lys Glu Lys Ile Pro Asn Leu Leu
305                 310                 315                 320

Lys Lys Lys Ile Gly Gly Glu Val Asn Ile Asp Phe Ser Ser Gly Glu
                325                 330                 335

Asp Phe Thr Lys Asn Ile Glu Lys Tyr Lys Leu Ile Ile His Cys Gly
            340                 345                 350

Gly Cys Met Leu Asn Gln Lys Gln Met Ile Asn Arg Leu Asn Lys Ala
        355                 360                 365

Asn Glu Lys Asn Ile Pro Ile Thr Asn Phe Gly Val Ala Leu Ala Tyr
    370                 375                 380

Leu Asn Gly Leu Leu Lys Arg Val Ser Glu Met Phe
385                 390                 395

<210> SEQ ID NO 21
<211> LENGTH: 309
<212> TYPE: PRT
<213> ORGANISM: desulfovbrio desulfuricans

<400> SEQUENCE: 21

Val Ala Leu Leu Val Ser Glu Ala Gly Met Glu Glu Ala Glu Lys
1               5                   10                  15

Arg Met Leu Ala Asp Leu Gln Ala Met Glu Ile Ser Ala Leu Val Val
            20                  25                  30

Phe Asn Lys Gln Asp Ile Ala Asp Val Arg Pro Glu Asp Val Arg Phe
        35                  40                  45

Cys His Glu Ala Gly Val Arg His Val Gln Val Ser Ser Val Ala Gln
    50                  55                  60

Lys Gly Ile Ser Glu Leu Lys Ser Ala Ile Val Glu Met Val Pro Glu
65                  70                  75                  80

Glu Leu Lys Ala Asp Pro Val Leu Val Ser Asp Leu Ile Ser Glu Gly
                85                  90                  95
```

```
Asp Thr Val Leu Cys Val Pro Ile Asp Leu Ala Ala Pro Lys Gly
            100                 105                 110

Arg Leu Ile Leu Pro Gln Val Gln Val Leu Arg Asp Val Leu Asp Ala
        115                 120                 125

Asp Ala Met Gly Met Val Val Lys Glu Arg Glu Leu Glu Ala Ala Leu
    130                 135                 140

Asp Lys Leu Val Ser Pro Pro Ala Leu Val Ile Thr Asp Ser Gln Val
145                 150                 155                 160

Val Leu Lys Val Ala Gly Asp Val Asp Asp Ile Pro Met Thr Thr
                165                 170                 175

Phe Ser Thr Leu Phe Ala Arg Tyr Lys Gly Asp Leu Glu Leu Leu Val
            180                 185                 190

Arg Gly Ala Arg Ala Ile Asp Ser Leu Arg Asp Gly Asp Thr Val Leu
        195                 200                 205

Met Cys Glu Ala Cys Ser His His Ala Val Ala Asp Asp Ile Gly Arg
    210                 215                 220

Val Lys Ile Pro Arg Trp Ile Thr Gln Tyr Thr Gly Arg Glu Leu Ser
225                 230                 235                 240

Phe Glu Met Tyr Ala Gly His Asp Phe Pro Glu Asp Leu Glu Arg Tyr
                245                 250                 255

Ala Leu Ala Val His Cys Gly Gly Cys Met Thr Asn Arg Ala Glu Met
            260                 265                 270

Met Arg Arg Ile Arg Glu Cys Thr Arg Gly Val Pro Val Thr Asn
        275                 280                 285

Tyr Gly Val Ala Ile Ser Lys Val Gln Gly Val Leu Glu Arg Val Val
290                 295                 300

Ala Pro Phe Gly Leu
305

<210> SEQ ID NO 22
<211> LENGTH: 394
<212> TYPE: PRT
<213> ORGANISM: shewanella oneidensis

<400> SEQUENCE: 22

Met Arg Tyr His Ile Ala Leu Val Gly Arg Arg Asn Ser Gly Lys Ser
1               5                   10                  15

Ser Leu Leu Asn Met Leu Ala Gly Gln Gln Ile Ser Ile Val Ser Asp
            20                  25                  30

Ile Lys Gly Thr Thr Thr Asp Ala Val Ala Lys Ala Tyr Glu Leu Gln
        35                  40                  45

Pro Leu Gly Pro Val Thr Phe Tyr Asp Thr Ala Gly Ile Asp Asp Glu
    50                  55                  60

Gly Thr Leu Gly Ala Met Arg Val Ser Ala Thr Arg Arg Val Leu Phe
65                  70                  75                  80

Arg Ser Asp Met Ala Leu Leu Val Val Asp Glu Gln Gly Leu Cys Pro
                85                  90                  95

Ser Asp Met Ala Leu Ile Asp Glu Ile Arg Gln Leu Gln Met Pro Ile
            100                 105                 110

Leu Met Val Phe Asn Lys Ala Asp Ile Cys Thr Pro Lys Ala Glu Asp
        115                 120                 125

Ile Ala Phe Cys Gln Asn Gln Ser Leu Pro Phe Ile Val Val Ser Ala
    130                 135                 140

Ala Thr Gly Leu Ala Gly Lys Gln Leu Lys Gln Leu Met Val Glu Leu
145                 150                 155                 160
```

```
Ala Pro Ala Glu Tyr Lys Gln Glu Pro Leu Leu Ala Gly Asp Leu Tyr
                165                 170                 175

Gln Ala Gly Asp Val Ile Leu Cys Val Val Pro Ile Asp Met Ala Ala
            180                 185                 190

Pro Lys Gly Arg Leu Ile Leu Pro Gln Val Gln Ile Leu Arg Glu Ala
        195                 200                 205

Leu Asp Arg Ser Ala Ile Ala Met Val Val Lys Glu Thr Glu Leu Ala
    210                 215                 220

Gln Ala Leu Ser Val Val Thr Pro Lys Leu Val Ile Ser Asp Ala Gln
225                 230                 235                 240

Ala Ile Lys Gln Val Ala Ile Val Pro Asp Ala Val Pro Leu Thr
                245                 250                 255

Thr Phe Ser Thr Leu Phe Ala Arg Phe Lys Gly Asp Leu Ala Ala Leu
            260                 265                 270

Ala Thr Gly Ala Asp Ala Leu Asp Thr Leu Gln Asp Gly Asp Lys Val
        275                 280                 285

Leu Ile Ser Glu Ala Cys Ser His Asn Val Gln Glu Asp Asp Ile Gly
    290                 295                 300

Arg Val Lys Leu Pro Arg Trp Ile Asn Ser Tyr Thr Gly Lys Gln Leu
305                 310                 315                 320

Glu Phe Val Val Thr Ser Gly His Asp Phe Pro Asn Asp Leu Glu Gln
                325                 330                 335

Tyr Ala Leu Val Ile His Cys Gly Ala Cys Met Phe Asn Arg Asn Glu
            340                 345                 350

Met Leu Arg Arg Ile Arg Glu Cys Gln Arg Arg Gln Val Pro Ile Thr
        355                 360                 365

Asn Tyr Gly Val Ala Ile Ser Lys Leu Gln Gly Val Leu Pro Arg Val
    370                 375                 380

Leu Thr Pro Phe Asn Arg Asn Pro Gln Gln
385                 390

<210> SEQ ID NO 23
<211> LENGTH: 567
<212> TYPE: PRT
<213> ORGANISM: Chlamydomonas reinhardtii

<400> SEQUENCE: 23

Met Ser Val Pro Leu Gln Cys Asn Ala Gly Arg Leu Leu Ala Gly Gln
1               5                   10                  15

Arg Pro Cys Gly Val Arg Ala Arg Leu Asn Arg Arg Val Cys Val Pro
            20                  25                  30

Val Thr Ala His Gly Lys Ala Ser Ala Thr Arg Glu Tyr Ala Gly Asp
        35                  40                  45

Phe Leu Pro Gly Thr Thr Ile Ser His Ala Trp Ser Val Glu Arg Glu
    50                  55                  60

Thr His His Arg Tyr Arg Asn Pro Ala Glu Trp Ile Asn Glu Ala Ala
65                  70                  75                  80

Ile His Lys Ala Leu Glu Thr Ser Lys Ala Asp Ala Gln Asp Ala Gly
                85                  90                  95

Arg Val Arg Glu Ile Leu Ala Lys Ala Lys Glu Lys Ala Phe Val Thr
            100                 105                 110

Glu His Ala Pro Val Asn Ala Glu Ser Lys Ser Glu Phe Val Gln Gly
        115                 120                 125

Leu Thr Leu Glu Glu Cys Ala Thr Leu Ile Asn Val Asp Ser Asn Asn
```

```
                    130                 135                 140
Val Glu Leu Met Asn Glu Ile Phe Asp Thr Ala Leu Ala Ile Lys Glu
145                 150                 155                 160

Arg Ile Tyr Gly Asn Arg Val Val Leu Phe Ala Pro Leu Tyr Ile Ala
                165                 170                 175

Asn His Cys Met Asn Thr Cys Thr Tyr Cys Ala Phe Arg Ser Ala Asn
            180                 185                 190

Lys Gly Met Glu Arg Ser Ile Leu Thr Asp Asp Leu Arg Glu Glu
        195                 200                 205

Val Ala Ala Leu Gln Arg Gln Gly His Arg Arg Ile Leu Ala Leu Thr
    210                 215                 220

Gly Glu His Pro Lys Tyr Thr Phe Asp Asn Phe Leu His Ala Val Asn
225                 230                 235                 240

Val Ile Ala Ser Val Lys Thr Glu Pro Glu Gly Ser Ile Arg Arg Ile
                245                 250                 255

Asn Val Glu Ile Pro Pro Leu Ser Val Ser Asp Met Arg Arg Leu Lys
            260                 265                 270

Asn Thr Asp Ser Val Gly Thr Phe Val Leu Phe Gln Glu Thr Tyr His
        275                 280                 285

Arg Asp Thr Phe Lys Val Met His Pro Ser Gly Pro Lys Ser Asp Phe
    290                 295                 300

Asp Phe Arg Val Leu Thr Gln Asp Arg Ala Met Arg Ala Gly Leu Asp
305                 310                 315                 320

Asp Val Gly Ile Gly Ala Leu Phe Gly Leu Tyr Asp Tyr Arg Tyr Glu
                325                 330                 335

Val Cys Ala Met Leu Met His Ser Glu His Leu Glu Arg Glu Tyr Asn
            340                 345                 350

Ala Gly Pro His Thr Ile Ser Val Pro Arg Met Arg Pro Ala Asp Gly
        355                 360                 365

Ser Glu Leu Ser Ile Ala Pro Pro Tyr Pro Val Asn Asp Ala Asp Phe
    370                 375                 380

Met Lys Leu Val Ala Val Leu Arg Ile Ala Val Pro Tyr Thr Gly Met
385                 390                 395                 400

Ile Leu Ser Thr Arg Glu Ser Pro Glu Met Arg Ser Ala Leu Leu Lys
                405                 410                 415

Cys Gly Met Ser Gln Met Ser Ala Gly Ser Arg Thr Asp Val Gly Ala
            420                 425                 430

Tyr His Lys Asp His Thr Leu Ser Thr Glu Ala Asn Leu Ser Lys Leu
        435                 440                 445

Ala Gly Gln Phe Thr Leu Gln Asp Glu Arg Pro Thr Asn Glu Ile Val
    450                 455                 460

Lys Trp Leu Met Glu Glu Gly Tyr Val Pro Ser Trp Cys Thr Ala Cys
465                 470                 475                 480

Tyr Arg Gln Gly Arg Thr Gly Glu Asp Phe Met Asn Ile Cys Lys Ala
                485                 490                 495

Gly Asp Ile His Asp Phe Cys His Pro Asn Ser Leu Leu Thr Leu Gln
            500                 505                 510

Glu Tyr Leu Met Asp Tyr Ala Asp Pro Asp Leu Arg Lys Lys Gly Glu
        515                 520                 525

Gln Val Ile Ala Arg Glu Met Gly Pro Asp Ala Ser Glu Pro Leu Ser
    530                 535                 540

Ala Gln Ser Arg Lys Arg Leu Glu Arg Lys Met Lys Gln Val Leu Glu
545                 550                 555                 560
```

Gly Glu His Asp Val Tyr Leu
                565

<210> SEQ ID NO 24
<211> LENGTH: 473
<212> TYPE: PRT
<213> ORGANISM: Thermotoga maritima

<400> SEQUENCE: 24

Met Cys Met Tyr Val Phe Val Lys Glu Arg Val Glu Ser Arg Ser Phe
1               5                   10                  15

Ile Pro Glu Glu Lys Ile Phe Glu Leu Leu Lys Thr Lys Asn Pro
            20                  25                  30

Asp Pro Ala Arg Val Arg Glu Ile Ile Gln Lys Ser Leu Asp Lys Asn
            35                  40                  45

Arg Leu Glu Pro Glu Glu Thr Ala Thr Leu Leu Asn Val Glu Asp Pro
        50                  55                  60

Glu Leu Leu Glu Glu Ile Phe Gly Ala Ala Arg Thr Leu Lys Glu Arg
65                  70                  75                  80

Ile Tyr Gly Asn Arg Ile Val Leu Phe Ala Pro Leu Tyr Ile Gly Asn
                85                  90                  95

Asp Cys Ile Asn Asp Cys Val Tyr Cys Gly Phe Arg Val Ser Asn Lys
            100                 105                 110

Val Val Glu Arg Arg Thr Leu Thr Glu Glu Gln Leu Lys Glu Val
            115                 120                 125

Lys Ala Leu Val Ser Gln Gly His Lys Arg Leu Ile Val Val Tyr Gly
        130                 135                 140

Glu His Pro Asn Tyr Ser Pro Glu Phe Ile Ala Arg Thr Ile Asp Ile
145                 150                 155                 160

Val Tyr Asn Thr Lys Tyr Gly Asn Gly Glu Ile Arg Arg Val Asn Val
                165                 170                 175

Asn Ala Ala Pro Gln Thr Ile Glu Gly Tyr Lys Ile Ile Lys Ser Val
            180                 185                 190

Gly Ile Gly Thr Phe Gln Ile Phe Gln Glu Thr Tyr His Arg Glu Thr
        195                 200                 205

Tyr Leu Lys Leu His Pro Arg Gly Pro Lys Ser Asn Tyr Asn Trp Arg
    210                 215                 220

Leu Tyr Gly Leu Asp Arg Ala Met Met Ala Gly Ile Asp Asp Val Gly
225                 230                 235                 240

Ile Gly Ala Leu Phe Gly Leu Tyr Asp Trp Lys Phe Glu Val Met Gly
                245                 250                 255

Leu Leu Tyr His Thr Ile His Leu Glu Glu Arg Phe Gly Val Gly Pro
            260                 265                 270

His Thr Ile Ser Phe Pro Arg Ile Lys Pro Ala Ile Asn Thr Pro Tyr
        275                 280                 285

Ser Gln Lys Pro Glu His Val Ser Asp Glu Asp Phe Lys Lys Leu
    290                 295                 300

Val Ala Ile Ile Arg Leu Ser Val Pro Tyr Thr Gly Met Ile Leu Thr
305                 310                 315                 320

Ala Arg Glu Pro Ala Lys Leu Arg Asp Glu Val Ile Lys Leu Gly Val
                325                 330                 335

Ser Gln Ile Asp Ala Gly Ser Arg Ile Gly Ile Gly Ala Tyr Ser His
            340                 345                 350

Lys Glu Asp Asp Glu Asp Arg Lys Arg Gln Phe Thr Leu Glu Asp Pro

```
                        355                 360                 365
Arg Pro Leu Asp Gln Val Met Arg Ser Leu Leu Lys Glu Gly Phe Val
370                 375                 380

Pro Ser Phe Cys Thr Ala Cys Tyr Arg Ala Gly Arg Thr Gly Glu His
385                 390                 395                 400

Phe Met Glu Phe Ala Ile Pro Gly Phe Val Lys Asn Phe Cys Thr Pro
                405                 410                 415

Asn Ala Leu Phe Thr Leu Gln Glu Tyr Leu Cys Asp Tyr Ala Thr Glu
                420                 425                 430

Glu Thr Arg Lys Val Gly Glu Val Ile Glu Arg Glu Leu Gln Lys
                435                 440                 445

Met Asn Pro Lys Ile Arg Glu Arg Val Arg Glu Gly Leu Glu Lys Ile
450                 455                 460

Lys Arg Gly Glu Arg Asp Val Arg Phe
465                 470

<210> SEQ ID NO 25
<211> LENGTH: 473
<212> TYPE: PRT
<213> ORGANISM: Clostridium thermocellum

<400> SEQUENCE: 25

Met Cys Arg Tyr Lys Val Cys Lys Leu Lys Val Gly Asp Ile Gln Met
1               5                   10                  15

Val Glu Lys Val Asp Phe Ile Lys Glu Asp Leu Ile Phe Ser Leu Leu
                20                  25                  30

Glu Lys Gly Lys Ile Thr Asp Arg Asn Glu Ile Arg Glu Ile Leu Ala
            35                  40                  45

Lys Ala Arg Glu Cys Lys Gly Ile Ser Leu Gly Glu Val Ala Lys Leu
50                  55                  60

Leu Tyr Leu Glu Asp Glu Glu Leu Leu Glu Glu Leu Tyr Asp Val Ala
65                  70                  75                  80

Lys Tyr Ile Lys Asn Lys Ile Tyr Gly Lys Arg Val Val Leu Phe Ala
                85                  90                  95

Pro Leu Tyr Thr Ser Asn Glu Cys Thr Asn Asn Cys Leu Tyr Cys Gly
            100                 105                 110

Phe Arg His Asp Asn Lys Glu Leu His Arg Lys Thr Leu Ser Leu Glu
        115                 120                 125

Glu Ile Val Glu Glu Ala Lys Ala Ile Glu Arg Gln Gly His Lys Arg
130                 135                 140

Leu Leu Leu Ile Cys Gly Glu Asp Pro Arg Lys Thr Asn Val Lys His
145                 150                 155                 160

Phe Thr Asp Ala Met Glu Ala Ile Tyr Lys Ser Thr Asp Ile Arg Arg
                165                 170                 175

Ile Asn Val Glu Ala Ala Pro Met Thr Val Glu Asp Tyr Arg Glu Leu
            180                 185                 190

Lys Lys Ala Gly Ile Gly Thr Tyr Val Ile Phe Gln Glu Thr Tyr His
        195                 200                 205

Arg Glu Thr Tyr Arg Ile Met His Pro Val Gly Lys Lys Ala Asn Tyr
210                 215                 220

Asp Trp Arg Ile Thr Ala Ile Asp Arg Ala Phe Glu Gly Gly Ile Asp
225                 230                 235                 240

Asp Val Gly Val Gly Ala Leu Phe Gly Leu Tyr Asp Tyr Arg Phe Glu
                245                 250                 255
```

Val Leu Gly Leu Leu Met His Cys Met His Phe Glu Glu Lys Tyr Gly
            260                 265                 270

Val Gly Pro His Thr Ile Ser Val Pro Arg Leu Arg Pro Ala Leu Gly
            275                 280                 285

Ala Pro Leu Lys Glu Ile Pro Tyr Lys Val Thr Asp Lys Asp Phe Lys
        290                 295                 300

Lys Ile Val Ala Ile Phe Arg Ile Ala Val Pro Tyr Thr Gly Ile Ile
305                 310                 315                 320

Leu Ser Thr Arg Glu Arg Ala Glu Phe Arg Asp Glu Leu Leu Ser Val
                325                 330                 335

Gly Val Ser Gln Ile Ser Ala Gly Ser Lys Thr Asn Pro Gly Gly Tyr
            340                 345                 350

Gln Glu Asp Asp Asp His Ala Asp Gln Phe Glu Ile Ser Asp Asn Arg
        355                 360                 365

Ser Leu Pro Lys Val Met Glu Thr Ile Cys Gln Gln Gly Tyr Ile Pro
    370                 375                 380

Ser Phe Cys Thr Ala Cys Tyr Arg Arg Cys Arg Thr Gly Glu His Phe
385                 390                 395                 400

Met Glu Tyr Ala Lys Ala Gly Asp Ile His Glu Phe Cys Gln Pro Asn
                405                 410                 415

Ala Ile Leu Thr Phe Lys Glu Asn Leu Met Asp Tyr Ala Asp Glu Pro
            420                 425                 430

Leu Arg Lys Met Gly Glu Glu Val Ile Leu Lys Ala Leu Glu Glu Ile
        435                 440                 445

Glu Asp Glu Lys Met Lys Thr Leu Thr Ile Ala Lys Leu Glu Glu Ile
450                 455                 460

Glu Lys Gly Lys Arg Asp Ile Tyr Phe
465                 470

<210> SEQ ID NO 26
<211> LENGTH: 478
<212> TYPE: PRT
<213> ORGANISM: Clostridium tetani

<400> SEQUENCE: 26

Met Ile Cys Lys Met Lys Glu Ile Lys Lys Met Lys Ala Glu Glu Phe
1               5                   10                  15

Ile Ile His Ser Asp Ile Glu Lys Ala Leu Asp Lys Gly Arg Glu Lys
            20                  25                  30

Ala Lys Asn Lys Asp Tyr Val Arg Glu Leu Leu Asn Lys Ala Leu Glu
        35                  40                  45

Cys Lys Gly Leu Thr Tyr Glu Glu Gly Ala Val Leu Leu Asn Val Glu
    50                  55                  60

Asp Glu His Ile Leu Glu Asp Ile Tyr Lys Ala Lys Ile Ile Lys
65                  70                  75                  80

Glu Lys Ile Tyr Gly Lys Arg Ile Val Leu Phe Ala Pro Leu Tyr Ile
                85                  90                  95

Ser Ser Tyr Cys Val Asn Asn Cys Lys Tyr Cys Gly Tyr Lys Cys Ser
            100                 105                 110

Asn Asn Thr Phe Lys Arg Asn Lys Leu Thr Met Asp Glu Ile Ala Glu
        115                 120                 125

Glu Val Lys Ile Leu Glu Ser Leu Gly His Lys Arg Leu Ala Leu Glu
    130                 135                 140

Val Gly Glu Asp Asp Val Asn Cys Ser Ile Asp Tyr Val Leu Lys Ser
145                 150                 155                 160

```
Ile Lys Lys Ile Tyr Ser Leu Lys Phe Asn Asn Gly Ser Ile Arg Arg
            165                 170                 175

Ile Asn Val Asn Ile Ala Ala Thr Thr Ile Glu Asn Tyr Lys Lys Leu
            180                 185                 190

Lys Glu Ala Glu Ile Gly Thr Tyr Ile Leu Phe Gln Glu Thr Tyr His
            195                 200                 205

Lys Glu Thr Tyr Glu Lys Met His Pro Thr Gly Pro Lys Ser Asp Tyr
210                 215                 220

Asn Tyr His Thr Thr Ala Met Asp Arg Ala Arg Met Ala Gly Ile Asp
225                 230                 235                 240

Asp Val Gly Ile Gly Val Leu Tyr Gly Leu Tyr Asp Tyr Lys Tyr Asp
                245                 250                 255

Thr Val Ala Met Leu Met His Gly Glu His Leu Glu Lys Ala Thr Gly
                260                 265                 270

Val Gly Pro His Thr Ile Ser Val Pro Arg Leu Arg Glu Ala Val Gly
            275                 280                 285

Met Thr Leu Lys Glu Tyr Pro His Leu Val Lys Asp Glu Asp Phe Lys
            290                 295                 300

Lys Ile Val Ala Ile Leu Arg Leu Ser Val Pro Tyr Thr Gly Ile Ile
305                 310                 315                 320

Leu Ser Thr Arg Glu Glu Ala Asp Phe Arg Glu Lys Val Ile Ala Leu
                325                 330                 335

Gly Val Ser Gln Ile Ser Ala Gly Ser Cys Thr Gly Val Gly Gly Tyr
            340                 345                 350

Ser Lys Glu Asn Asn Ile Lys His Lys Asp Glu Lys Pro Gln Phe Glu
            355                 360                 365

Leu Gly Asp Asn Arg Ser Pro Ile Glu Val Ile Lys Ser Ile Cys Lys
            370                 375                 380

Ser Gly Tyr Ile Pro Ser Tyr Cys Thr Ala Cys Tyr Arg Glu Gly Arg
385                 390                 395                 400

Thr Gly Glu Arg Phe Met Ser Leu Ala Lys Thr Gly Glu Ile Gln Asn
                405                 410                 415

Val Cys His Pro Asn Ala Ile Leu Thr Phe Lys Glu Phe Leu Leu Asp
            420                 425                 430

Tyr Gly Asp Lys Glu Ala Lys Asp Leu Gly Glu Glu Leu Ile Arg Lys
            435                 440                 445

Ser Leu Glu Asp Ile Pro Asn Glu Lys Ile Lys Met Thr Glu Glu
450                 455                 460

Lys Leu Glu Arg Ile Glu Ser Gly Glu Arg Asp Leu Arg Phe
465                 470                 475

<210> SEQ ID NO 27
<211> LENGTH: 469
<212> TYPE: PRT
<213> ORGANISM: desulfovbrio desulfuricans

<400> SEQUENCE: 27

Met Ser Phe Asp Ser Arg Ser Leu Pro Gly Phe Ile Asp Glu Glu Lys
1               5                   10                  15

Ile Glu Ser Val Ile Ala Ala Thr Ala Lys Pro Asp Ala Val Arg Val
            20                  25                  30

Arg Glu Ile Leu Ala Lys Ala Arg Glu Ala Lys Gly Leu Asp Ala Glu
        35                  40                  45

Glu Thr Ala Thr Leu Leu Gln Leu Asp Asn Glu Glu Leu Asp Ala Glu
```

```
                50                  55                  60
Leu Phe Ala Thr Ala Lys Lys Val Lys Gln Thr Ile Tyr Gly Asn Arg
 65                  70                  75                  80

Leu Val Leu Phe Ala Pro Leu Tyr Ile Thr Asn Glu Cys Tyr Asn Arg
                     85                  90                  95

Cys Ala Tyr Cys Gly Phe Asn Ala Thr Asn Ser Asp Leu Lys Arg Arg
                100                 105                 110

Thr Leu Ser Glu Asp Glu Ile Arg Ala Glu Val Glu Val Leu Glu Arg
            115                 120                 125

Leu Gly His Lys Arg Leu Leu Leu Val Tyr Gly Glu His Pro Arg Leu
        130                 135                 140

Asp Ala Asp Trp Met Ala Arg Thr Ile Gln Val Val Tyr Asp Thr Val
145                 150                 155                 160

Ser Glu Lys Ser Gly Glu Ile Arg Arg Val Asn Ile Asn Cys Ala Pro
                165                 170                 175

Gln Thr Val Asp Gly Phe Arg Lys Leu His Asp Val Gly Ile Gly Thr
                180                 185                 190

Tyr Gln Cys Phe Gln Glu Thr Tyr His Lys Ala Thr Tyr Asp Lys Ala
                195                 200                 205

His Leu Gly Gly Pro Lys Lys Asp Tyr Leu Trp Arg Leu Tyr Ala Met
        210                 215                 220

His Arg Ala Met Glu Ala Gly Ile Asp Asp Val Gly Met Gly Pro Leu
225                 230                 235                 240

Leu Gly Leu Tyr Asp Tyr Arg Phe Glu Ile Leu Ala Leu Met Gln His
                245                 250                 255

Ala Ala Asp Leu Glu Lys His Phe Gly Val Gly Pro His Thr Ile Ser
                260                 265                 270

Phe Pro Arg Leu Glu Pro Ala Leu Asn Ala Asp Met Ala Phe Asn Pro
            275                 280                 285

Pro His Pro Leu Thr Asp Ser Gln Phe Lys Arg Met Val Ala Val Leu
        290                 295                 300

Arg Leu Ala Val Pro Tyr Thr Gly Leu Ile Leu Ser Thr Arg Glu Asn
305                 310                 315                 320

Ala Ala Met Arg Arg Glu Leu Leu Glu Leu Gly Val Ser Gln Ile Ser
                325                 330                 335

Ala Gly Ser Arg Thr Tyr Pro Gly Ala Tyr Ser Asp Pro Ser Tyr Asp
            340                 345                 350

Arg Pro Asp Val Gln Gln Phe Cys Val Gly Asp Ser Arg Ser Leu Asp
        355                 360                 365

Glu Val Ile Ala Glu Leu Val Ser Leu Gly Tyr Leu Pro Ser Trp Cys
370                 375                 380

Thr Ala Cys Tyr Arg Leu Gly Arg Thr Gly His Phe Met Glu Leu
385                 390                 395                 400

Ala Lys Lys Gly Phe Ile Gln Glu Phe Cys His Pro Asn Ala Leu Leu
                405                 410                 415

Thr Phe Asn Glu Tyr Leu His Asp Tyr Ala Ser Glu Ser Thr Arg Glu
            420                 425                 430

Ala Gly Arg Lys Leu Ile Glu Lys Glu Ala Ala Gly Cys Pro Glu Asn
        435                 440                 445

Arg Arg Glu Leu Val Ala Ser Arg Leu Gln Arg Ile Asp Gly Gly Glu
450                 455                 460

Arg Asp Leu Tyr Ile
465
```

<210> SEQ ID NO 28
<211> LENGTH: 479
<212> TYPE: PRT
<213> ORGANISM: shewanella oneidensis

<400> SEQUENCE: 28

| | | | | | | | | | | | | | | |
|---|---|---|---|---|---|---|---|---|---|---|---|---|---|---|
| Met | Ser | Thr | His | Glu | His | His | Ser | Ile | Thr | Leu | Ser | Asp | Tyr | Asn | Pro |
| 1 | | | | 5 | | | | | 10 | | | | | 15 | |
| Asn | Val | Asn | Phe | Ile | Asp | Asp | Lys | Ala | Ile | Trp | Gln | Thr | Ile | Glu | Asp |
| | | | 20 | | | | | 25 | | | | | 30 | | |
| Ala | Ser | Asp | Pro | Ser | Arg | Glu | Gln | Val | Leu | Ala | Ile | Leu | Asp | Lys | Ala |
| | | 35 | | | | | 40 | | | | | 45 | | | |
| Arg | Gln | Cys | Glu | Gly | Leu | Ser | Ile | Ser | Glu | Thr | Ala | Leu | Leu | Leu | Gln |
| | 50 | | | | | 55 | | | | | 60 | | | | |
| Asn | Gln | Asp | Lys | Thr | Leu | Asp | Glu | Met | Leu | Phe | Ser | Val | Ala | Arg | Glu |
| 65 | | | | | 70 | | | | | 75 | | | | | 80 |
| Ile | Lys | Asn | Thr | Ile | Tyr | Gly | Asn | Arg | Ile | Val | Met | Phe | Ala | Pro | Leu |
| | | | | 85 | | | | | 90 | | | | | 95 | |
| Tyr | Val | Ser | Asn | His | Cys | Ala | Asn | Ser | Cys | Ser | Tyr | Cys | Gly | Phe | Asn |
| | | | 100 | | | | | 105 | | | | | 110 | | |
| Ala | Asp | Asn | His | Glu | Leu | Lys | Arg | Lys | Thr | Leu | Lys | Gln | Asp | Glu | Ile |
| | | 115 | | | | | 120 | | | | | 125 | | | |
| Arg | Gln | Glu | Val | Ala | Ile | Leu | Glu | Glu | Met | Gly | His | Lys | Arg | Ile | Leu |
| | 130 | | | | | 135 | | | | | 140 | | | | |
| Ala | Val | Tyr | Gly | Glu | His | Pro | Arg | Asn | Val | Gln | Ala | Ile | Val | Glu | Glu |
| 145 | | | | | 150 | | | | | 155 | | | | | 160 |
| Ser | Ile | Gln | Thr | Met | Tyr | Ser | Val | Lys | Gln | Gly | Lys | Gly | Glu | Ile | |
| | | | | 165 | | | | | 170 | | | | | 175 | |
| Arg | Arg | Ile | Asn | Val | Asn | Cys | Ala | Pro | Met | Ser | Val | Glu | Asp | Phe | Lys |
| | | | 180 | | | | | 185 | | | | | 190 | | |
| Gln | Leu | Lys | Thr | Ala | Ala | Ile | Gly | Thr | Tyr | Gln | Cys | Phe | Gln | Glu | Thr |
| | | 195 | | | | | 200 | | | | | 205 | | | |
| Tyr | His | Gln | Asp | Thr | Tyr | Ser | Gln | Val | His | Leu | Lys | Gly | Lys | Lys | Thr |
| | 210 | | | | | 215 | | | | | 220 | | | | |
| Asp | Phe | Leu | Tyr | Arg | Leu | Tyr | Ala | Met | His | Arg | Ala | Met | Glu | Ala | Gly |
| 225 | | | | | 230 | | | | | 235 | | | | | 240 |
| Ile | Asp | Asp | Val | Gly | Ile | Gly | Ala | Leu | Phe | Gly | Leu | Tyr | Asp | His | Arg |
| | | | | 245 | | | | | 250 | | | | | 255 | |
| Phe | Glu | Leu | Leu | Ala | Met | Leu | Thr | His | Val | Gln | Gln | Leu | Glu | Lys | Asp |
| | | | 260 | | | | | 265 | | | | | 270 | | |
| Cys | Gly | Val | Gly | Pro | His | Thr | Ile | Ser | Phe | Pro | Arg | Ile | Glu | Pro | Ala |
| | | 275 | | | | | 280 | | | | | 285 | | | |
| His | Gly | Ser | Ala | Ile | Ser | Glu | Lys | Pro | Pro | Tyr | Glu | Val | Asp | Asp | Asp |
| | 290 | | | | | 295 | | | | | 300 | | | | |
| Cys | Phe | Lys | Arg | Ile | Val | Ala | Ile | Thr | Arg | Leu | Ala | Val | Pro | Tyr | Thr |
| 305 | | | | | 310 | | | | | 315 | | | | | 320 |
| Gly | Leu | Ile | Met | Ser | Thr | Arg | Glu | Ser | Ala | Ala | Leu | Arg | Lys | Glu | Leu |
| | | | | 325 | | | | | 330 | | | | | 335 | |
| Leu | Glu | Leu | Gly | Val | Ser | Gln | Ile | Ser | Ala | Gly | Ser | Arg | Thr | Ala | Pro |
| | | | 340 | | | | | 345 | | | | | 350 | | |
| Gly | Gly | Tyr | Gln | Asp | Ser | Lys | Gln | Asn | Gln | His | Asp | Ala | Glu | Gln | Phe |
| | | 355 | | | | | 360 | | | | | 365 | | | |
| Ser | Leu | Gly | Asp | His | Arg | Glu | Met | Asp | Glu | Ile | Ile | Tyr | Glu | Leu | Val |

```
            370                 375                 380
Thr Asp Ser Asp Ala Ile Pro Ser Phe Cys Thr Gly Cys Tyr Arg Lys
385                 390                 395                 400

Gly Arg Thr Gly Asp His Phe Met Gly Leu Ala Lys Gln Gln Phe Ile
            405                 410                 415

Gly Lys Phe Cys Gln Pro Asn Ala Leu Ile Thr Phe Lys Glu Tyr Leu
                420                 425                 430

Asn Asp Tyr Ala Ser Glu Lys Thr Arg Glu Ala Gly Asn Ala Leu Ile
            435                 440                 445

Glu Arg Glu Leu Ala Lys Met Ser Pro Ser Arg Ala Arg Asn Val Arg
        450                 455                 460

Gly Cys Leu Gln Lys Thr Asp Ala Gly Glu Arg Asp Ile Tyr Leu
465                 470                 475

<210> SEQ ID NO 29
<211> LENGTH: 472
<212> TYPE: PRT
<213> ORGANISM: Bacteroides thetaiotaomicron

<400> SEQUENCE: 29

Met Tyr Lys Val Asp Ser Pro Gln Ala Glu Glu Phe Ile His His Glu
1               5                   10                  15

Glu Ile Leu Glu Thr Leu Glu Tyr Ala Trp Ser His Lys Asp Asn Arg
            20                  25                  30

Ala Phe Ile Glu Gln Leu Ile Glu Lys Ala Ala Leu Cys Lys Gly Leu
        35                  40                  45

Thr His Arg Glu Ala Ala Thr Leu Leu Glu Cys Asp Gln Pro Asp Leu
    50                  55                  60

Ile Glu Arg Ile Phe His Leu Ala Lys Glu Ile Lys Gln Lys Phe Tyr
65                  70                  75                  80

Gly Asn Arg Ile Val Met Phe Ala Pro Leu Tyr Leu Ser Asn Tyr Cys
                85                  90                  95

Val Asn Gly Cys Val Tyr Cys Pro Tyr His Ala Lys Asn Lys Thr Ile
            100                 105                 110

Ala Arg Lys Lys Leu Thr Gln Glu Ile Arg Lys Glu Val Ile Ala
        115                 120                 125

Leu Gln Asp Met Gly His Lys Arg Leu Ala Leu Glu Ala Gly Glu His
    130                 135                 140

Pro Thr Leu Asn Ser Leu Glu Tyr Ile Leu Glu Ser Ile Arg Thr Ile
145                 150                 155                 160

Tyr Ser Ile Arg His Lys Asn Gly Ala Ile Arg Arg Val Asn Val Asn
                165                 170                 175

Ile Ala Ala Thr Thr Val Glu Asn Tyr Arg Arg Leu Lys Asp Ala Gly
            180                 185                 190

Ile Gly Thr Tyr Ile Leu Phe Gln Glu Thr Tyr His Lys Lys Asn Tyr
        195                 200                 205

Glu Ala Leu His Pro Thr Gly Pro Lys Ser Asn Tyr Ala Tyr His Thr
    210                 215                 220

Glu Ala Met Asp Arg Ala Met Glu Gly Gly Ile Asp Asp Val Gly Met
225                 230                 235                 240

Gly Val Leu Phe Gly Leu Asn Thr Tyr Arg Tyr Asp Phe Val Gly Leu
                245                 250                 255

Leu Met His Ala Glu His Leu Glu Ala Arg Phe Gly Val Gly Pro His
            260                 265                 270
```

```
Thr Ile Ser Val Pro Arg Ile Cys Ser Ala Asp Ile Asp Ala Gly
                275                 280                 285

Asp Phe Pro Asn Ala Ile Ser Asp Asp Ile Phe Ser Lys Ile Val Ala
290                 295                 300

Val Ile Arg Ile Ala Val Pro Tyr Thr Gly Met Ile Ile Ser Thr Arg
305                 310                 315                 320

Glu Ser Gln Glu Ser Arg Glu Lys Val Leu Glu Leu Gly Ile Ser Gln
                325                 330                 335

Ile Ser Gly Gly Ser Arg Thr Ser Val Gly Gly Tyr Ala Glu Thr Glu
                340                 345                 350

Leu Pro Glu Asp Asn Ser Ala Gln Phe Asp Val Ser Asp Thr Arg Thr
                355                 360                 365

Leu Asp Glu Val Val Asn Trp Leu Leu Glu Ser Gly Tyr Ile Pro Ser
370                 375                 380

Phe Cys Thr Ala Cys Tyr Arg Glu Gly Arg Thr Gly Asp Arg Phe Met
385                 390                 395                 400

Ser Leu Val Lys Ser Gly Gln Ile Ala Asn Cys Cys Gly Pro Asn Ala
                405                 410                 415

Leu Met Thr Leu Lys Glu Tyr Leu Glu Asp Tyr Ala Ser Glu Asp Thr
                420                 425                 430

Arg Ile Lys Gly Met Lys Leu Ile Ala Lys Glu Thr Asp Arg Ile Pro
                435                 440                 445

Asn Pro Lys Ile Arg Glu Ile Ala Ile Arg Asn Leu Lys Asp Ile Ala
                450                 455                 460

Glu Gly Lys Arg Asp Phe Arg Phe
465                 470

<210> SEQ ID NO 30
<211> LENGTH: 473
<212> TYPE: PRT
<213> ORGANISM: clostridium perfringens

<400> SEQUENCE: 30

Met Leu Lys Asp Asn Glu Lys Tyr Asn Ala Leu Asp Phe Ile Lys Asp
1               5                   10                  15

Asp Glu Ile Asn Ser Leu Ile Ala Lys Gly Lys Glu Leu Val Ser Asp
                20                  25                  30

Lys Glu Leu Val Arg Glu Ile Glu Lys Ser Lys Ser Ala Glu Gly
                35                  40                  45

Leu Thr Pro Glu Glu Thr Ala Val Leu Leu Asn Leu Glu Asp Lys Glu
50                  55                  60

Leu Ile Glu Glu Met Phe Lys Ala Ala Arg Gln Val Lys Glu Lys Leu
65                  70                  75                  80

Tyr Gly Lys Arg Leu Val Val Phe Ala Pro Leu Tyr Val Ser Asn Tyr
                85                  90                  95

Cys Val Asn Asn Cys Thr Tyr Cys Gly Tyr Lys His Cys Asn Asp Glu
                100                 105                 110

Leu Lys Arg Lys Lys Leu Asn Lys Glu Gln Leu Ile Glu Glu Val Lys
                115                 120                 125

Val Leu Glu Ser Leu Gly His Lys Arg Ile Ala Leu Glu Ala Gly Glu
                130                 135                 140

Asp Pro Val Asn Ala Pro Leu Asp Tyr Ile Leu Asp Cys Ile Lys Ser
145                 150                 155                 160

Ile Tyr Ser Ile Lys Phe Asp Asn Gly Ser Ile Arg Arg Ile Asn Val
                165                 170                 175
```

```
Asn Ile Ala Ala Thr Thr Val Glu Asn Tyr Lys Arg Leu Lys Asp Ala
            180                 185                 190

Glu Ile Gly Thr Tyr Ile Leu Phe Gln Glu Thr Tyr His Lys Pro Thr
        195                 200                 205

Tyr Glu Lys Leu His Val Ser Gly Pro Lys His Asn Tyr Asn Tyr His
    210                 215                 220

Thr Thr Ala Met His Arg Ala Arg Glu Ala Gly Ile Asp Asp Ile Gly
225                 230                 235                 240

Met Gly Val Leu Tyr Gly Leu Tyr Asp Tyr Lys Tyr Glu Thr Leu Ala
                245                 250                 255

Met Leu Met His Ala Met Asp Leu Glu Glu Thr Thr Gly Val Gly Pro
            260                 265                 270

His Thr Leu Ser Val Pro Arg Ile Arg Pro Ala Glu Asn Val Ser Leu
        275                 280                 285

Glu Asn Tyr Pro Tyr Leu Val Asp Asp Glu Asp Phe Lys Lys Ile Val
    290                 295                 300

Ala Ile Leu Arg Leu Ala Val Pro Tyr Ala Gly Leu Ile Leu Ser Thr
305                 310                 315                 320

Arg Glu Glu Pro Gly Leu Arg Asp Glu Ile Ile Ala Leu Gly Val Ser
                325                 330                 335

Gln Val Ser Thr Gly Ser Cys Thr Gly Val Gly Gly Tyr Ser Glu Ser
            340                 345                 350

Tyr Ile Asp Pro Glu Glu Lys Pro Gln Phe Glu Val Gly Asp His Arg
        355                 360                 365

Ser Pro Val Glu Met Ile Glu Ser Leu Met Glu Ala Gly Tyr Ile Pro
    370                 375                 380

Ser Tyr Cys Thr Ala Cys Tyr Arg Glu Gly Arg Thr Gly Glu Arg Phe
385                 390                 395                 400

Met Asp Ile Val Lys Ser Gly Glu Leu Tyr Lys Ile Cys Glu Ala Asn
                405                 410                 415

Ala Leu Ile Thr Leu Lys Glu Phe Ile Asp Asp Tyr Gly Thr Asp Arg
            420                 425                 430

Thr Arg Glu Ile Gly Asp Lys Leu Ile Lys Lys Ser Ile Asp Glu Ile
        435                 440                 445

Asp Asn Glu Ser Phe Arg Lys Ser Val Lys Glu Lys Ile Asn Lys Ile
    450                 455                 460

Ser Lys Gly Thr Arg Asp Leu Arg Phe
465                 470

<210> SEQ ID NO 31
<211> LENGTH: 472
<212> TYPE: PRT
<213> ORGANISM: Clostridium acetobutylicum

<400> SEQUENCE: 31

Met Tyr Asn Val Lys Ser Lys Val Ala Thr Glu Phe Ile Ser Asp Glu
1               5                   10                  15

Glu Ile Ile Asp Ser Leu Glu Tyr Ala Lys Gln Asn Lys Ser Asn Arg
            20                  25                  30

Glu Leu Ile Asp Ser Ile Ile Glu Lys Ala Lys Glu Cys Lys Gly Leu
        35                  40                  45

Thr His Arg Asp Ala Ala Val Leu Leu Glu Cys Asp Leu Glu Asp Glu
    50                  55                  60

Asn Glu Lys Met Phe Lys Leu Ala Arg Glu Ile Lys Gln Lys Phe Tyr
```

```
                65                  70                  75                  80
Gly Asn Arg Ile Val Met Phe Ala Pro Leu Tyr Leu Ser Asn Tyr Cys
                        85                  90                  95
Val Asn Gly Cys Val Tyr Cys Pro Tyr His Lys Asn Lys His Ile
                    100                 105                 110
Ala Arg Lys Lys Leu Ser Gln Glu Asp Val Lys Arg Glu Thr Ile Ala
                115                 120                 125
Leu Gln Asp Met Gly His Lys Arg Leu Ala Leu Glu Ala Gly Glu Asp
        130                 135                 140
Pro Val Asn Asn Pro Ile Glu Tyr Ile Leu Asp Cys Ile Lys Thr Ile
145                 150                 155                 160
Tyr Ser Ile Lys His Lys Asn Gly Ala Ile Arg Arg Val Asn Val Asn
                165                 170                 175
Ile Ala Ala Thr Thr Val Glu Asn Tyr Lys Leu Lys Asp Ala Gly
                    180                 185                 190
Ile Gly Thr Tyr Ile Leu Phe Gln Glu Thr Tyr Asn Lys Lys Ser Tyr
                    195                 200                 205
Glu Glu Leu His Pro Thr Gly Pro Lys His Asp Tyr Ala Tyr His Thr
        210                 215                 220
Glu Ala Met Asp Arg Ala Met Glu Gly Gly Ile Asp Asp Val Gly Ile
225                 230                 235                 240
Gly Val Leu Phe Gly Leu Asn Met Tyr Lys Tyr Asp Phe Val Gly Leu
                        245                 250                 255
Leu Met His Ala Glu His Leu Glu Ala Ala Met Gly Val Gly Pro His
                    260                 265                 270
Thr Ile Ser Val Pro Arg Ile Arg Pro Ala Asp Asp Ile Asp Pro Glu
            275                 280                 285
Asn Phe Ser Asn Ala Ile Ser Asp Glu Ile Phe Glu Lys Ile Val Ala
        290                 295                 300
Ile Ile Arg Ile Ala Val Pro Tyr Thr Gly Met Ile Val Ser Thr Arg
305                 310                 315                 320
Glu Ser Lys Lys Thr Arg Glu Arg Val Leu Glu Leu Gly Ile Ser Gln
                325                 330                 335
Ile Ser Gly Gly Ser Ser Thr Ser Val Gly Gly Tyr Val Glu Ser Glu
                340                 345                 350
Pro Glu Glu Asp Asn Ser Ser Gln Phe Glu Val Asn Asp Asn Arg Thr
            355                 360                 365
Leu Asp Glu Ile Val Asn Trp Leu Leu Glu Met Asn Tyr Ile Pro Ser
        370                 375                 380
Phe Cys Thr Ala Cys Tyr Arg Glu Gly Arg Thr Gly Asp Arg Phe Met
385                 390                 395                 400
Ser Leu Val Lys Ser Gly Gln Ile Ala Asn Cys Cys Gln Pro Asn Ala
                405                 410                 415
Leu Met Thr Leu Lys Glu Tyr Leu Glu Asp Tyr Ala Ser Ser Asn Thr
                    420                 425                 430
Gln Lys Asn Gly Glu Ala Leu Ile Ala Ser Glu Val Glu Lys Ile Pro
            435                 440                 445
Asn Glu Lys Val Lys Ser Ile Val Lys Lys His Leu Thr Glu Leu Lys
        450                 455                 460
Glu Gly Gln Arg Asp Phe Arg Phe
465                 470
```

<210> SEQ ID NO 32

```
<211> LENGTH: 5
<212> TYPE: PRT
<213> ORGANISM: Chlamydomonas reinhardtii
<220> FEATURE:
<221> NAME/KEY: MISC_FEATURE
<222> LOCATION: (2)..(2)
<223> OTHER INFORMATION: X is A or G
<220> FEATURE:
<221> NAME/KEY: MISC_FEATURE
<222> LOCATION: (4)..(4)
<223> OTHER INFORMATION: X is any amino acid

<400> SEQUENCE: 32

Glu Xaa Cys Xaa His
1               5

<210> SEQ ID NO 33
<211> LENGTH: 6
<212> TYPE: PRT
<213> ORGANISM: Chlamydomonas reinhardtii
<220> FEATURE:
<221> NAME/KEY: MISC_FEATURE
<222> LOCATION: (1)..(1)
<223> OTHER INFORMATION: X is L or V
<220> FEATURE:
<221> NAME/KEY: MISC_FEATURE
<222> LOCATION: (4)..(5)
<223> OTHER INFORMATION: X is G or A

<400> SEQUENCE: 33

Xaa His Cys Xaa Xaa Cys
1               5

<210> SEQ ID NO 34
<211> LENGTH: 6
<212> TYPE: PRT
<213> ORGANISM: Chlamydomonas reinhardtii
<220> FEATURE:
<221> NAME/KEY: MISC_FEATURE
<222> LOCATION: (3)..(3)
<223> OTHER INFORMATION: X is A or G

<400> SEQUENCE: 34

Cys Thr Xaa Cys Tyr Arg
1               5
```